United States Patent
Gee et al.

(10) Patent No.: US 8,680,320 B2
(45) Date of Patent: Mar. 25, 2014

(54) HEAVY METAL BINDING COMPOUNDS AND THEIR METHOD OF USE

(75) Inventors: Kyle Gee, Springfield, OR (US); Jolene Bradford, Eugene, OR (US); Vladimir Martin, Eugene, OR (US)

(73) Assignee: Life Technologies Corporation, Carlsbad, CA (US)

( * ) Notice: Subject to any disclaimer, the term of this patent is extended or adjusted under 35 U.S.C. 154(b) by 468 days.

(21) Appl. No.: 12/636,687

(22) Filed: Dec. 11, 2009

(65) Prior Publication Data

US 2010/0167333 A1    Jul. 1, 2010

Related U.S. Application Data

(60) Continuation of application No. 12/397,896, filed on Mar. 4, 2009, now abandoned, which is a division of application No. 11/622,900, filed on Jan. 12, 2007, now Pat. No. 7,521,577.

(60) Provisional application No. 60/758,830, filed on Jan. 12, 2006.

(51) Int. Cl.
C07C 229/00    (2006.01)
C07C 321/00    (2006.01)

(52) U.S. Cl.
USPC .............. 560/44; 562/426; 562/436; 562/452

(58) Field of Classification Search
USPC .............................. 560/44; 562/426, 436, 452
See application file for complete search history.

(56) References Cited

U.S. PATENT DOCUMENTS

| | | | |
|---|---|---|---|
| 4,384,042 A | 5/1983 | Miike et al. |
| 4,520,110 A | 5/1985 | Stryer et al. |
| 4,542,104 A | 9/1985 | Stryer et al. |
| 4,603,209 A | 7/1986 | Tsien et al. |
| 4,711,955 A | 12/1987 | Ward et al. |
| 4,774,339 A | 9/1988 | Haugland et al. |
| 4,810,636 A | 3/1989 | Corey et al. |
| 4,812,409 A | 3/1989 | Babb et al. |
| 4,849,362 A | 7/1989 | Demarinis et al. |
| 4,859,582 A | 8/1989 | Stryer et al. |
| 4,945,171 A | 7/1990 | Haugland et al. |
| 5,047,519 A | 9/1991 | Hobbs et al. |
| 5,055,556 A | 10/1991 | Stryer et al. |
| 5,187,288 A | 2/1993 | Kang et al. |
| 5,196,306 A | 3/1993 | Bobrow et al. |
| 5,208,148 A | 5/1993 | Haugland et al. |
| 5,227,487 A | 7/1993 | Haugland et al. |
| 5,242,805 A | 9/1993 | Naleway et al. |
| 5,248,782 A | 9/1993 | Haugland et al. |
| 5,268,486 A | 12/1993 | Waggoner et al. |
| 5,274,113 A | 12/1993 | Kang et al. |
| 5,352,803 A | 10/1994 | Mattingly |
| 5,362,628 A | 11/1994 | Haugland et al. |
| 5,433,896 A | 7/1995 | Kang et al. |
| 5,442,045 A | 8/1995 | Haugland et al. |
| 5,451,343 A | 9/1995 | Neckers et al. |
| 5,453,517 A | 9/1995 | Kuhn et al. |
| 5,459,276 A | 10/1995 | Kuhn et al. |
| 5,486,616 A | 1/1996 | Waggoner et al. |
| 5,501,980 A | 3/1996 | Katerinopoulos et al. |
| 5,569,587 A | 10/1996 | Waggoner |
| 5,569,766 A | 10/1996 | Waggoner et al. |
| 5,573,904 A | 11/1996 | Mattingly |
| 5,583,001 A | 12/1996 | Bobrow et al. |
| 5,656,554 A | 8/1997 | Desai et al. |
| 5,696,157 A | 12/1997 | Wang et al. |
| 5,714,327 A | 2/1998 | Houthoff et al. |
| 5,731,158 A | 3/1998 | Bobrow et al. |
| 5,773,236 A | 6/1998 | Diwu et al. |
| 5,798,276 A | 8/1998 | Haugland et al. |
| 5,800,996 A | 9/1998 | Lee et al. |
| 5,830,912 A | 11/1998 | Gee et al. |
| 5,846,737 A | 12/1998 | Kang |
| 5,847,162 A | 12/1998 | Lee et al. |
| 5,863,727 A | 1/1999 | Lee et al. |
| 5,945,526 A | 8/1999 | Lee et al. |
| 6,008,373 A | 12/1999 | Waggoner et al. |
| 6,008,379 A | 12/1999 | Benson et al. |
| 6,017,712 A | 1/2000 | Lee et al. |
| 6,025,505 A | 2/2000 | Lee et al. |
| 6,048,982 A | 4/2000 | Waggoner |
| 6,080,852 A | 6/2000 | Lee et al. |
| 6,127,133 A | 10/2000 | Akong et al. |
| 6,130,101 A | 10/2000 | Mao et al. |
| 6,140,494 A | 10/2000 | Hamilton et al. |

(Continued)

OTHER PUBLICATIONS

U.S. Appl. No. 11/622,900, "Non-final Office Action mailed Aug. 5, 2008".
U.S. Appl. No. 11/622,900, "Response to Non-final Office Action mailed Aug. 5, 2008, filed Nov. 5, 2008".
U.S. Appl. No. 11/622,900, "Response to Restriction Requirement mailed 1/29/08, filed Feb. 25, 2008".
U.S. Appl. No. 11/622,900, "Response to Restriction Requirement mailed Mar. 27, 2008, filed Jun. 6, 2008".
U.S. Appl. No. 11/622,900, "Restriction Requirement mailed Jan. 29, 2008".
U.S. Appl. No. 11/622,900, "Restriction Requirement mailed Mar. 27, 2008".

(Continued)

Primary Examiner — Nizal Chandrakumar
(74) Attorney, Agent, or Firm — Life Technologies Corporation

(57) ABSTRACT

The present invention provides a metal chelator and methods that facilitate binding, detecting, monitoring and quantitating of heavy metal ions in a sample. This metal chelating moiety is a —N,N,O-triacetic acid analog of BAPTA and has the following formula

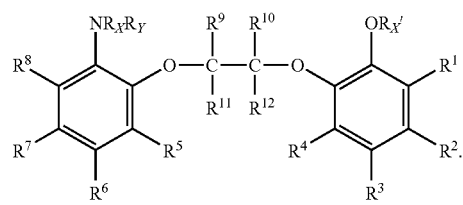

24 Claims, 18 Drawing Sheets

(56) References Cited

U.S. PATENT DOCUMENTS

| | | | |
|---|---|---|---|
| 6,162,931 | A | 12/2000 | Gee et al. |
| 6,184,379 | B1 | 2/2001 | Josel et al. |
| 6,221,606 | B1 | 4/2001 | Benson et al. |
| 6,335,440 | B1 | 1/2002 | Lee et al. |
| 6,339,392 | B1 | 1/2002 | Ashihara et al. |
| 6,348,599 | B1 | 2/2002 | Cummins et al. |
| 6,358,684 | B1 | 3/2002 | Lee |
| 6,372,445 | B1 | 4/2002 | Davis et al. |
| 6,403,807 | B1 | 6/2002 | Singh et al. |
| 6,562,632 | B1 | 5/2003 | Szalecki et al. |
| 6,664,047 | B1 | 12/2003 | Haugland et al. |
| 6,716,979 | B2 | 4/2004 | Diwu et al. |
| 6,977,305 | B2 | 12/2005 | Leung et al. |
| 7,521,577 | B2 | 4/2009 | Gee |
| 2007/0161112 | A1 | 7/2007 | Gee et al. |

OTHER PUBLICATIONS

U.S. Appl. No. 12/397,896, "Corrected Application Papers mailed Mar. 26, 2010".
U.S. Appl. No. 12/397,896, "Corrected Application Papers mailed Jul. 17, 2009".
U.S. Appl. No. 11/622,900, "Notice of Allowance mailed Dec. 9, 2008".
Bouizar, Z. et al., "Purification and Characterization of Calcitonin Receptors in Rat Kidney Membranes by Covalent Cross-Linking Techniques.", *Eur J Biochem* vol. 155(1) 1986, pp. 141-147.
Brinkley, Michael, "A Brief Survey of Methods for Preparing Protein Conjugates with Dyes, Haptens, and Cross-Linking Reagents", *Bioconjugate Chem.* vol. 3, No. 1 1992, 2-13.
Browning, Jeffrey et al., "Studies on the Differing Effects of the Tumor Necrosis Factor and Lymphotoxin on the Growth of Several Human Tumor Lines", *The Journal of Immunology* vol. 143, No. 6 1989, pp. 1859-1867.
Furniss, Brian S. et al., "Resolution of Racemates", *Vogel's Textbook of Practical Organic Chemistry* Fifth Ed, Longman Group UK Ltd., Essex 1989, 809-823.
Haugland, Richard P., "Molecular Probes Handbook of Fluorescent Probes and Research Products", *Table of Contents* 9th edition, CD ROM, Molecular Probes, Inc. 2002, 1-6.
Heller, A., "Electrical Wiring of Redox Enzymes", *Acc. Chem. Res.* vol. 23, No. 5 1990, 128-134.
Joshi, S. et al., "ATP Synthase complex from Bovine Heart Mitochondria. Subunit Arrangements as Revealed by Nearest Analysis and Susceptibility to Trypsin", *The Journal of Biological Chemistry* vol. 256, No. 24 1990, pp. 14518-14525.
Jung, S. M. et al., "Crosslinking of Platelet Glycoprotein Ib by N-Succinimidyl (4-azidophenyldithio) Propionate and 3, 3'-dithiobis (Sulfosuccinimidyl Promionate)", *Biochimica et Biophysica Acta* vol. 761 1983, pp. 152-162.
Park, Linda S. et al., "Characterization of the Cell Surface Receptor for a Multi-Lineage Colony-Stimulating Factor (CSF-2alpha)*", *The Journal of Biological Chemistry* vol. 261, No. 1 1986, pp. 205-210.
Patton, Wayne F., "A Thousand Points of Light: The Application of Fluorescence Detection Technologies to Two Dimensional Gel Electrophoresis and Proteomics", *Electrophoresis* vol. 21, No. 6 2000, 1123-1144.
Patton, W. F., "Detection Technologies in Proteome Analysis", *Journal of Chromatography B* vol. 771, No. 1-2 2002, 3-31.
Zarling, David A. et al., "Mapping of Lymphocyte Surface Polypeptide Antigens by Chemical Cross-Linking with BSOCOES", *The Journal of Immunology* vol. 124, No. 2 1980, pp. 913-920.

HEAVY METAL BINDING COMPOUNDS AND THEIR METHOD OF USE

CROSS REFERENCE TO RELATED APPLICATION

This application is a continuation application of U.S. patent application Ser. No. 12/397,896, filed Mar. 4, 2009, which is a divisional application of U.S. patent application Ser. No. 11/622,900, filed Jan. 12, 2007, now U.S. Pat. No. 7,521,577, which claims priority to U.S. Provisional Patent Application No. 60/758,830, filed Jan. 12, 2006, the disclosures of which are hereby incorporated herein by reference in their entirety as if set forth fully herein.

FIELD OF THE INVENTION

The present invention relates to novel compositions and methods for the detection of heavy metal ions. The invention has applications in the fields of cell biology, neurology, nutrition, immunology, reproductive biology, cancer and proteomics.

BACKGROUND OF THE INVENTION

Certain transition and heavy metal ions pose increasing environmental and health risks. For example, as the use of Ni—Cd batteries increases, so does the prevalence of nickel and cadmium ions in manufacturing, disposal, and environmental contamination. It has long been known that mercury ions are a persistent and prevalent health risk, with a large percentage of the populace exposed to the risk. The same goes for lead ions, found in peeling paint on older buildings. These increasing incidences result in increasing exposures and internalization of these ions within individuals.

Thus there exists a need for increasingly sophisticated methods for the detection and quantitation of certain heavy metal and transition metal ions in a variety of samples, ranging from groundwater and soil to inside human cells. In the biomedical research field, luminescence-based probes of alkaline earth metal cations such as calcium have been of enormous benefit. To date there have been some examples of luminescence-based detection methods developed for heavy metal and transition metal ions. However these existing methods rely upon substandard compounds which lack specificity, dynamic range, sensitivity, and applicability to field use. The present invention addresses these shortcomings by describing novel luminescence-based materials that are very useful for the detection and quantitation of certain metal ions such as cadmium(II), lead(II), mercury(II), and nickel(II).

SUMMARY OF THE INVENTION

Embodiments of the present invention provide metal ion reporter compounds according to the formula:

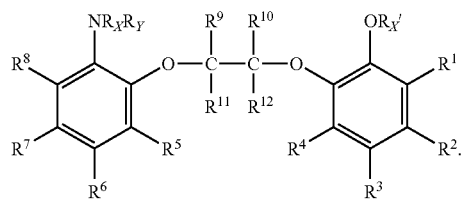

$R_X$, $R_Y$, and $R_X'$ are each independently is hydrogen, alkyl, substituted alkyl or —$CR^{13}R^{14}CO_2R$, wherein R is H, a salt ion or —$CH_2OC(O)(CH_2)_nCH_3$ and n is 0 to 6. Each $R^{13}$ and $R^{14}$ is independently hydrogen, alkyl or substituted alkyl.

$R^1$-$R^8$ are independently hydrogen, halogen, alkyl, substituted alkyl, alkoxy, substituted alkoxy, hydroxyl, aryl, substituted aryl, heteroaryl, substituted heteroaryl, amino, substituted amino, alkylamino, substituted alkylamino, aldehyde, carboxyl, azido, nitro, nitroso, cyano, thioether, sulfoalkyl, carboxyalkyl, aminoalkyl, reporter molecule, reactive group, carrier molecule or solid support. Alternatively, any adjacent $R^1$-$R^8$ together with the atoms to which they are joined, form a ring which is a 5-, 6- or 7-membered heterocycloalkyl, a substituted 5-, 6- or 7-membered heterocycloalkyl, a 5-, 6- or 7-membered cycloalkyl, a substituted 5-, 6- or 7-membered cycloalkyl, a 5-, 6- or 7-membered heteroaryl, a substituted 5-, 6- or 7-membered heteroaryl, a 5-, 6- or 7-membered aryl, a substituted 5-, 6- or 7-membered aryl or reporter molecule.

The bridge substituents $R^9$-$R^{12}$ are independently hydrogen, alkyl, substituted alkyl, reactive group, carrier molecule, or solid support. Alternatively, $R^9$ in combination with $R^{10}$; or $R^{11}$ in combination with $R^{12}$ together with the atoms to which they are joined, form a ring which is a 5-, 6- or 7-membered heterocycloalkyl, a substituted 5-, 6- or 7-membered heterocycloalkyl, a 5-, 6- or 7-membered cycloalkyl, a substituted 5-, 6- or 7-membered cycloalkyl, a 5-, 6- or 7-membered heteroaryl, a substituted 5-, 6- or 7-membered heteroaryl, a 5-, 6- or 7-membered aryl, or a substituted 5-, 6- or 7-membered aryl.

In one embodiment, the present compound comprises a reporter molecule that is a chromophore, fluorophore, fluorescent protein, phosphorescent dye or a tandem dye. In one aspect, the reporter molecule is a xanthene, indole, cyanine, oxazole, dansyl, borapolyazaindacene, benzofuran, quinazolinone, benzazole, oxazine, pyrene, naphthalene, coumarin, biotin, enzyme substrate or fluorescent protein. In a further aspect, the xanthene is a fluorescein or derivative thereof, rhodamine or derivative thereof, rhodol or derivative thereof or rosamine or a derivative thereof. In another further aspect, the reporter molecule is optionally and independently substituted by hydrogen, halogen, amino, substituted amino, alkyl, substituted alkyl, aryl, substituted aryl, heteroaryl, substituted heteroaryl, alkoxy, sulfo, lipophilic group (AM ester or acetate ester) solid support, reactive group or carrier molecule.

Additional embodiments of the present invention provide methods of detecting the presence or absence of metal ions in a sample. The present methods comprise:

a. combining a present metal ion reporter molecule with the sample to prepare a labeling mixture;

b. incubating the labeling mixture for a sufficient amount of time for the metal ion reporter molecule to associate with metal ions in the sample to form an incubated mixture;

c. illuminating the incubated sample with an appropriate wavelength to form an illuminated mixture; and, d. observing the illuminated mixture whereby the presence or absence of the metal ions in a sample is detected.

Also provided is a staining solution comprising a present compound and an aqueous buffer solution. In one aspect the aqueous buffer solution is normal saline, PBS, cell culture media, MOPS, Good's buffer or PIPES buffer.

Further embodiments provide complexes of the present compounds non-covalently associated with metal ions and compositions comprising a present compound and a sample. In one aspect the sample comprises living cells, cellular components, proteins, peptides, buffer solutions, intracellular fluids, extracellular fluids, fixed cells, biological fermentation media, environmental sample, industrial samples or chemical reactors, eukaryotic cells, or prokaryotic cells. In a further aspect, the sample comprises blood cells, immune cells, cultured cells, muscle tissue, neurons, extracellular vesicles; vascular tissue, blood fluids, saliva, urine; water, soil, waste water, sea water; pharmaceuticals, foodstuffs or beverages.

Additional embodiments of the present invention provide kits for the detection of metal ions, wherein the kit comprises any compound of the present invention. In a further embodiment, the kits comprise instructions for detecting the presence or absence of lead, mercury, nickel, lanthanum or cadmium ions in a sample, in particular are included instructions for detecting the presence or absence of lead, mercury, nickel, lanthanum or cadmium ions in a sample using flow cytometry. In yet another further aspect, the kits comprises at least one component that is a sample preparation reagent, a buffering agent, aqueous metal ion reporter molecule dilution buffer, an additional detection reagent, a metal ion calibration reagent, a positive control, a metal ion indicator other than for lead, mercury, nickel, lanthanum or cadmium ions, an antibody or fragment thereof or a reference dye standard.

DETAILED DESCRIPTION OF THE INVENTION

Introduction

Figure 1A:
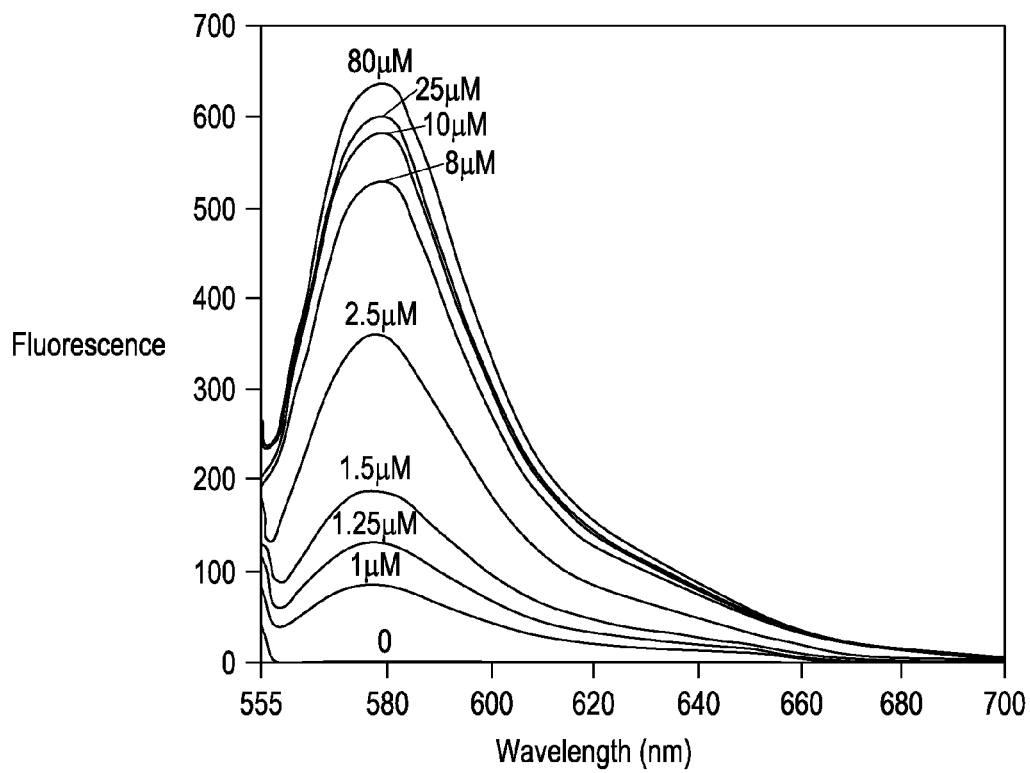
FIG. 1: Shows the detection and titration of A) lead ions (0 to 50 μM) (Kd=2.1 μM), B) cadmium ions (0 to 100 μM) (Kd=4.6 μM) and C) mercury ions (0 to 100 μM) (Kd=78 μM) in a solution containing MOPS (pH 7.0) and 1 μM of Compound 15. Excitation 550 nm.

The present invention provides heavy metal-binding compounds for the binding, including sequestering of ions, detection, monitoring and quantification of heavy metal ions, including physiological concentrations of heavy metal ions that are present in intracellular and extracellular biological fluids. The heavy metal-binding compounds preferentially bind heavy metal ions (lead, cadmium, mercury, nickel, and/ or lanthanum) in the presence of physiological concentrations of calcium ions, this property being a function of the chelating moiety of the heavy metal-binding compounds, and provides a mechanism for binding and detecting heavy metal ions in the presence of calcium ions.

DEFINITIONS

Before describing the present invention in detail, it is to be understood that this invention is not limited to specific compositions or process steps, as such may vary. It must be noted that, as used in this specification and the appended claims, the singular form "a", "an" and "the" include plural referents unless the context clearly dictates otherwise.

Thus, for example, reference to "a present compound" includes a plurality of compounds and reference to "a metal ion" includes a plurality of ions and the like.

Unless defined otherwise, all technical and scientific terms used herein have the same meaning as commonly understood by one of ordinary skill in the art to which this invention is related. The following terms are defined for purposes of the invention as described herein.

The term "affinity" as used herein refers to the strength of the binding interaction of two molecules, such as a metal chelating compound and a metal ion or a positively charged moiety and a negatively charged moiety.

Certain compounds of the present invention can exist in unsolvated forms as well as solvated forms, including hydrated forms. In general, the solvated forms are equivalent to unsolvated forms and are encompassed within the scope of the present invention. Certain compounds of the present invention may exist in multiple crystalline or amorphous forms. In general, all physical forms are equivalent for the uses contemplated by the present invention and are intended to be within the scope of the present invention.

Certain compounds of the present invention possess asymmetric carbon atoms (optical centers) or double bonds; the racemates, diastereomers, geometric isomers and individual isomers are encompassed within the scope of the present invention.

The compounds of the invention may be prepared as a single isomer (e.g., enantiomer, cis-trans, positional, diastereomer) or as a mixture of isomers. In a preferred embodiment, the compounds are prepared as substantially a single isomer. Methods of preparing substantially isomerically pure compounds are known in the art. For example, enantiomerically enriched mixtures and pure enantiomeric compounds can be prepared by using synthetic intermediates that are enantiomerically pure in combination with reactions that either leave the stereochemistry at a chiral center unchanged or result in its complete inversion. Alternatively, the final product or intermediates along the synthetic route can be resolved into a single stereoisomer. Techniques for inverting or leaving unchanged a particular stereocenter, and those for resolving mixtures of stereoisomers are well known in the art and it is well within the ability of one of skill in the art to choose and appropriate method for a particular situation. See, generally, Furniss et al. (eds.), VOGEL's ENCYCLOPEDIA OF PRACTICAL ORGANIC CHEMISTRY $5^{TH}$ ED., Longman Scientific and Technical Ltd., Essex, 1991, pp. 809-816; and Heller, *Acc. Chem. Res.* 23: 128 (1990).

The compounds of the present invention may also contain unnatural proportions of atomic isotopes at one or more of the atoms that constitute such compounds. For example, the compounds may be radiolabeled with radioactive isotopes, such as for example tritium ($^3$H), iodine-125 ($^{125}$I) or carbon-14 ($^{14}$C). All isotopic variations of the compounds of the present invention, whether radioactive or not, are intended to be encompassed within the scope of the present invention.

Where substituent groups are specified by their conventional chemical formulae, written from left to right, they equally encompass the chemically identical substituents, which would result from writing the structure from right to left, e.g., —CH$_2$O— is intended to also recite —OCH$_2$—.

The term "acyl" or "alkanoyl" by itself or in combination with another term, means, unless otherwise stated, a stable straight or branched chain, or cyclic hydrocarbon radical, or combinations thereof, consisting of the stated number of carbon atoms and an acyl radical on at least one terminus of the alkane radical. The "acyl radical" is the group derived from a carboxylic acid by removing the —OH moiety therefrom.

The term "alkyl," by itself or as part of another substituent means, unless otherwise stated, a straight or branched chain, or cyclic hydrocarbon radical, or combination thereof, which may be fully saturated, mono- or polyunsaturated and can include divalent ("alkylene") and multivalent radicals, having the number of carbon atoms designated (i.e. $C_1$-$C_{10}$ means one to ten carbons). Examples of saturated hydrocarbon radicals include, but are not limited to, groups such as methyl, ethyl, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. The term "alkyl," unless otherwise noted, is also meant to include those derivatives of alkyl defined in more detail below, such as "heteroalkyl." Alkyl groups that are limited to hydrocarbon groups are termed "homoalkyl".

Exemplary alkyl groups of use in the present invention contain between about one and about twenty-five carbon atoms (e.g. methyl, ethyl and the like). Straight, branched or cyclic hydrocarbon chains having eight or fewer carbon atoms will also be referred to herein as "lower alkyl". In addition, the term "alkyl" as used herein further includes one or more substitutions at one or more carbon atoms of the hydrocarbon chain fragment.

The terms "alkoxy," "alkylamino" and "alkylthio" (or thioalkoxy) are used in their conventional sense, and refer to those alkyl groups attached to the remainder of the molecule via an oxygen atom, an amino group, or a sulfur atom, respectively.

The term "heteroalkyl," by itself or in combination with another term, means, unless otherwise stated, a straight or branched chain, or cyclic carbon-containing radical, or combinations thereof, consisting of the stated number of carbon atoms and at least one heteroatom selected from the group consisting of O, N, Si, P and S, and wherein the nitrogen, phosphorous and sulfur atoms are optionally oxidized, and the nitrogen heteroatom is optionally be quaternized. The heteroatom(s) O, N, P, S and Si may be placed at any interior position of the heteroalkyl group or at the position at which the alkyl group is attached to the remainder of the molecule. Examples include, but are not limited to, —CH$_2$—CH$_2$—O—CH$_3$, —CH$_2$—CH$_2$—NH—CH$_3$, —CH$_2$—CH$_2$—N(CH$_3$)—CH$_3$, —CH$_2$—S—CH$_2$—CH$_3$, —CH$_2$—CH$_2$, —S(O)—CH$_3$, —CH$_2$—CH$_2$—S(O)$_2$—CH$_3$, —CH=CH—O—CH$_3$, —Si(CH$_3$)$_3$, —CH$_2$—CH=N—OCH$_3$, and —CH=CH—N(CH$_3$)—CH$_3$. Up to two heteroatoms may be consecutive, such as, for example, —CH$_2$—NH—OCH$_3$ and —CH$_2$—O—Si(CH$_3$)$_3$. Similarly, the term "heteroalkylene" by itself or as part of another substituent means a divalent radical derived from heteroalkyl, as exemplified, but not limited by, —CH$_2$—CH$_2$—S—CH$_2$—CH$_2$— and —CH$_2$—S—CH$_2$—CH$_2$—NH—CH$_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —C(O)$_2$R'— represents both —C(O)$_2$R'— and —R'C(O)$_2$—.

The terms "cycloalkyl" and "heterocycloalkyl", by themselves or in combination with other terms, represent, unless otherwise stated, cyclic versions of "alkyl" and "heteroalkyl", respectively. Additionally, for heterocycloalkyl, a heteroatom can occupy the position at which the heterocycle is attached to the remainder of the molecule. Examples of cycloalkyl include, but are not limited to, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like.

The term "aryl" means, unless otherwise stated, a polyunsaturated, aromatic moiety that can be a single ring or multiple rings (preferably from 1 to 3 rings), which are fused together or linked covalently.

The term "heteroaryl" as used herein refers to an aryl group as defined above in which one or more carbon atoms have been replaced by a non-carbon atom, especially nitrogen, oxygen, or sulfur. For example, but not as a limitation, such groups include furyl, tetrahydrofuryl, pyrrolyl, pyrrolidinyl, thienyl, tetrahydrothienyl, oxazolyl, isoxazolyl, triazolyl, thiazolyl, isothiazolyl, pyrazolyl, pyrazolidinyl, oxadiazolyl, thiadiazolyl, imidazolyl, imidazolinyl, pyridyl, pyridaziyl, triazinyl, piperidinyl, morpholinyl, thiomorpholinyl, pyrazinyl, piperainyl, pyrimidinyl, naphthyridinyl, benzofuranyl, benzothienyl, indolyl, indolinyl, indolizinyl, indazolyl, quinolizinyl, quinolinyl, isoquinolinyl, cinnolinyl, phthalazinyl, quinazolinyl, quinoxalinyl, pteridinyl, quinuclidinyl, carbazolyl, acridinyl, phenazinyl, phenothizinyl, phenoxazinyl, purinyl, benzimidazolyl and benzthiazolyl and their aromatic ring-fused analogs. Many fluorophores are comprised of heteroaryl groups and include, without limitations, xanthenes, oxazines, benzazolium derivatives (including cyanines and carbocyanines), borapolyazaindacenes, benzofurans, indoles and quinazolones.

The above heterocyclic groups may further include one or more substituents at one or more carbon and/or non-carbon atoms of the heteroaryl group, e.g., alkyl; aryl; heterocycle; halogen; nitro; cyano; hydroxyl, alkoxyl or aryloxyl; thio or mercapto, alkyl- or arylthio; amino, alkyl-, aryl-, dialkyl-, diaryl-, or arylalkylamino; aminocarbonyl, alkylaminocarbonyl, arylaminocarbonyl, dialkylaminocarbonyl, diarylaminocarbonyl or arylalkylaminocarbonyl; carboxyl, or alkyl- or aryloxycarbonyl; aldehyde; aryl- or alkylcarbonyl; iminyl, or aryl- or alkyliminyl; sulfo; alkyl- or arylsulfonyl; hydroximinyl, or aryl- or alkoximinyl. In addition, two or more alkyl substituents may be combined to form fused heterocycle-alkyl ring systems. Substituents including heterocyclic groups (e.g., heteroaryloxy, and heteroaralkylthio) are defined by analogy to the above-described terms.

The term "heterocycloalkyl" as used herein refers to a heterocycle group that is joined to a parent structure by one or more alkyl groups as described above, e.g., 2-piperidylmethyl, and the like. The term "heterocycloalkyl" refers to a heteroaryl group that is joined to a parent structure by one or more alkyl groups as described above, e.g., 2-thienylmethyl, and the like.

For brevity, the term "aryl" when used in combination with other terms (e.g., aryloxy, arylthioxy, arylalkyl) includes both aryl and heteroaryl rings as defined above. Thus, the term "arylalkyl" is meant to include those radicals in which an aryl group is attached to an alkyl group (e.g., benzyl, phenethyl, pyridylmethyl and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like).

Each of the above terms (e.g., "alkyl," "heteroalkyl," "aryl" and "heteroaryl") includes both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) are generically referred to as "alkyl group substituents," and they can be one or more of a variety of groups selected from, but not limited to: —OR', =O, =NR', =N—OR', —NR'R", —SR', -halogen, —SiR'R"R'", —OC(O)R', —C(O)R', —CO$_2$R', —CONR'R", —OC(O)NR'R", —NR"C(O)R', —NR'—C(O)NR"R'", —NR"C(O)$_2$R', —NR—C(NR'R"R'")=NR"", —NR—C(NR'R")=NR'", —S(O)R', —S(O)$_2$R', —S(O)$_2$NR'R", —NRSO$_2$R', —CN and —NO$_2$ in a number ranging from zero to (2m'+1), where m' is the total number of carbon atoms in such radical. R', R", R'" and R"" each preferably independently refer to hydrogen, substituted or unsubstituted heteroalkyl, substituted or unsubstituted aryl, e.g., aryl substituted with 1-3 halogens, substituted or unsubstituted alkyl, alkoxy or thioalkoxy groups, or arylalkyl groups. When a compound of the invention includes more than one R group, for example, each of the R groups is independently selected as are each R', R", R'" and R"" groups when more than one of these groups is present. When R' and R" are attached to the same nitrogen atom, they can be combined with the nitrogen atom to form a 5-, 6-, or 7-membered ring. For example, —NR'R" is meant to include, but not be limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like).

Similar to the substituents described for the alkyl radical, substituents for the aryl and heteroaryl groups are generically referred to as "aryl group substituents." The substituents are selected from, for example: halogen, —OR', =O, =NR', =N—OR', —NR'R", —SR', -halogen, —SiR'R"R'", —OC(O)R', —C(O)R', —CO$_2$R', —CONR'R", —OC(O)NR'R", —NR"C(O)R', —NR'—C(O)NR"R'", —NR"C(O)$_2$R', —NR—C(NR'R"R'")=NR"", —NR—C(NR'R")=NR'", —S(O)R', —S(O)$_2$R', —S(O)$_2$NR'R", —NRSO$_2$R', —CN and —NO$_2$, —R', —N$_3$, —CH(Ph)$_2$, fluoro(C$_1$-C$_4$)alkoxy, and fluoro(C$_1$-C$_4$)alkyl, in a number ranging from zero to the total number of open valences on the aromatic ring system; and where R', R", R'" and R"" are preferably independently selected from hydrogen, substituted or unsubstituted alkyl, substituted or unsubstituted heteroalkyl, substituted or unsubstituted aryl and substituted or unsubstituted heteroaryl. When a compound of the invention includes more than one R group, for example, each of the R groups is independently selected as are each R', R", R'" and R"" groups when more than one of these groups is present. In the schemes that follow, the symbol X represents "R" as described above.

Two of the substituents on adjacent atoms of the aryl or heteroaryl ring may optionally be replaced with a substituent of the formula -T-C(O)—(CRR')$_q$—U—, wherein T and U are independently —NR—, —O—, —CRR'— or a single bond, and q is an integer of from 0 to 3. Alternatively, two of the substituents on adjacent atoms of the aryl or heteroaryl ring may optionally be replaced with a substituent of the formula -A-(CH$_2$)$_r$—B—, wherein A and B are independently —CRR'—, —O—, —NR—, —S—, —S(O)—, —S(O)$_2$—, —S(O)$_2$NR'— or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')$_s$—X—(CR"R''')$_d$—, where s and d are independently integers of from 0 to 3, and X is —O—, —NR'—, —S—, —S(O)—, —S(O)$_2$—, or —S(O)$_2$NR'—. The substituents R, R', R" and R''' are preferably independently selected from hydrogen or substituted or unsubstituted (C$_1$-C$_6$)alkyl.

As used herein, the term "heteroatom" includes oxygen (O), nitrogen (N), sulfur (S), phosphorus (P) and silicon (Si).

The term "amino" or "amine group" refers to the group —NR'R" (or NRR'R") where R, R' and R" are independently selected from the group consisting of hydrogen, alkyl, substituted alkyl, aryl, substituted aryl, aryl alkyl, substituted aryl alkyl, heteroaryl, and substituted heteroaryl. A substituted amine being an amine group wherein R' or R" is other than hydrogen. In a primary amino group, both R' and R" are hydrogen, whereas in a secondary amino group, either, but not both, R' or R" is hydrogen. In addition, the terms "amine" and "amino" can include protonated and quaternized versions of nitrogen, comprising the group —NRR'R" and its biologically compatible anionic counterions.

The term "aqueous solution" as used herein refers to a solution that is predominantly water and retains the solution characteristics of water. Where the aqueous solution contains solvents in addition to water, water is typically the predominant solvent.

The term "biotin" as used herein refers to any biotin derivative, including without limitation, substituted and unsubstituted biotin, and analogs and derivatives thereof, as well as substituted and unsubstituted derivatives of caproylamidobiotin, biocytin, desthiobiotin, desthiobiocytin, iminobiotin, and biotin sulfone.

The term "buffer" as used herein refers to a system that acts to minimize the change in acidity or basicity of the solution against addition or depletion of chemical substances.

The term "carbonyl" as used herein refers to the functional group —(C═O)—. However, it will be appreciated that this group may be replaced with other well-known groups that have similar electronic and/or steric character, such as thiocarbonyl (—(C═S)—); sulfinyl (—S(O)—); sulfonyl (—SO$_2$)—), phosphonyl (—PO$_2$—).

The term "carboxy" or "carboxyl" refers to the group —R'(COOR) where R' is alkyl, substituted alkyl, aryl, substituted aryl, arylalkyl, substituted arylalkyl, heteroaryl, or substituted heteroaryl. R is hydrogen, a salt or —CH$_2$OC(O)CH$_3$.

The term "carrier molecule" as used herein refers to a biological or a non-biological component that s covalently bonded to compound of the present invention. Such components include, but are not limited to, an amino acid, a peptide, a protein, a polysaccharide, a nucleoside, a nucleotide, an oligonucleotide, a nucleic acid, a hapten, a psoralen, a drug, a hormone, a lipid, a lipid assembly, a synthetic polymer, a polymeric microparticle, a biological cell, a virus and combinations thereof.

The term "cell permeable" as used herein refers to compounds of the present invention that are able to cross the cell membrane of live cells. Lipophilic groups that are covalently attached to the present compounds facilitate this permeability and live cell entry. Once inside the cells, the lipophilic groups are hydrolyzed resulting in charged molecules that are well retained in living cells. Particularly useful lipophilic groups include acetoxymethyl (AM) ester and acetate esters wherein once inside the cells the groups are cleaved by nonspecific esterases resulting in charged molecules.

The term "complex" as used herein refers to the association of two or more molecules, usually by non-covalent bonding.

The term "detectable response" as used herein refers to a change in or an occurrence of, a signal that is directly or indirectly detectable either by observation or by instrumentation. Typically, the detectable response is an optical response resulting in a change in the wavelength distribution patterns or intensity of absorbance or fluorescence or a change in light scatter, fluorescence lifetime, fluorescence polarization, or a combination of the above parameters. Alternatively, the detectable response is an occurrence of a signal wherein the fluorophore is inherently fluorescent and does not produce a change in signal upon binding to a metal ion. Alternatively, the detectable response is the result of a signal, such as color, fluorescence, radioactivity or another physical property of the detectable label becoming spatially localized in a subset of a sample such as in a gel, on a blot, or an array, in a well of a microplate, in a microfluidic chamber, or on a microparticle as the result of formation of a ternary complex of the invention that comprises a zinc binding protein.

The term "directly detectable" as used herein refers to the presence of a detectable label or the signal generated from a detectable label that is immediately detectable by observation, instrumentation, or film without requiring chemical modifications or additional substances. For example, a fluorophore produces a directly detectable response.

The term "dye" as used herein refers to a compound that emits light to produce an observable detectable signal. "Dye" includes fluorescent and nonfluorescent compounds that include without limitations pigments, fluorophores, chemiluminescent compounds, luminescent compounds and chromophores. The term "fluorophore" as used herein refers to a compound that is inherently fluorescent or demonstrates a change in fluorescence upon binding to a biological compound or metal ion, i.e., fluorogenic. Numerous fluorophores are known to those skilled in the art and include, but are not limited to, coumarin, acridine, furan, indole, quinoline, cyanine, benzofuran, quinazolinone, benzazole, borapolyazaindacene and xanthenes, with the latter including fluoroscein, rhodamine, rhodol, rosamine and derivatives thereof as well as other fluorophores described in RICHARD P. HAUGLAND, MOLECULAR PROBES HANDBOOK OF FLUORESCENT PROBES AND RESEARCH CHEMICALS (9$^{th}$ edition, CD-ROM, 2002).

The term "kit" as used herein refers to a packaged set of related components, typically one or more compounds or compositions.

The term "Linker" or "L", as used herein, refers to a single covalent bond or a series of stable covalent bonds incorporating 1-30 nonhydrogen atoms selected from the group consisting of C, N, O, S and P that covalently attach the phosphate-binding compounds to another moiety such as a chemically reactive group or a phosphorylated target molecule. Exemplary linking members include a moiety that includes —C(O)NH—, —C(O)O—, —NH—, —S—, —O—, and the like. A "cleavable linker" is a linker that has one or more cleavable groups that may be broken by the result of a reaction or condition. The term "cleavable group" refers to a moiety that allows for release of a portion, e.g., a reporter molecule, carrier molecule or solid support, of a conjugate from the remainder of the conjugate by cleaving a bond linking the released moiety to the remainder of the conjugate. Such cleavage is either chemical in nature, or enzymatically mediated. Exemplary enzymatically cleavable groups include natural amino acids or peptide sequences that end with a natural amino acid.

In addition to enzymatically cleavable groups, it is within the scope of the present invention to include one or more sites that are cleaved by the action of an agent other than an enzyme. Exemplary non-enzymatic cleavage agents include, but are not limited to, acids, bases, light (e.g., nitrobenzyl derivatives, phenacyl groups, benzoin esters), and heat. Many cleaveable groups are known in the art. See, for example, Jung et al., *Biochem. Biophys. Acta,* 761: 152-162 (1983); Joshi et al., *J. Biol. Chem.,* 265: 14518-14525 (1990); Zarling et al., *J. Immunol.,* 124: 913-920 (1980); Bouizar et al., *Eur. J. Biochem.,* 155: 141-147 (1986); Park et al., *J. Biol. Chem.,* 261: 205-210 (1986); Browning et al., *J. Immunol.,* 143: 1859-1867 (1989). Moreover a broad range of cleavable, bifunctional (both homo- and hetero-bifunctional) spacer arms are commercially available.

An exemplary cleavable group, an ester, is cleavable group that may be cleaved by a reagent, e.g. sodium hydroxide, resulting in a carboxylate-containing fragment and a hydroxyl-containing product.

The linker can be used to attach the compound to another component of a conjugate, such as a targeting moiety (e.g., antibody, ligand, non-covalent protein-binding group, etc.), an analyte, a biomolecule, a drug and the like.

The term "metal chelator" or "metal chelating moiety" as used herein refers to a chemical compound that combines with a metal ion to form a chelate ring structure. For the purposes of the present invention the metal chelator is an analog of BAPTA that has demonstrated affinity for lead, mercury, nickel, lanthanum, and cadmium. These ions may be free in solution or they may be sequestered by a metal ion-binding compound. The metal chelators are optionally substituted by substituents that adjust the ion-binding affinity, solubility, chemical reactivity, spectral properties or other physical properties of the compound.

The term "metal ion" as used herein refers to any physiological, environmental and or nutritional relevant metal ion. Such metal ions include certain transition metal ions and lanthanide metal ions, such as, but are not limited to lead, mercury, nickel, lanthanum and cadmium.

The terms "protein" and "polypeptide" are used herein in a generic sense to include polymers of amino acid residues of any length. The term "peptide" is used herein to refer to polypeptides having less than 250 amino acid residues, typically less than 100 amino acid residues, more typically less than 15 amino acid residues. The terms apply to amino acid polymers in which one or more amino acid residues are an artificial chemical analogue of a corresponding naturally occurring amino acid, as well as to naturally occurring amino acid polymers. The peptide or protein may be further conjugated to or complexed with other moieties such as dyes, haptens, radioactive isotopes, natural and synthetic polymers (including microspheres), glass, metals and metallic particles, proteins and nucleic acids.

The term "reactive group" as used herein refers to a group that is capable of reacting with another chemical group to form a covalent bond, i.e. is covalently reactive under suitable reaction conditions, and generally represents a point of attachment for another substance. The reactive group is a moiety, such as a photoactivatable group, carboxylic acid or succinimidyl ester, on the compounds of the present invention that is capable of chemically reacting with a functional group on a different compound to form a covalent linkage resulting in a phosphate-binding labeled component. Reactive groups generally include nucleophiles, electrophiles and photoactivatable groups.

Exemplary reactive groups include, but not limited to, olefins, acetylenes, alcohols, phenols, ethers, oxides, halides, aldehydes, ketones, carboxylic acids, esters, amides, cyanates, isocyanates, thiocyanates, isothiocyanates, amines, hydrazines, hydrazones, hydrazides, diazo, diazonium, nitro, nitriles, mercaptans, sulfides, disulfides, sulfoxides, sulfones, sulfonic acids, sulfinic acids, acetals, ketals, anhydrides, sulfates, sulfenic acids isonitriles, amidines, imides, imidates, nitrones, hydroxylamines, oximes, hydroxamic acids thiohydroxamic acids, allenes, ortho esters, sulfites, enamines, ynamines, ureas, pseudoureas, semicarbazides, carbodiimides, carbamates, imines, azides, azo compounds, azoxy compounds, and nitroso compounds. Reactive functional groups also include those used to prepare bioconjugates, e.g., N-hydroxysuccinimide esters, maleimides and the like. Methods to prepare each of these functional groups are well known in the art and their application to or modification for a particular purpose is within the ability of one of skill in the art (see, for example, Sandler and Karo, eds. ORGANIC FUNCTIONAL GROUP PREPARATIONS, Academic Press, San Diego, 1989).

The term "reporter molecule" as used herein refers to a moiety that is used to facilitate detection of metal ions in combination with the metal-chelating moiety of the present invention. Illustrative reporter molecules include molecules that can be directly observed or measured or indirectly observed or measured such as fluorophores, radioactive, haptens, fluorescent proteins and enzyme reporter molecules (Patton, W., et al, *J. Chromatography B: Biomedical Applications* (2002) 771:3-31; Patton, W., et al, *Electrophoresis* (2000) 21:1123-1144). Such reporter molecules include, but are not limited to, radiolabels that can be measured with radiation-counting devices; pigments, dyes (fluorophore or chromophore) or other chromogens that can be visually observed or measured with a spectrophotometer; tandem dyes that participate in energy transfer, spin labels that can be measured with a spin label analyzer; and fluorescent proteins or fluorophores, where the output signal is generated by the excitation of a suitable molecular adduct and that can be visualized by excitation with light that is absorbed by the dye or can be measured with standard fluorometers or imaging systems, for example or metal particles, e.g. gold or silver particles or metallic bar codes that can be detected by their optical or light-scattering properties. The reporter molecule can be a chemiluminescent substance, where the output signal is generated by chemical modification of the signal compound; a metal-containing substance; or an enzyme, where there occurs an enzyme-dependent secondary generation of signal, such as the formation of a colored product from a colorless substrate. The term reporter molecule can also refer to a "tag", hapten or other ligand that can bind selectively to a labeled molecule such that the labeled molecule, when added subsequently, is used to generate a detectable signal. For example, one can use biotin as a tag and then use an avidin or streptavidin conjugate of horseradish peroxidase (HRP) to bind to the tag, and then use a chromogenic substrate (e.g., tetramethylbenzidine) or a fluorogenic substrate such as Amplex® Red reagent (Molecular Probes, Inc.) to detect the presence of HRP. Numerous reporter molecules and tags and methods for their selective detection are known by those of skill in the art and include, but are not limited to, particles, fluorophores, haptens, enzymes and their chromogenic, fluorogenic and chemiluminescent substrates and other labels that are described in the MOLECULAR PROBES HANDBOOK, supra. In addition, present reporter molecules can be substituted with substituents that alter the ion-binding affinity of the present compound, solubility, chemical reactivity, spectral properties or other physical properties of the reporter molecule.

The term "sample" as used herein refers to any material that may contain metal ions, as defined above. Typically, the sample is a live cell or a biological fluid that comprises endogenous host cell proteins or foodstuff or an environmental sample such as a water sample. The sample may be in an aqueous solution, a viable cell culture or immobilized on a solid or semi solid surface such as a polyacrylamide gel, membrane blot or on a microarray.

The term "metal ion reporter molecule" or "present compound" as used herein refers to the metal chelating moiety that is an analog of BAPTA.

These compounds are typically substituted by substituents that modify ion affinity, chemical reactivity, spectral properties and solubility. Typically, the present compound is substituted by a reporter molecule, reactive group, solid support or carrier molecule that facilitate binding, detection, isolation, sequestration, and monitoring of the present metal ions. Preferably, the present compounds are substituted by reporter molecules that facilitate detection and monitoring of the metal ions. Thus, the metal ion reporter compounds of the present invention typically have the general formula A(B) wherein A is a reporter molecule, reactive group or carrier molecule, B is a metal chelating moiety. The reporter molecule may share atoms of the chelating moiety, be attached by a single covalent bond or attached by a linker comprising multiple stable bonds. Reactive groups and carrier molecules are attached by a single covalent bond or by a linker comprising multiple stable bonds. Thus, when these substituents are attached by a single covalent bond or a series of stable bonds the metal ion binding compound has the general formula A(L)m(B) wherein L is a Linker that covalently attaches the substituents to the metal chelating moiety and m is 0-4. The metal ions, such as lead and cadmium ions can be free in solutions or non-covalently bound to another molecule such as a protein.

The Compounds

In general, for ease of understanding the present invention, the heavy metal-binding compounds and corresponding substituents will first be described in detail, followed by the many and varied methods in which the heavy metal-binding compounds and metal ions find uses, which is followed by exemplified methods of use and synthesis of certain novel compounds that are particularly advantageous for use with the methods of the present invention.

The present invention provides analogs of the metal ion chelator, BAPTA, that bind a wide range of metal cations including physiological relevant levels of metal cations such as lead, cadmium and mercury. These metal chelating compounds comprise substituents well known in the art including linkers, chemically reactive groups, carrier molecules, solid support and reporter groups.

The present compounds find utility in binding target metal ions in a sample. The sample includes live cells or a biological fluid that comprises endogenous host cell proteins, buffer solutions and environmental samples. Therefore, when the present metal ion-binding compound comprises a reporter molecule they find utility in quantitating, monitoring and detecting target metal ions. These compounds are herein referred to as metal ion reporter molecules. Typically, the reporter molecule is directly attached to the benzo moiety or two of the benzo substituents when taken in combination form a fused reporter molecule. Detection of target metal ions can also be accomplished in live cells wherein the present compound comprises a lipophilic group such as an AM or acetate ester that allows for entry across the live cell membrane. Once inside the cells nonspecific esterases cleave the AM or acetate ester resulting a charged molecule that is well retained in the cell. These present compounds are particularly useful for binding physiological relevant levels of lead, cadmium and mercury ions.

Chelating Moiety

The metal chelating moiety of the present invention is a derivative of the well known calcium chelating moiety 1,2-bis(2-aminophenoxy)ethane-N,N,N',N'-tetraacetic acid (BAPTA). In an effort to devise a lead, cadmium, nickel, and/or mercury probe that is selective for physiologically relevant levels of these ions but not calcium ions, which are typically present in much higher concentrations, we unexpectedly found that by replacing one of the nitrogen atoms with oxygen, resulting in a triacetic BAPTA analog, that the new compound could selectively detect physiological levels of lead, cadmium and mercury, but not calcium ions. The modification to the BAPTA chelating moiety reduced the affinity for calcium ions by approximately 100-1000× fold but not the affinity for lead ions resulting in a chelator that preferentially binds lead ions in the presence of physiological concentrations of calcium ions. This metal chelating moiety is a —N,N,O-triacetic acid analog of BAPTA and has the following formula:

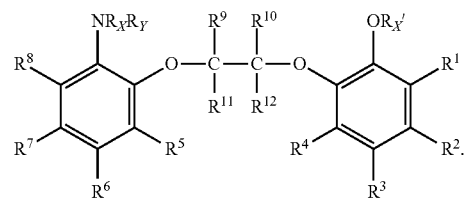

$R_X$, $R_Y$, and $R_{X'}$ are independently hydrogen, acetic acid or an acetic acid group that has been substituted by an acetyloxy methyl (AM) ester wherein acetic acid is represented by —$CR^{13}R^{14}CO_2R$ wherein R is hydrogen, a salt ion or an AM ester represented by —$CH_2OC(O)(CH_2)_nCH_3$ and n is 0 to 6. $R^{13}$ and $R^{14}$ are independently hydrogen, alkyl or substituted alkyl. In one aspect, $R^{13}$ and $R^{14}$ are each hydrogen wherein $R_X$, $R_Y$, and $R_{X'}$ are independently —$CH_2CO_2R$. In a further aspect, R is —$CH_2OC(O)(CH_2)_nCH_3$, wherein n is typically 0.

In an exemplary embodiment, modification of carboxylic groups with acetoxymethyl (AM) ester groups results in uncharged molecules than can penetrate cell membranes—live cell versions of the heavy metal-binding compounds. This includes the carboxylic groups of the acetic acid groups or other carboxylic groups on the metal chelating moiety. In this particular embodiment, typically at least one R is —$CH_2OC(O)CH_3$, preferably at least two R and most preferred at least three R are $CH_2OC(O)CH_3$. Once inside the cells, the lipophilic blocking groups are cleaved by nonspecific esterases revealing a metal chelating moiety of the present invention, e.g., a triacetic acid moiety. Alternatively, acetate groups on a compound of the present invention can also allow a compound to enter a live cell.

In another embodiment, R is H or a salt ion and the heavy metal-binding compounds of the present invention are used to bind and detect heavy metal ions that are not contained by a lipid bilayer. This includes heavy metal ions that are free in solution such as a biological fluid or heavy metal ions that have been released from cells and metal ions present in water samples, environmental samples, food stuff, etc. When R is H or a salt ion the compounds are impermeant to cellular membranes.

The present heavy metal binding compound comprises two benzene rings that are joined by a $C_1$-$C_3$ hydrocarbon bridge (n is 1, 2 or 3) terminated by oxygen atoms, including methylenedioxy (—OCH$_2$O—), ethylenedioxy (—OCH$_2$CH$_2$O—) or propylenedioxy (—OCH$_2$CH$_2$CH$_2$O—) bridging groups, where each benzene ring is optionally substituted by one or more substituents that adjust the metal ion-binding affinity, solubility, chemical reactivity, spectral properties or other physical properties of the compound. The benzene ring substituents ($R^1$, $R^2$, $R^3$, $R^4$, $R^5$, $R^6$, $R^7$ and $R^8$) and the bridging group substituents ($R^9$, $R^{10}$, $R^{11}$ and $R^{12}$) are typically selected from substituents that are found on BAPTA compounds. This includes any substituents disclosed in U.S. Pat. Nos. 4,603,209; 4,795,712; 4,849,362; 5,049,673; 5,453,517; 5,459,276; 5,516,911; 5,501,980; 6,162,931 and 5,773,227.

In an exemplary embodiment, $R^1$, $R^2$, $R^3$, $R^4$, $R^5$, $R^6$, $R^7$ and $R^8$ are independently selected from the group consisting of hydrogen, halogen, alkyl, substituted alkyl, alkoxy, substituted alkoxy, hydroxyl, aryl, substituted aryl, heteroaryl, substituted heteroaryl, amino, substituted amino, alkylamino, substituted alkylamino, aldehyde, carboxyl, azido, nitro, nitroso, cyano, thioether, sulfoalkyl, carboxyalkyl, aminoalkyl, reporter molecule, reactive group, carrier molecule or solid support. Each substituted amino substituent is independently substituted by hydrogen, $C_1$-$C_6$ alkyl, substituted alkyl, $C_1$-$C_6$ carboxyalkyl, an alpha-acyloxyalkyl, a biologically compatible salt, aryl, substituted aryl, aryl alkyl, substituted aryl alkyl, heteroaryl, and substituted heteroaryl. Each alkyl portion is optionally substituted by halogen, amino, hydroxy, or amino.

Alternatively, any two adjacent substituents $R^1$-$R^8$, taken in combination, form a fused ring moiety or reporter molecule. Specifically a member selected from $R^1$ in combination with $R^2$; $R^2$ in combination with $R^3$; $R^3$ in combination with $R^4$; $R^5$ in combination with $R^6$; $R^6$ in combination with $R^7$; and $R^7$ in combination with $R^8$; together with the atoms to which they are joined, form a ring which is a 5-, 6- or 7-membered heterocycloalkyl, a substituted 5-, 6- or 7-membered heterocycloalkyl, a 5-, 6- or 7-membered cycloalkyl, a substituted 5-, 6- or 7-membered cycloalkyl, a 5-, 6- or 7-membered heteroaryl, a substituted 5-, 6- or 7-membered heteroaryl, a 5-, 6- or 7-membered aryl, a substituted 5-, 6- or 7-membered aryl or reporter molecule. The ring moieties may be independently substituted by halogen, azido, nitro, nitroso, amino, cyano, $C_1$-$C_6$ alkyl or $C_1$-$C_6$ alkoxy. Each alkyl portion is optionally substituted by halogen, amino, hydroxy, or amino.

In an exemplary embodiment, at least one of $R^1$, $R^2$, $R^3$, $R^4$, $R^5$, $R^6$, $R^7$ and $R^8$ is a carrier molecule, solid support, reactive group or reporter molecule. Typically, at least one of $R^3$ or $R^6$ is a carrier molecule, solid support, reactive group or reporter molecule.

The bridging group substituents, $R^9$, $R^{10}$, $R^{11}$ and $R^{12}$, are typically independently selected from the group consisting of hydrogen, alkyl, carrier molecule, solid support, reactive group and reporter molecule. Alternatively, adjacent substituents $R^9$ in combination with $R^{10}$ or $R^{11}$ in combination with $R^{12}$ together with the atoms to which they are joined, form a ring which is a 5-, 6- or 7-membered heterocycloalkyl, a substituted 5-, 6- or 7-membered heterocycloalkyl, a 5-, 6- or 7-membered cycloalkyl, a substituted 5-, 6- or 7-membered cycloalkyl, a 5-, 6- or 7-membered heteroaryl, a substituted 5-, 6- or 7-membered heteroaryl, a 5-, 6- or 7-membered aryl, or a substituted 5-, 6- or 7-membered aryl.

In an exemplary embodiment each of $R_X$, $R_Y$, and $R_X{'}$ are hydrogen. In another embodiment at least one of $R_X$, $R_Y$, and $R_X{'}$ is CH$_2$CO$_2$R. In one aspect R is hydrogen or a salt ion, in another aspect R is CH$_2$OC(O)CH$_3$.

In an exemplary embodiment, the present compounds further comprise a reporter group to form a heavy metal indicator compound. These compounds are particularly useful for detecting lead, cadmium and/or mercury ions. In one aspect the present compounds comprise exactly one reporter group, which include, but are not limited to, chromophore, fluorophore, fluorescent protein, phosphorescent dye or a tandem dye. In a further aspect, the reporter molecule is a chromophore or fluorophore that is a xanthene, indole, cyanine, oxazole, dansyl, borapolyazaindacene, benzofuran, quinazolinone, benzazole, oxazine, pyrene, naphthalene, coumarin, biotin, enzyme substrate or fluorescent protein. Xanthenes include fluorescein or derivative thereof, rhodamine or derivative thereof, rhodol or derivative thereof or rosamine or a derivative thereof. These reporter molecules may also be substituted with substituents, including, but not limited to hydrogen, halogen, amino, substituted amino, alkyl, substituted alkyl, aryl, substituted aryl, heteroaryl, substituted heteroaryl, alkoxy, sulfo, a lipophilic group (Am ester or acetate ester), solid support, reactive group or carrier molecule.

Thus, an exemplary embodiment, the present compounds further comprises a carrier molecule. Carrier molecules include, but are not limited to, an amino acid, a peptide, a protein, a polysaccharide, a nucleoside, a nucleotide, an oligonucleotide, a nucleic acid polymer, a hapten, a psoralen, a drug, a hormone, a lipid, a lipid assembly, a synthetic polymer, a polymeric microparticle, a biological cell or a virus. In a further aspect, the carrier molecule is an antibody or fragment thereof, an avidin or streptavidin, a biotin, a blood component protein, a dextran, an enzyme, an enzyme inhibitor, a hormone, an IgG binding protein, a fluorescent protein, a growth factor, a lectin, a lipopolysaccharide, a microorganism, a metal binding protein, a metal chelating moiety, a non-biological microparticle, a peptide toxin, a phosphotidylserine-binding protein, a structural protein, a small-molecule drug, or a tyramide.

In yet another embodiment, the present compounds further comprise a solid support. Solid supports include, but are not limited to, a microfluidic chip, a silicon chip, a microscope slide, a microplate well, silica gels, polymeric membranes, particles, derivatized plastic films, glass beads, cotton, plastic beads, alumina gels, polysaccharides, polyvinylchloride, polypropylene, polyethylene, nylon, latex bead, magnetic bead, paramagnetic bead, or superparamagnetic bead. In one aspect, the solid support is sepharose, poly(acrylate), polystyrene, poly(acrylamide), polyol, agarose, agar, cellulose, dextran, starch, FICOLL, heparin, glycogen, amylopectin, mannan, inulin, nitrocellulose, diazocellulose or starch In an exemplary embodiment, the present compounds further comprise a solid support and a reporter group, which are particularly useful for high content screening.

In another embodiment, the present compounds comprise a reactive group. Reactive groups include, but are not limited to, an acrylamide, an activated ester of a carboxylic acid, a carboxylic ester, an acyl azide, an acyl nitrile, an aldehyde, an alkyl halide, an anhydride, an aniline, an amine, an aryl halide, an azide, an aziridine, a boronate, a diazoalkane, a haloacetamide, a haloalkyl, a halotriazine, a hydrazine, an imido ester, an isocyanate, an isothiocyanate, a maleimide, a phosphoramidite, a reactive platinum complex, a silyl halide, a sulfonyl halide, a thiol or a photoactivatable group. In one aspect, the reactive group is carboxylic acid, succinimidyl ester of a carboxylic acid, hydrazide, amine or a maleimide.

In an exemplary embodiment, the present compounds are according to the formula:

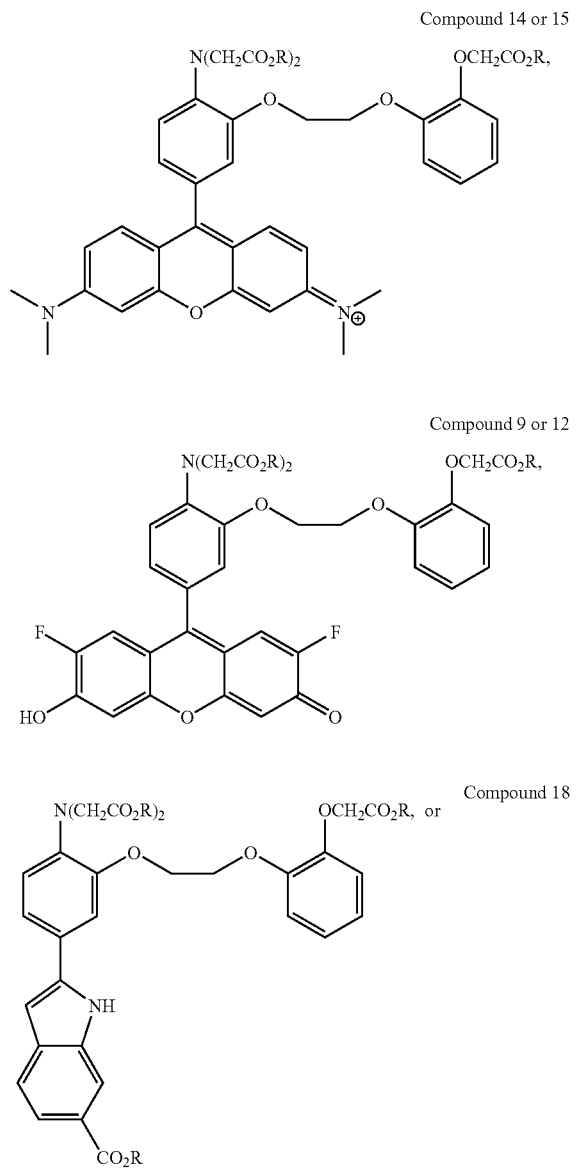

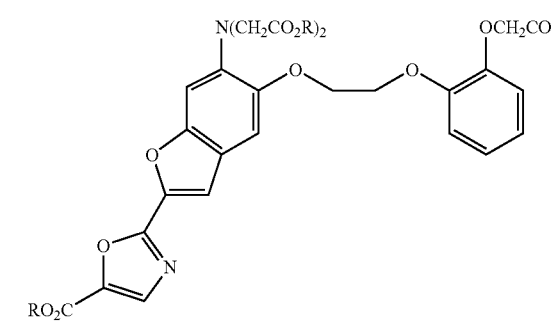

with a biologically compatible anion wherein R is hydrogen, a salt ion or an AM ester represented by —CH$_2$OC(O)(CH$_2$)$_n$CH$_3$.

Synthesis

The general synthesis method involves joining a 2-nitrophenol derivative with a catechol derivative via an ethylene bridge, followed by reduction of the nitro group to an amine to give representative compound A. Chelating moieties are then added to the aniline nitrogen and phenolic oxygen groups by reaction with electorophilic acetic acid esters, for example to give representative compound B. Formylation of B affords C, which provides a reactive handle for attachment of fluorescent moieties. For example, in this case acid-mediated condensation of C with 4-fluororesorcinol, followed by dehydrogenative oxidation, gives the fluorophore D in which the chelating acetic acid residues are still protected as esters. These esters can be cleaved by alkaline or acidic hydrolysis to give metal ion-binding chelator E, in which the fluorescence is modulated by binding of certain transition metal or heavy metal ions. The carboxylates in E can be further derivatized into other kinds of esters which facilitate the molecule's entry into live cells or hydrophobic environments. Properly chosen, these esters will be spontaneously hydrolyzed back to the free carboxylate form as in D, for example trapping D in live cells so as to provide fluorescence reporting on the concentration of certain heavy metal or transition metal ions.

Additionally, compounds such as B can be nitrated and then the nitro group reduced so as to introduce an aniline moiety onto an aromatic ring. This aniline moiety can be used as a reactive handle for attachment of fluorophores or other optical reporting agents such that binding of certain transition or heavy metal ions after cleavage of the acetic acid esters results in fluorescence changes.

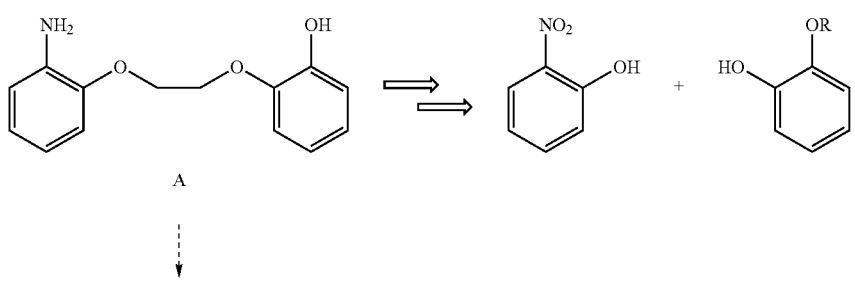

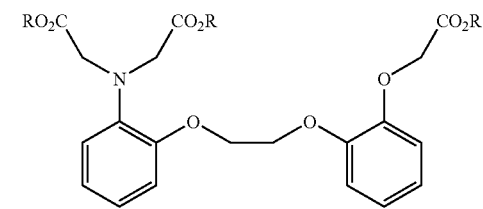

B

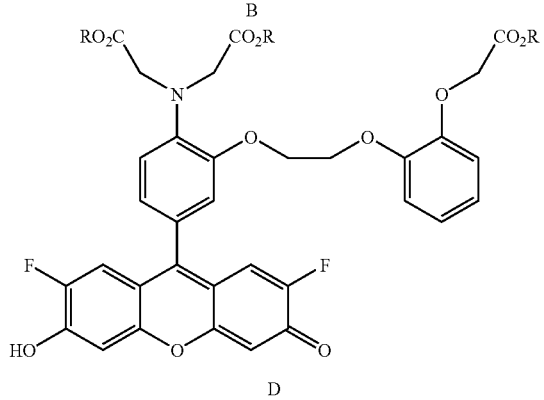

D

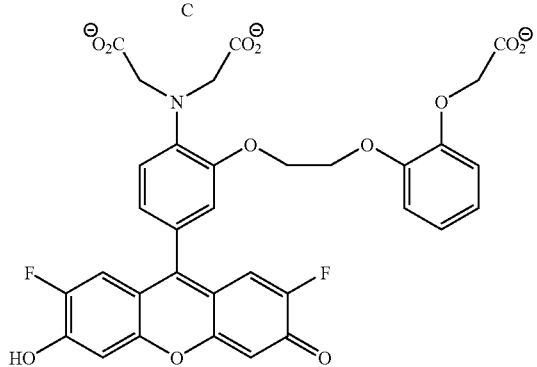

C

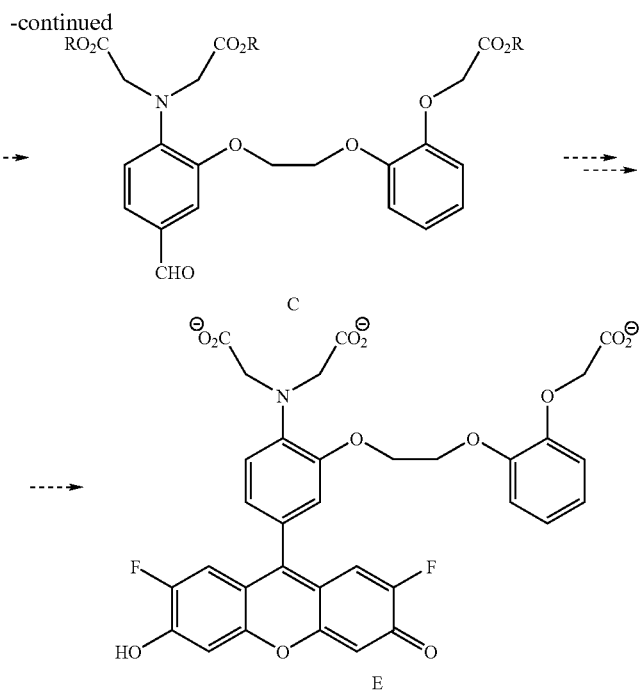

E

Reporter Molecules

In an exemplary embodiment, the present compounds confer a detectable signal, directly or indirectly, to the metal ions, wherein they are covalently bonded to a reporter molecule. This results in the ability to detect, monitor and quantitate heavy metal ions in a sample.

Thus, in an exemplary embodiment, the present compound is covalently bound to a reporter group, See Compound 10, 12 and 18. The reporter molecule can be attached to the compound through the chelating moiety by a linker or share atoms with the chelating moiety wherein no linker is present (See, Compound 20). If the compound has a reactive group, then the reporter molecule can alternatively be linked to the compound through the reactive group. The reactive group may contain both a reactive functional moiety and a linker, or only the reactive functional moiety.

The present reporter molecules can be any reporter molecule known to one skilled in the art and when the reporter molecule is either covalently linked to a metal-chelating moiety or comprises part of the metal-chelating moiety wherein no linker is present, forms a metal ion binding compound of the present invention that is useful for the detection of lead, mercury and/or cadmium ions. Reporter molecules include, without limitation, a dye, (chromophore or fluorophore), a fluorescent protein, a phosphorescent dye, a tandem dye (energy transfer pair), a microparticle, a hapten, an enzyme and a radioisotope. Preferred reporter molecules include dyes (both chromophores and fluorophores), fluorescent proteins, haptens, and enzymes. When the reporter molecule is a chromophore the heavy metal-binding compounds are chromogenic indicators, or more preferably, the reporter molecule is a fluorophore, resulting in a compound that is a fluorogenic indicator for heavy metal ions. Therefore, binding a heavy metal ion to a heavy metal-binding compound results in a detectable optical response that can be correlated to the presence of lead, cadmium and/or mercury ions.

In one embodiment, at least one of $R^1$, $R^2$, $R^3$, $R^4$, $R^5$, $R^6$, $R^7$, and $R^8$ is or is attached to a reporter molecule or any two adjacent $R^1$, $R^2$, $R^3$, $R^4$, $R^5$, $R^6$, $R^7$, and $R^8$ form a fused reporter molecule that share atoms with either ring of the present chelating moiety. In a particular aspect at least one of $R^2$, $R^3$, $R^6$, and $R^7$, is or is attached to a reporter molecule. In a preferred aspect, either $R^3$ or $R^6$ is or is attached to a reporter molecule.

Where the detectable response is a fluorescence response, it is typically a change in fluorescence, such as a change in the intensity, excitation or emission wavelength, distribution of fluorescence, fluorescence lifetime, fluorescence polarization, or a combination thereof. Preferably, the detectable optical response upon binding a target heavy metal ion is a change in fluorescence intensity that is greater than approximately 10-fold relative to the same compound in the absence of heavy metal ions, more preferably greater than 50-fold, and most preferably more that 100-fold. This large increase in fluorescent signal over baseline has not been previously observed with other heavy metal indicators that comprise a different metal chelating moiety. Other well known heavy metal indicators such as Phen Green (Invitrogen Corp.) indicate metal binding by fluorescence decreases. In another aspect, the detectable optical response upon binding the target metal ion is a shift in either the maximal excitation or emission wavelength or both that is greater than about 20 nm, more preferably greater than about 30 nm.

A dye of the present invention is any chemical moiety that exhibits an absorption maximum beyond 280 nm, and when covalently linked to a metal chelating moiety of the present invention, or shares atoms with the metal chelating moiety, forms a heavy metal-binding compound. A preferred embodiment for detecting heavy metal ions in live cells or heavy metal ions secreted from live cells is a fluorogenic heavy metal-binding compound wherein the reporter molecule is dye. As described below in more detail, the covalent linkage can be a single covalent bond or a combination of stable chemical bonds. The covalent linkage binding the dye to the metal chelating moiety is typically a single covalent bond or a substituted alkyl chain that incorporates 1-20 nonhydrogen atoms selected from the group consisting of C, N, O, S and P.

Dyes of the present invention include, without limitation; a pyrene, an anthracene, a naphthalene, an acridine, a stilbene, an indole or benzindole, an oxazole or benzoxazole, a thiazole or benzothiazole, a 4-amino-7-nitrobenz-2-oxa-1,3-diazole (NBD), a carbocyanine (including any corresponding compounds in U.S. Ser. Nos. 09/557,275; 09/968,401 and 09/969,853 and U.S. Pat. Nos. 6,403,807; 6,348,599; 5,486,616; 5,268,486; 5,569,587; 5,569,766; 5,627,027; 6,048,982 and 6,664,047), a carbostyryl, a porphyrin, a salicylate, an anthranilate, an azulene, a perylene, a pyridine, a quinoline, a borapolyazaindacene (including any corresponding compounds disclosed in U.S. Pat. Nos. 4,774,339; 5,187,288; 5,248,782; 5,274,113; and 5,433,896), a xanthene (including any corresponding compounds disclosed in U.S. Pat. No. 6,162,931; 6,130,101; 6,229,055; 6,339,392; 5,451,343 and U.S. Ser. No. 09/922,333), an oxazine or a benzoxazine, a carbazine (including any corresponding compounds disclosed in U.S. Pat. No. 4,810,636), a phenalenone, a coumarin (including an corresponding compounds disclosed in U.S. Pat. Nos. 5,696,157; 5,459,276; 5,501,980 and 5,830,912), a benzofuran (including an corresponding compounds disclosed in U.S. Pat. Nos. 4,603,209 and 4,849,362) and benzphenalenone (including any corresponding compounds disclosed in U.S. Pat. No. 4,812,409) and derivatives thereof. As used herein, oxazines include resorufins (including any corresponding compounds disclosed in U.S. Pat. No. 5,242,805), aminooxazinones, diaminooxazines, and their benzo-substituted analogs.

Where the dye is a xanthene, the dye is optionally a fluorescein, a rhodol (including any corresponding compounds disclosed in U.S. Pat. Nos. 5,227,487 and 5,442,045), a rosamine or a rhodamine (including any corresponding compounds in U.S. Pat. Nos. 5,798,276; 5,846,737; 5,847,162; 6,017,712; 6,025,505; 6,080,852; 6,716,979; 6,562,632). As used herein, fluorescein includes benzo- or dibenzofluoresceins, seminaphthofluoresceins, or naphthofluoresceins. Similarly, as used herein rhodol includes seminaphthorhodafluors (including any corresponding compounds disclosed in U.S. Pat. No. 4,945,171).

Preferred dyes of the invention include rhodol, fluorescein, rhodamine, dansyl, benzofuran, indole, cyanine, quinazolinone, pyrene, naphthalene, coumarin, oxazine, oxazole, benzofuran, indole, a benzazole and borapolyazaindacene. In one embodiment benzofuran and benzazole form a fused reporter molecule with either benzo ring the chelating moiety. In another aspect, the reporter molecules xanthene, dansyl, benzofuran, indole, cyanine, quinazolinone, pyrene, naphthalene, coumarin, oxazine, indole, and borapolyazaindacene are independently attached to the chelating moiety by a linker.

In an exemplary embodiment, the dye contains one or more aromatic or heteroaromatic rings, that are optionally substituted one or more times by a variety of substituents, including without limitation, hydrogen, amino, substituted amino, halogen, nitro, sulfo, cyano, alkyl, substituted alkyl, perfluoroalkyl, alkoxy, alkenyl, alkynyl, cycloalkyl, arylalkyl, acyl, aryl or heteroaryl ring system, substituted aryl, benzo, solid support, reactive group, carrier molecule, lipophilic group, or other substituents typically present on chromophores or fluorophores known in the art.

In one aspect, the dyes are independently substituted by substituents selected from the group consisting of hydrogen, halogen, amino, substituted amino, alkyl, substituted alkyl, aryl, substituted aryl, heteroaryl, substituted heteroaryl, alkoxy, sulfo, reactive group, solid support, lipophilic group, and carrier molecule. In another embodiment, the xanthene dyes of this invention comprise both compounds substituted and unsubstituted on the carbon atom of the central ring of the xanthene by substituents typically found in the xanthene-based dyes such as phenyl and substituted-phenyl moieties. Most preferred dyes are rhodamine, fluorescein, rhodal, rosamine and derivatives thereof. The choice of the dye attached to the chelating moiety will determine the heavy metal-binding compound's absorption and fluorescence emission properties.

In an exemplary embodiment, the dye has an absorption maximum beyond 480 nm. In a particularly useful embodiment, the dye absorbs at or near 488 nm to 514 nm (particularly suitable for excitation by the output of the argon-ion laser excitation source) or near 546 nm (particularly suitable for excitation by a mercury arc lamp). As is the case for many dyes, they can also function as both chromophores and fluorophores, resulting in compounds that simultaneously act both as colorimetric and fluorescent labels for heavy metal ions. Thus, the described fluorescent dyes are also the preferred chromophores of the present invention.

For heavy metal-binding compounds that find use in detecting heavy metal ions wherein a change in detectable signal is not required, i.e. unbound heavy metal-binding compounds can be washed away and the remaining heavy metal-binding compounds are bound to heavy metal ions, the alternative reporter molecules that are haptens, enzymes, fluorescent proteins and tandem dyes (energy transfer dyes) find use as reporter molecules of the present invention. In this aspect, a stable ternary complex is formed between a heavy metal ion and a heavy metal-binding molecule (e.g., protein, carrier molecule or solid support). Therefore, these reporter molecules find use wherein the sample is immobilized on a solid or semi-solid matrix or in biological fluids wherein a polarization assay is used to measure heavy metal ions or alternatively tandem dyes can be used resulting in a shift in signal when heavy metal ions are bound by the heavy metal-binding compounds.

Enzymes are desirable reporter molecules because amplification of the detectable signal can be obtained, resulting in increased assay sensitivity. The enzyme itself does not produce a detectable response, but functions to break down a substrate when it is contacted by an appropriate substrate such that the converted substrate produces a fluorescent, colorimetric or luminescent signal. Enzymes amplify the detectable signal because one enzyme on a heavy metal-binding compound can result in multiple substrate molecules being converted to a detectable signal. This is advantageous where there is a low quantity of heavy metal ions present in the sample or a dye does not exist that will give comparable or stronger signal than the enzyme. Dyes are most preferred because they do not require additional assay steps that can lead to an unstable heavy metal-binding complex and they do not lend to live cell measurement of heavy metal ions. The enzyme substrate is selected to yield the preferred measurable product, e.g. color, fluorescence or chemiluminescence. Such substrates are extensively used in the art, many of which are described in the MOLECULAR PROBES HANDBOOK, supra.

A preferred colorimetric or fluorogenic substrate and enzyme combination uses oxidoreductases such as horseradish peroxidase (HRP) and a substrate such as 3,3'-diaminobenzidine (DAB) or 3-amino-9-ethylcarbazole (AEC), which yield a distinguishing color (brown and red, respectively). Other colorimetric oxidoreductase substrates that yield detectable products include, but are not limited to: 2,2-azino-bis(3-ethylbenzothiazoline-6-sulfonic acid) (ABTS), o-phenylenediamine (OPD), 3,3',5,5'-tetramethylbenzidine (TMB), o-dianisidine, 5-aminosalicylic acid and 4-chloro-1-naphthol. Fluorogenic substrates include, but are not limited to, homovanillic acid or 4-hydroxy-3-methoxyphenylacetic acid, reduced phenoxazines and reduced benzothiazines, including Amplex® Red reagent and its variants (U.S. Pat. No. 4,384,042) and reduced dihydroxanthenes, including dihydrofluoresceins (U.S. Pat. No. 6,162,931) and dihydrorhodamines, including dihydrorhodamine 123. Peroxidase substrates that are tyramides (U.S. Pat. Nos. 5,196,306; 5,583,001 and 5,731,158) represent a unique class of peroxidase substrates in that they can be intrinsically detectable before action of the enzyme but are "fixed in place" by the action of a peroxidase in the process described as tyramide signal amplification (TSA). These substrates are extensively utilized to label targets in samples that are cells, tissues or arrays for their subsequent detection by microscopy, flow cytometry, optical scanning and fluorometry.

Another preferred colorimetric (and in some cases fluorogenic) substrate and enzyme combination uses a phosphatase enzyme such as an acid phosphatase or a recombinant version of such a phosphatase in combination with a colorimetric substrate such as 5-bromo-4-chloro-3-indolyl phosphate (BCIP), 6-chloro-3-indolyl phosphate, 5-bromo-6-chloro-3-indolyl phosphate, p-nitrophenyl phosphate, or o-nitrophenyl phosphate or with a fluorogenic substrate such as 4-methylumbelliferyl phosphate, 6,8-difluoro-7-hydroxy-4-methylcoumarinyl phosphate (DiFMUP, U.S. Pat. No. 5,830,912), fluorescein diphosphate, 3-O-methylfluorescein phosphate, resorufin phosphate, 9H-(1,3-dichloro-9,9-dimethylacridin-2-one-7-yl) phosphate (DDAO phosphate), or ELF 97, ELF 39 or related phosphates (U.S. Pat. Nos. 5,316,906 and 5,443,986).

Glycosidases, in particular β-galactosidase, β-glucuronidase and β-glucosidase, are additional suitable enzymes. Appropriate colorimetric substrates include, but are not limited to, 5-bromo-4-chloro-3-indolyl β-D-galactopyranoside (X-gal) and similar indolyl galactosides, glucosides, and glucuronides, o-nitrophenyl β-D-galactopyranoside (ONPG) and p-nitrophenyl β-D-galactopyranoside. Preferred fluorogenic substrates include resorufin β-D-galactopyranoside, fluorescein digalactoside (FDG), fluorescein diglucuronide and their structural variants (U.S. Pat. Nos. 5,208,148; 5,242,805; 5,362,628; 5,576,424 and 5,773,236), 4-methylumbelliferyl β-D-galactopyranoside, carboxyumbelliferyl β-D-galactopyranoside and fluorinated coumarin β-D-galactopyranosides (U.S. Pat. No. 5,830,912).

Additional enzymes include, but are not limited to, hydrolases such as cholinesterases and peptidases, oxidases such as glucose oxidase and cytochrome oxidases and reductases for which suitable substrates are known.

Enzymes and their appropriate substrates that produce chemiluminescence are preferred for some assays. These include, but are not limited to, natural and recombinant forms of luciferases and aequorins. Chemiluminescence-producing substrates for phosphatases, glycosidases and oxidases such as those containing stable dioxetanes, luminol, isoluminol and acridinium esters are additionally useful. Several chemiluminescent substrates for phosphatase enzymes are known, including the BOLD APB chemiluminescent substrate (Molecular Probes, Inc.).

In addition to enzymes, haptens such as biotin, digoxigenin and 2,4-dinitrophenol are also preferred reporter molecules. Biotin is useful because it can function in an enzyme system to further amplify the detectable signal, and it can function as a tag to be used in affinity chromatography for isolation purposes. For detection purposes, an enzyme conjugate that has affinity for biotin is used, such as avidin-HRP. Subsequently a peroxidase substrate is added to produce a detectable signal. For isolation purposes, a protein such as avidin that has affinity for biotin is conjugated to agarose beads. The biotin labeled metal-chelating moiety, after contacting a target heavy metal ion, is then incubated with the avidin beads, on a column or in solution, to separate and/or concentrate the heavy metal ions. A preferred form of biotin is the desthiobiotin analog, which can be easily adsorbed and released from avidin-based affinity matrices. A preferred form of avidin for some applications is CaptAvidin biotin-binding protein (Molecular Probes), which permits facile release of biotinylated compounds.

Haptens also include, among other derivatives, hormones, naturally occurring and synthetic drugs, pollutants, allergens, affector molecules, growth factors, chemokines, cytokines, lymphokines, amino acids, peptides, chemical intermediates, nucleotides and the like.

Fluorescent proteins also find use as labels for the heavy metal-binding compounds of the present invention. Examples of fluorescent proteins include green fluorescent protein (GFP) and the phycobiliproteins and the derivatives thereof. The fluorescent proteins, especially phycobiliproteins, are particularly useful for creating tandem dye-reporter molecules or for indirect detection of hapten-labeled heavy metal-binding compounds or heavy metal-binding proteins that are immobilized on a matrix, such as a microsphere or an array. These tandem dyes comprise a fluorescent protein and a fluorophore for the purposes of obtaining a larger Stokes shift, wherein the emission spectra are farther shifted from the wavelength of the fluorescent protein's absorption spectra. This property is particularly advantageous for detecting a low quantity of a target heavy metal ion in a sample wherein the emitted fluorescent light is maximally optimized; in other words, little to none of the emitted light is reabsorbed by the fluorescent protein. For this to work, the fluorescent protein and fluorophore function as an energy transfer pair wherein the fluorescent protein emits at the wavelength that the acceptor fluorophore absorbs and the fluorophore then emits at a wavelength farther from the fluorescent proteins than could have been obtained with only the fluorescent protein. Alternatively, the fluorophore functions as the energy donor and the fluorescent protein is the energy acceptor. Particularly useful fluorescent proteins are the phycobiliproteins disclosed in U.S. Pat. Nos. 4,520,110; 4,859,582; 5,055,556 and the fluorophore bilin protein combinations disclosed in U.S. Pat. No. 4,542,104. Alternatively, two or more fluorophore dyes can function as an energy transfer pair wherein one fluorophore is a donor dye and the other is the acceptor dye including any dye compounds disclosed in U.S. Pat. Nos. 6,358,684; 5,863,727; 6,372,445; 6,221,606; 6,008,379; 5,945,526; 5,863,727; 5,800,996; 6,335,440; 6,008,373; 6,184,379; 6,140,494 and 5,656,554.

Reactive Groups, Carrier Molecules and Solid Supports

The present compounds, in certain embodiments, are chemically reactive wherein the compounds comprise a reactive group. In a further embodiment, the compounds comprise a carrier molecule or solid support. These substituents, reactive groups, carrier molecules, and solid supports, comprise a linker that is used to covalently attach the substituents to any of the moieties of the present compounds. The solid support, carrier molecule or reactive group may be directly attached (where linker is a single bond) to the moieties or attached through a series of stable bonds, as disclosed above.

Any combination of linkers may be used to attach the carrier molecule, solid support or reactive group and the present compounds together. This description of the linker also applies to the reporter molecules, as disclosed above. The linker may also be substituted to alter the physical properties of the reporter moiety or chelating moiety, such as spectral properties of the dye. Examples of L include substituted or unsubstituted polyalkylene, arylene, alkylarylene, arylenealkyl, or arylthio moieties.

The linker typically incorporates 1-30 nonhydrogen atoms selected from the group consisting of C, N, O, S and P. The linker may be any combination of stable chemical bonds, optionally including, single, double, triple or aromatic carbon-carbon bonds, as well as carbon-nitrogen bonds, nitrogen-nitrogen bonds, carbon-oxygen bonds, sulfur-sulfur bonds, carbon-sulfur bonds, phosphorus-oxygen bonds, phosphorus-nitrogen bonds, and nitrogen-platinum bonds. Typically the linker incorporates less than 15 nonhydrogen atoms and are composed of any combination of ether, thioether, thiourea, amine, ester, carboxamide, sulfonamide, hydrazide bonds and aromatic or heteroaromatic bonds. Typically the linker is a combination of single carbon-carbon bonds and carboxamide, sulfonamide or thioether bonds. The bonds of the linker typically result in the following moieties that can be found in the linker: ether, thioether, carboxamide, thiourea, sulfonamide, urea, urethane, hydrazine, alkyl, aryl, heteroaryl, alkoxy, cycloalkyl and amine moieties. Examples of a linker include substituted or unsubstituted polymethylene, arylene, alkylarylene, arylenealkyl, and arylthio.

In one embodiment, the linker contains 1-6 carbon atoms; in another, the linker comprises a thioether linkage. Exemplary linking members include a moiety that includes —C(O)NH—, —C(O)O—, —NH—, —S—, —O—, and the like. In another embodiment, the linker is or incorporates the formula —$(CH_2)_d(CONH(CH_2)_e)_z$— or where d is an integer from 0-5, e is an integer from 1-5 and z is 0 or 1. In a further embodiment, the linker is or incorporates the formula —O—$(CH_2)$—. In yet another embodiment, the linker is or incorporates a phenylene or a 2-carboxy-substituted phenylene.

An important feature of the linker is to provide an adequate space between the carrier molecule, reactive group or solid support and the dye so as to prevent steric hinderance. Therefore, the linker of the present compound is important for (1) attaching the carrier molecule, reactive group or solid support to the compound, (2) providing an adequate space between the carrier molecule, reactive group or solid support and the compound so as not to sterically hinder the action of the compound and (3) for altering the physical properties of the present compounds.

In another exemplary embodiment of the invention, the present compounds are chemically reactive, and are substituted by at least one reactive group. The reactive group functions as the site of attachment for another moiety, such as a carrier molecule or a solid support, wherein the reactive group chemically reacts with an appropriate reactive or functional group on the carrier molecule or solid support.

Reactive groups or reactive group precursors may be positioned during the formation of the present compounds. Thus, compounds incorporating a reactive group can be reacted with and attached to a wide variety of biomolecules or non-biomolecules that contain or are modified to contain functional groups with suitable reactivity. When a labeled component includes a compound as disclosed herein, then this conjugate typically possesses the nucleic acid staining abilities of the parent compound, particularly DNA staining. However, the present fluorescent compounds can also function as reporter molecules for the labeled components wherein the nucleic acid binding properties of the reagents may not employed.

Preferred reactive groups for incorporation into the disclosed compounds may be selected to react with an amine, a thiol or an alcohol. In an exemplary embodiment, the compounds of the invention further comprise a reactive group that is an acrylamide, an activated ester of a carboxylic acid, a carboxylic ester, an acyl azide, an acyl nitrile, an aldehyde, an alkyl halide, an anhydride, an aniline, an amine, an aryl halide, an azide, an aziridine, a boronate, a diazoalkane, a haloacetamide, a haloalkyl, a halotriazine, a hydrazine, an imido ester, an isocyanate, an isothiocyanate, a maleimide, a phosphoramidite, a photoactivatable group, a reactive platinum complex, a silyl halide, a sulfonyl halide, and a thiol. In a particular embodiment the reactive group is selected from the group consisting of carboxylic acid, succinimidyl ester of a carboxylic acid, hydrazide, amine and a maleimide. In exemplary embodiment, at least one member selected from $R^1$, $R^2$, $R^3$, $R^4$, $R^5$, $R^6$, $R^7$, $R^8$, $R^9$, $R^{10}$, $R^{11}$ or $R^{12}$ comprises a reactive group. Preferably, at least one of $R^1$, $R^2$, $R^3$, $R^4$, $R^5$, $R^6$, $R^7$, or $R^8$ comprises a reactive group or is attached to a reactive group. More preferred, at least one of $R^3$ or $R^6$ comprises a reactive group or is attached to a reactive group. Alternatively, if the present compound comprises a carrier molecule or solid support a reactive group may be covalently attached independently to those substituents, allowing for further conjugation to a another dye, carrier molecule or solid support.

In one aspect, the compound comprises at least one reactive group that selectively reacts with an amine group. This amine-reactive group is selected from the group consisting of succinimidyl ester, sulfonyl halide, tetrafluorophenyl ester and iosothiocyanates. Thus, in one aspect, the present compounds form a covalent bond with an amine-containing molecule in a sample. In another aspect, the compound comprises at least one reactive group that selectively reacts with a thiol group. This thiol-reactive group is selected from the group consisting of maleimide, haloalkyl and haloacetamide (including any reactive groups disclosed in U.S. Pat. Nos. 5,362,628; 5,352,803 and 5,573,904).

The pro-reactive groups are synthesized during the formation of the monomer moieties and carrier molecule and solid support containing compounds to provide chemically reactive compounds. In this way, compounds incorporating a reactive group can be covalently attached to a wide variety of carrier molecules or solid supports that contain or are modified to contain functional groups with suitable reactivity, resulting in chemical attachment of the components. In an exemplary embodiment, the reactive group of the compounds of the invention and the functional group of the carrier molecule or solid support comprise electrophiles and nucleophiles that can generate a covalent linkage between them. Alternatively, the reactive group comprises a photoactivatable group, which becomes chemically reactive only after illumination with light of an appropriate wavelength. Typically, the conjugation reaction between the reactive group and the carrier molecule or solid support results in one or more atoms of the reactive group being incorporated into a new linkage attaching the present compound of the invention to the carrier molecule or solid support. Selected examples of functional groups and linkages are shown in Table 1, where the reaction of an electrophilic group and a nucleophilic group yields a covalent linkage.

TABLE 1

Examples of some routes to useful covalent linkages

| Electrophilic Group | Nucleophilic Group | Resulting Covalent Linkage |
|---|---|---|
| activated esters* | amines/anilines | carboxamides |
| acrylamides | thiols | thioethers |
| acyl azides** | amines/anilines | carboxamides |

TABLE 1-continued

Examples of some routes to useful covalent linkages

| Electrophilic Group | Nucleophilic Group | Resulting Covalent Linkage |
|---|---|---|
| acyl halides | amines/anilines | carboxamides |
| acyl halides | alcohols/phenols | esters |
| acyl nitriles | alcohols/phenols | esters |
| acyl nitriles | amines/anilines | carboxamides |
| aldehydes | amines/anilines | imines |
| aldehydes or ketones | hydrazines | hydrazones |
| aldehydes or ketones | hydroxylamines | oximes |
| alkyl halides | amines/anilines | alkyl amines |
| alkyl halides | carboxylic acids | esters |
| alkyl halides | thiols | thioethers |
| alkyl halides | alcohols/phenols | ethers |
| alkyl sulfonates | thiols | thioethers |
| alkyl sulfonates | carboxylic acids | esters |
| alkyl sulfonates | alcohols/phenols | ethers |
| anhydrides | alcohols/phenols | esters |
| anhydrides | amines/anilines | carboxamides |
| aryl halides | thiols | thiophenols |
| aryl halides | amines | aryl amines |
| aziridines | thiols | thioethers |
| boronates | glycols | boronate esters |
| carbodiimides | carboxylic acids | N-acylureas or anhydrides |
| diazoalkanes | carboxylic acids | esters |
| epoxides | thiols | thioethers |
| haloacetamides | thiols | thioethers |
| haloplatinate | amino | platinum complex |
| haloplatinate | heterocycle | platinum complex |
| haloplatinate | thiol | platinum complex |
| halotriazines | amines/anilines | aminotriazines |
| halotriazines | alcohols/phenols | triazinyl ethers |
| halotriazines | thiols | triazinyl thioethers |
| imido esters | amines/anilines | amidines |
| isocyanates | amines/anilines | ureas |
| isocyanates | alcohols/phenols | urethanes |
| isothiocyanates | amines/anilines | thioureas |
| maleimides | thiols | thioethers |
| phosphoramidites | alcohols | phosphite esters |
| silyl halides | alcohols | silyl ethers |
| sulfonate esters | amines/anilines | alkyl amines |
| sulfonate esters | thiols | thioethers |
| sulfonate esters | carboxylic acids | esters |
| sulfonate esters | alcohols | ethers |
| sulfonyl halides | amines/anilines | sulfonamides |
| sulfonyl halides | phenols/alcohols | sulfonate esters |

*Activated esters, as understood in the art, generally have the formula —COΩ, where Ω is a good leaving group (e.g., succinimidyloxy (—OC$_4$H$_4$O$_2$) sulfosuccinimidyloxy (—OC$_4$H$_3$O$_2$—SO$_3$H), -1-oxybenzotriazolyl (—OC$_6$H$_4$N$_3$); or an aryloxy group or aryloxy substituted one or more times by electron withdrawing substituents such as nitro, fluoro, chloro, cyano, or trifluoromethyl, or combinations thereof, used to form activated aryl esters; or a carboxylic acid activated by a carbodiimide to form an anhydride or mixed anhydride —OCOR$^a$ or —OCNR$^a$NHR$^b$, where R$^a$ and R$^b$, which may be the same or different, are C$_1$-C$_6$ alkyl, C$_1$-C$_6$ perfluoroalkyl, or C$_1$-C$_6$ alkoxy; or cyclohexyl, 3-dimethylaminopropyl, or N-morpholinoethyl).
**Acyl azides can also rearrange to isocyanates Choice of the reactive group used to attach the compound of the invention to the substance to be conjugated typically depends on the reactive or functional group on the substance to be conjugated and the type or length of covalent linkage desired. The types of functional groups typically present on the organic or inorganic substances (biomolecule or non-biomolecule) include, but are not limited to, amines, amides, thiols, alcohols, phenols, aldehydes, ketones, phosphates, imidazoles, hydrazines, hydroxylamines, disubstituted amines, halides, epoxides, silyl halides, carboxylate esters, sulfonate esters, purines, pyrimidines, carboxylic acids, olefinic bonds, or a combination of these groups. A single type of reactive site may be available on the substance (typical for polysaccharides or silica), or a variety of sites may occur (e.g., amines, thiols, alcohols, phenols), as is typical for proteins.

Typically, the reactive group will react with an amine, a thiol, an alcohol, an aldehyde, a ketone, or with silica. Preferably, reactive groups react with an amine or a thiol functional group, or with silica. In one embodiment, the reactive group is an acrylamide, an activated ester of a carboxylic acid, an acyl azide, an acyl nitrile, an aldehyde, an alkyl halide, a silyl halide, an anhydride, an aniline, an aryl halide, an azide, an aziridine, a boronate, a diazoalkane, a haloacetamide, a halotriazine, a hydrazine (including hydrazides), an imido ester, an isocyanate, an isothiocyanate, a maleimide, a phosphoramidite, a reactive platinum complex, a sulfonyl halide, or a thiol group. By "reactive platinum complex" is particularly meant chemically reactive platinum complexes such as described in U.S. Pat. No. 5,714,327.

Where the reactive group is an activated ester of a carboxylic acid, such as a succinimidyl ester of a carboxylic acid, a sulfonyl halide, a tetrafluorophenyl ester or an isothiocyanates, the resulting compound is particularly useful for preparing conjugates of carrier molecules such as proteins, nucleotides, oligonucleotides, or haptens. Where the reactive group is a maleimide, haloalkyl or haloacetamide (including any reactive groups disclosed in U.S. Pat. Nos. 5,362,628; 5,352,803 and 5,573,904 (supra)) the resulting compound is particularly useful for conjugation to thiol-containing substances. Where the reactive group is a hydrazide, the resulting compound is particularly useful for conjugation to periodate-oxidized carbohydrates and glycoproteins, and in addition is an aldehyde-fixable polar tracer for cell microinjection. Where the reactive group is a silyl halide, the resulting compound is particularly useful for conjugation to silica surfaces, particularly where the silica surface is incorporated into a fiber optic probe subsequently used for remote ion detection or quantitation.

In a particular aspect, the reactive group is a photoactivatable group such that the group is only converted to a reactive species after illumination with an appropriate wavelength. An appropriate wavelength is generally a UV wavelength that is less than 400 nm. This method provides for specific attachment to only the target molecules, either in solution or immobilized on a solid or semi-solid matrix. Photoactivatable reactive groups include, without limitation, benzophenones, aryl azides and diazirines.

Preferably, the reactive group is a photoactivatable group, succinimidyl ester of a carboxylic acid, a haloacetamide, haloalkyl, a hydrazine, an isothiocyanate, a maleimide group, an aliphatic amine, a silyl halide, a cadaverine or a psoralen. More preferably, the reactive group is a succinimidyl ester of a carboxylic acid, a maleimide, an iodoacetamide, or a silyl halide. In a particular embodiment the reactive group is a succinimidyl ester of a carboxylic acid, a sulfonyl halide, a tetrafluorophenyl ester, an iosothiocyanates or a maleimide.

The selection of a covalent linkage to attach the reporter molecule to the carrier molecule or solid support typically depends on the chemically reactive group on the component to be conjugated. The discussion regarding reactive groups in the section immediately preceding is relevant here as well. Exemplary reactive groups typically present on the biological or non-biological components include, but are not limited to, amines, thiols, alcohols, phenols, aldehydes, ketones, phosphates, imidazoles, hydrazines, hydroxylamines, disubstituted amines, halides, epoxides, sulfonate esters, purines, pyrimidines, carboxylic acids, or a combination of these groups. A single type of reactive site may be available on the component (typical for polysaccharides), or a variety of sites may occur (e.g. amines, thiols, alcohols, phenols), as is typical for proteins. A carrier molecule or solid support may be conjugated to more than one reporter molecule, which may be the same or different, or to a substance that is additionally modified by a hapten. Although some selectivity can be obtained by careful control of the reaction conditions, selectivity of labeling is best obtained by selection of an appropriate reactive compound.

In another exemplary embodiment, the present compound is covalently bound to a carrier molecule. If the compound has a reactive group, then the carrier molecule can alternatively be linked to the compound through the reactive group. The reactive group may contain both a reactive functional moiety and a linker, or only the reactive functional moiety.

A variety of carrier molecules are useful in the present invention. Exemplary carrier molecules include antigens, steroids, vitamins, drugs, haptens, metabolites, toxins, environmental pollutants, amino acids, peptides, proteins, nucleic acids, nucleic acid polymers, carbohydrates, lipids, and polymers. In exemplary embodiment, at least one member selected from $R^1$, $R^2$, $R^3$, $R^4$, $R^5$, $R^6$, $R^7$, $R^8$, $R^9$, $R^{10}$, $R^{11}$ or $R^{12}$ comprises a carrier molecule. Preferably, at least one of $R^1$, $R^2$, $R^3$, $R^4$, $R^5$, $R^6$, $R^7$, $R^8$, comprises a carrier molecule or is attached to a carrier molecule. More preferably, at least one of $R^3$ or $R^6$ comprises a carrier molecule or is attached to a carrier molecule. Alternatively, if the present compound comprises a reactive group or solid support a reactive group may be covalently attached independently to those substituents, allowing for further conjugation to a reactive group, carrier molecule or solid support.

In an exemplary embodiment, the carrier molecule comprises an amino acid, a peptide, a protein, a polysaccharide, a nucleoside, a nucleotide, an oligonucleotide, a nucleic acid, a hapten, a psoralen, a drug, a hormone, a lipid, a lipid assembly, a synthetic polymer, a polymeric microparticle, a biological cell, a virus and combinations thereof. In another exemplary embodiment, the carrier molecule is selected from a hapten, a nucleotide, an oligonucleotide, a nucleic acid polymer, a protein, a peptide or a polysaccharide. In a preferred embodiment the carrier molecule is amino acid, a peptide, a protein, a polysaccharide, a nucleoside, a nucleotide, an oligonucleotide, a nucleic acid, a hapten, a psoralen, a drug, a hormone, a lipid, a lipid assembly, a tyramine, a synthetic polymer, a polymeric microparticle, a biological cell, cellular components, an ion chelating moiety, an enzymatic substrate or a virus. In another preferred embodiment, the carrier molecule is an antibody or fragment thereof, an antigen, an avidin or streptavidin, a biotin, a dextran, an antibody binding protein, a fluorescent protein, agarose, and a non-biological microparticle. Typically, the carrier molecule is an antibody, an antibody fragment, antibody-binding proteins, avidin, streptavidin, a toxin, a lectin, or a growth factor. Preferred haptens include biotin, digoxigenin and fluorophores.

Antibody binging proteins include, but are not limited to, protein A, protein G, soluble Fc receptor, protein L, lectins, anti-IgG, anti-IgA, anti-IgM, anti-IgD, anti-IgE or a fragment thereof.

In an exemplary embodiment, the enzymatic substrate is selected from an amino acid, peptide, sugar, alcohol, alkanoic acid, 4-guanidinobenzoic acid, nucleic acid, lipid, sulfate, phosphate, —CH$_2$OCOalkyl and combinations thereof. Thus, the enzyme substrates can be cleave by enzymes selected from the group consisting of peptidase, phosphatase, glycosidase, dealkylase, esterase, guanidinobenzotase, sulfatase, lipase, peroxidase, histone deacetylase, endoglycoceramidase, exonuclease, reductase and endonuclease.

In another exemplary embodiment, the carrier molecule is an amino acid (including those that are protected or are substituted by phosphates, carbohydrates, or $C_1$ to $C_{22}$ carboxylic acids), or a polymer of amino acids such as a peptide or protein. In a related embodiment, the carrier molecule contains at least five amino acids, more preferably 5 to 36 amino acids. Exemplary peptides include, but are not limited to, neuropeptides, cytokines, toxins, protease substrates, and protein kinase substrates. Other exemplary peptides may function as organelle localization peptides, that is, peptides that serve to target the conjugated compound for localization within a particular cellular substructure by cellular transport mechanisms. Preferred protein carrier molecules include enzymes, antibodies, lectins, glycoproteins, histones, albumins, lipoproteins, avidin, streptavidin, protein A, protein G, phycobiliproteins and other fluorescent proteins, hormones, toxins and growth factors. Typically, the protein carrier molecule is an antibody, an antibody fragment, avidin, streptavidin, a toxin, a lectin, or a growth factor. Exemplary haptens include biotin, digoxigenin and fluorophores.

In another exemplary embodiment, the carrier molecule comprises a nucleic acid base, nucleoside, nucleotide or a nucleic acid polymer, optionally containing an additional linker or spacer for attachment of a fluorophore or other ligand, such as an alkynyl linkage (U.S. Pat. No. 5,047,519), an aminoallyl linkage (U.S. Pat. No. 4,711,955) or other linkage. In another exemplary embodiment, the nucleotide carrier molecule is a nucleoside or a deoxynucleoside or a dideoxynucleoside.

Exemplary nucleic acid polymer carrier molecules are single- or multi-stranded, natural or synthetic DNA or RNA oligonucleotides, or DNA/RNA hybrids, or incorporating an unusual linker such as morpholine derivatized phosphates (AntiVirals, Inc., Corvallis Oreg.), or peptide nucleic acids such as N-(2-aminoethyl)glycine units, where the nucleic acid contains fewer than 50 nucleotides, more typically fewer than 25 nucleotides.

In another exemplary embodiment, the carrier molecule comprises a carbohydrate or polyol that is typically a polysaccharide, such as dextran, FICOLL, heparin, glycogen, amylopectin, mannan, inulin, starch, agarose and cellulose, or is a polymer such as a poly(ethylene glycol). In a related embodiment, the polysaccharide carrier molecule includes dextran, agarose or FICOLL.

In another exemplary embodiment, the carrier molecule comprises a lipid (typically having 6-25 carbons), including glycolipids, phospholipids, and sphingolipids. Alternatively, the carrier molecule comprises a lipid vesicle, such as a liposome, or is a lipoprotein (see below). Some lipophilic substituents are useful for facilitating transport of the conjugated dye into cells or cellular organelles.

Alternatively, the carrier molecule is cells, cellular systems, cellular fragments, or subcellular particles. Examples of this type of conjugated material include virus particles, bacterial particles, virus components, biological cells (such as animal cells, plant cells, bacteria, or yeast), or cellular components. Examples of cellular components that can be labeled, or whose constituent molecules can be labeled, include but are not limited to lysosomes, endosomes, cytoplasm, nuclei, histones, mitochondria, Golgi apparatus, endoplasmic reticulum and vacuoles.

In an exemplary embodiment, the carrier molecule comprises a specific binding pair member wherein the present compounds are conjugated to a specific binding pair member and are used to detect a heavy metal ion in close proximity to the complimentary member of the specific binding pair. Exemplary binding pairs are set forth in Table 2.

TABLE 2

Representative Specific Binding Pairs

| | |
|---|---|
| antigen | antibody |
| biotin | avidin (or streptavidin or anti-biotin) |
| IgG* | protein A or protein G |
| drug | drug receptor |
| folate | folate binding protein |
| toxin | toxin receptor |
| carbohydrate | lectin or carbohydrate receptor |
| peptide | peptide receptor |
| protein | protein receptor |
| enzyme substrate | enzyme |
| DNA (RNA) | cDNA (cRNA)† |
| hormone | hormone receptor |
| ion | chelator |
| antibody | antibody-binding proteins |

*IgG is an immunoglobulin
†cDNA and cRNA are the complementary strands used for hybridization In an exemplary embodiment, the present compounds of the invention are covalently bonded to a solid support. The solid support may be attached to the compound or through a reactive group, if present, or through a carrier molecule, if present. In exemplary embodiment, at least one member selected from $R^1$, $R^2$, $R^3$, $R^4$, $R^5$, $R^6$, $R^7$, $R^8$, $R^9$, $R^{10}$, $R^{11}$ and $R^{12}$ comprises a solid support. Preferably, at least one of $R^1$, $R^2$, $R^3$, $R^4$, $R^5$, $R^6$, $R^7$, or $R^8$ comprises a solid support or is attached to a solid support. More preferred, at least one of $R^3$ or $R^6$ comprises a solid support or is attached to a solid support. Alternatively, if the present compound comprises a carrier molecule or reactive group a solid support may be covalently attached independently to those substituents, allowing for further conjugation to a another dye, carrier molecule or solid support.

A solid support suitable for use in the present invention is typically substantially insoluble in liquid phases. Solid supports of the current invention are not limited to a specific type of support. Rather, a large number of supports are available and are known to one of ordinary skill in the art. Thus, useful solid supports include solid and semi-solid matrixes, such as aerogels and hydrogels, resins, beads, biochips (including thin film coated biochips), microfluidic chip, a silicon chip, multi-well plates (also referred to as microtitre plates or microplates), membranes, conducting and nonconducting metals, glass (including microscope slides) and magnetic supports. More specific examples of useful solid supports include silica gels, polymeric membranes, particles, derivatized plastic films, glass beads, cotton, plastic beads, alumina gels, polysaccharides such as Sepharose, poly(acrylate), polystyrene, poly(acrylamide), polyol, agarose, agar, cellulose, dextran, starch, FICOLL, heparin, glycogen, amylopectin, mannan, inulin, nitrocellulose, diazocellulose, polyvinylchloride, polypropylene, polyethylene (including poly(ethylene glycol)), nylon, latex bead, magnetic bead, paramagnetic bead, superparamagnetic bead, starch and the like.

In some embodiments, the solid support may include a solid support reactive functional group, including, but not limited to, hydroxyl, carboxyl, amino, thiol, aldehyde, halogen, nitro, cyano, amido, urea, carbonate, carbamate, isocyanate, sulfone, sulfonate, sulfonamide, sulfoxide, etc., for attaching the compounds of the invention. Useful reactive groups are disclosed above and are equally applicable to the solid support reactive functional groups herein.

A suitable solid phase support can be selected on the basis of desired end use and suitability for various synthetic protocols. For example, where amide bond formation is desirable to attach the compounds of the invention to the solid support, resins generally useful in peptide synthesis may be employed, such as polystyrene (e.g., PAM-resin obtained from Bachem Inc., Peninsula Laboratories, etc.), POLYHIPE™ resin (obtained from Aminotech, Canada), polyamide resin (obtained from Peninsula Laboratories), polystyrene resin grafted with polyethylene glycol (TentaGel™, Rapp Polymere, Tubingen, Germany), polydimethyl-acrylamide resin (available from Milligen/Biosearch, California), or PEGA beads (obtained from Polymer Laboratories).

While it has been stressed that a wide range of components can be used to make the heavy metal-binding compounds it should also be understood that the individual selection of components to make a particularly useful heavy metal-binding compound for detection purposes requires an understanding of the reporter molecules, carrier molecules, reactive group, solid supports, the linkers, the metal chelating moiety and how certain combinations, and substituents function to selectively bind to physiological concentrations of heavy metal ions in the presence of physiological concentrations of calcium ions or other non-target metal ions.

Preparation of Conjugates

Conjugates of components (carrier molecules or solid supports), e.g., drugs, peptides, toxins, nucleotides, phospholipids and other organic molecules are prepared by organic synthesis methods using the reactive dyes, are generally prepared by means well recognized in the art (Haugland, MOLECULAR PROBES HANDBOOK, supra, 2002). Conjugation to form a covalent bond may consist of simply mixing the reactive compounds of the present invention in a suitable solvent in which both the reactive compound and the substance to be conjugated are soluble. The reaction preferably proceeds spontaneously without added reagents at room temperature or below. For those reactive dyes that are photoactivated, conjugation is facilitated by illumination of the reaction mixture to activate the reactive dye. Chemical modification of water-insoluble substances, so that a desired dye-conjugate may be prepared, is preferably performed in an aprotic solvent such as dimethylformamide (DMF), dimethylsulfoxide (DMSO), acetone, ethyl acetate, toluene, or chloroform.

Preparation of peptide or protein conjugates typically comprises first dissolving the protein to be conjugated in aqueous buffer at about 1-10 mg/mL at room temperature or below. Bicarbonate buffers (pH about 8.3) are especially suitable for reaction with succinimidyl esters, phosphate buffers (pH about 7.2-8) for reaction with thiol-reactive functional groups and carbonate or borate buffers (pH about 9) for reaction with isothiocyanates and dichlorotriazines. The appropriate reactive compound is then dissolved in a nonhydroxylic solvent (usually DMSO or DMF) in an amount sufficient to give a suitable degree of conjugation when added to a solution of the protein to be conjugated. The appropriate amount of compound for any protein or other component is conveniently predetermined by experimentation in which variable amounts of the present compound are added to the protein, the conjugate is chromatographically purified to separate unconjugated compound and the compound-protein conjugate is tested in its desired application.

Following addition of the reactive compound to the component solution, the mixture may be incubated for a suitable period (typically about 1 hour at room temperature to several hours on ice), the excess unreacted compound is removed by gel filtration, dialysis, HPLC, adsorption on an ion exchange or hydrophobic polymer or other suitable means. The conjugate is used in solution or lyophilized. In this way, suitable conjugates can be prepared from antibodies, antibody fragments, avidins, lectins, enzymes, proteins A and G, cellular proteins, albumins, histones, growth factors, hormones, and other proteins. The approximate degree of substitution is determined from the long wavelength absorption of the compound-protein conjugate by using the extinction coefficient of the un-reacted compound at its long wavelength absorption peak, the unmodified protein's absorption peak in the ultraviolet and by correcting the UV absorption of the conjugate for absorption by the compound in the UV.

Conjugates of polymers, including biopolymers and other higher molecular weight polymers are typically prepared by means well recognized in the art (for example, Brinkley et al., *Bioconjugate Chem.*, 3: 2 (1992)). In these embodiments, a single type of reactive site may be available, as is typical for polysaccharides or multiple types of reactive sites (e.g. amines, thiols, alcohols, phenols) may be available, as is typical for proteins. Selectivity of labeling is best obtained by selection of an appropriate reactive compound. For example, modification of thiols with a thiol-selective reagent such as a haloacetamide or maleimide, or modification of amines with an amine-reactive reagent such as an activated ester, acyl azide, isothiocyanate or 3,5-dichloro-2,4,6-triazine. Partial selectivity can also be obtained by careful control of the reaction conditions.

When modifying polymers with the compounds, an excess of the compound is typically used, relative to the expected degree of compound substitution. Any residual, un-reacted compound or hydrolysis product is typically removed by dialysis, chromatography or precipitation. Presence of residual, unconjugated compound can be detected by thin layer chromatography using a solvent that elutes the compound away from its conjugate. In all cases it is usually preferred that the reagents be kept as concentrated as practical so as to obtain adequate rates of conjugation.

In an exemplary embodiment, the conjugate is associated with an additional substance that binds either to the compound or the component (reporter molecule, carrier molecule, solid support) through noncovalent interaction. In another exemplary embodiment, the additional substance is an antibody, an enzyme, a hapten, a lectin, a receptor, an oligonucleotide, a nucleic acid, a liposome, or a polymer. The additional substance is optionally used to probe for the location of the conjugate, for example, as a means of enhancing the signal of the conjugate.

Methods of Use

The heavy metal-binding compounds of the present invention are useful for any application where it is desirable to complex a target metal ion (lead, cadmium, mercury, nickel and/or lanthanum). Thus, the present compounds may be utilized without limit for the detection, monitoring, quantitation, binding and isolating of heavy metal ions. Selected heavy metal-binding compounds of the invention may be useful as ionophores, that is, they facilitate the transport of selected target ions across cell membranes. Where the heavy metal-binding compound is bound to a carrier molecule or solid support that is a polymeric matrix, such as a microparticle, dextran, polystyrene or agarose, the compounds are useful for depleting a sample solution, sequestering, of a selected target ion, particularly where the polymeric matrix is used to pack a chromatography column. Other heavy metal-binding compounds (those bound to a reporter molecule) are useful as fluorescent, colorimetric or fluorometric indicators for a selected target ion. This new class of heavy metal-binding compounds can be used in any of the same assays previously described for heavy metal indicators and other physiological metal ion indicators.

In an exemplary embodiment, the present methods comprise detecting the presence or absence of a metal ion in a sample. The steps of the method comprises combining a present metal ion reporter molecule with the sample to prepare a labeling mixture; incubating the labeling mixture for a sufficient amount of time for the metal ion reporter molecule to associate with the metal ion in the sample to form an incubated mixture; illuminating the incubated sample with an appropriate wavelength to form an illuminated mixture; and, observing the illuminated mixture whereby the presence or absence of the metal ion in a sample is detected.

The compound is typically combined with the sample as a staining solution. The staining solution is typically prepared by dissolving a present metal ion reporter molecule in an aqueous solvent such as water, a buffer solution or assay solution, such as phosphate buffered saline, or an organic solvent such as dimethylsulfoxide (DMSO), dimethylformamide (DMF), methanol, ethanol or acetonitrile. Typically, the present metal ion reporter molecules are first dissolved in an organic solvent such as DMSO as a stock solution. The stock solution is typically prepared about 300-10× more concentrated that the effective working concentration. Thus, the stock solution is diluted to an effective working concentration in an aqueous solution that optionally includes appropriate buffering components. Aqueous solution differ depending on the assay format. For detection of heavy metal ions in live cells an appropriate buffer is normal (physiological) saline, PBS (phosphate buffered saline) Hanks media, RPMI media or other cell culture media. For detection of heavy metal ions in a solution based assay format appropriate aqueous dilution solution include MOPS, Good's buffer, and PIPES buffers. Additional buffering components include such as, 50-100 mM formate buffer, pH 4.0, sodium citrate, pH 4.5, sodium acetate, pH 5.0, MES, pH 6.0, imidazole, pH 7.0, HEPES, pH 6.8, Tris acetate, pH 8.0, Tris-HCl, pH 8.5, Tris borate, pH 9.0 and sodium bicarbonate, pH 10.

An effective working concentration of the present compounds is the amount sufficient to give a detectable optical response when complexed with heavy metal ions. Typically, the effective amount is about 10 nM to 100 μM. Most preferred is about 200 nM to 5 μM. For selected reporter compounds, staining is optimal when the staining solution has a concentration of about 400 nm to about 1 μM (see Examples 8-16). It is generally understood that the specific amount of the metal ion reporter molecules present in a staining solution is determined by the physical nature of the sample and the nature of the analysis being performed.

Initially, the suitability of a heavy metal-binding compound as an indicator of heavy metal ion concentration is commonly tested by mixing a constant amount of the indicator with a measured amount of the target ion under the expected experimental conditions.

In general, this colorimetric or fluorometric method comprises combining heavy metal-binding compounds of the present invention with a sample for a sufficient time to allow said compounds to bind heavy metal ions whereby heavy metal ions are bound. Following binding of the present heavy metal ions, the sample is illuminated with an appropriate light source and the signal correlated with the known concentration of heavy metal ions. This titration curve is then used to experimentally determine the appropriate heavy metal-binding compound for a particular assay.

Preferred indicators display a high selectivity, that is, they show a sufficient rejection of non-target ions. The interference of a non-target ion is tested by a comparable titration of the indicator with that ion. Although preferred target ions for most indicators of the present invention are lead, cadmium, nickel, lanthanum, and mercury, any ion that yields a detectable change in absorption wavelengths, emission wavelengths, fluorescence lifetimes or other measurable optical property over the concentration range of interest is potentially measured using one of the indicators of this invention.

The sample may be combined with the staining solution by any means that facilitates contact between the metal ion reporter molecules and the metal ions. The contact can occur through simple mixing, as in the case where the sample is a solution. The present reporter molecules may be added to the sample directly or may contact the sample on an inert matrix such as a blot or gel, a testing strip, a microarray, or any other solid or semi-solid surface, for example where only a simple and visible demonstration of the presence of metal ions is desired. Any inert matrix used to separate the sample can be used to detect the presence of nucleic acids by observing the fluorescent response on the inert matrix. Thus, in one embodiment is provided a composition comprising a sample and a present metal ion reporter molecule.

Alternatively, the sample may include cells and/or cell membranes. While selected examples of the compound disclosed herein may permeate cellular membranes rapidly and completely upon addition of the staining solution, such as those comprising lipophilic moieties, any technique that is suitable for transporting the reporter molecules across cell membranes with minimal disruption of the viability of the cell and integrity of cell membranes is a valid method of combining the sample with the present reporter molecules for detection of intracellular metal ions. Examples of suitable processes include action of chemical agents such as detergents, enzymes or adenosine triphosphate; receptor- or transport protein-mediated uptake; pore-forming proteins; microinjection; electroporation; hypoosmotic shock; or minimal physical disruption such as scrape loading or bombardment with solid particles coated with or in the presence of the present reporter molecules.

The sample is incubated in the presence of the metal ion reporter molecules for a time sufficient to form the fluorogenic metal ion-reporter molecule complex. Detectable fluorescence in a solution of metal ions is essentially instantaneous. Detectable fluorescence within cell membranes requires the permeation of the dye into the cell. In general, visibly detectable fluorescence can be obtained in a wide variety of cells with certain cell permeant embodiments of the present invention within about 10-30 minutes after combination with the sample, commonly within about 10-20 minutes. While permeation and fluorescence should be rapid for all reporter molecules comprising a lipophilic moiety such as an AM ester, it is readily apparent to one skilled in the art that the time necessary for sufficient permeation of the dye, or sufficient formation of the fluorescent metal ion complex, is dependent upon the physical and chemical nature of the individual sample and the sample medium.

Therefore, in one aspect of the invention, for a particular heavy metal-binding compound of the present invention to be useful for detection purposes, it must exhibit a detectable change in spectral properties upon complexation of the desired metal ion (target ion) in the chelating moiety. This is necessary when heavy metal-binding compounds complexed with heavy metals cannot be separated from heavy metal-binding compounds that are not bound to heavy metal ions. Preferably the change in spectral properties is a change in fluorescence properties. More preferably, the instant compounds display an intensity increase or decrease in emission energy upon the complexation of the desired target ion. Heavy metal-binding compounds that comprise a reporter molecule that is colorimetric or fluorometric are herein referred to as "indicators".

Alternatively, a change in spectral properties upon binding of a target ion is not necessary wherein a stable ternary complex is formed. Typically this ternary complex is immobilized allowing for the removal of unbound heavy metal-binding compounds.

In another embodiment, is provided a complex comprising a present metal ion reporter molecule and a metal ion. To facilitate the detection of the metal ion-reporter molecule complex, the excitation or emission properties of the fluorescent complex are utilized. For example, the sample is excited by a light source capable of producing light at or near the wavelength of maximum absorption of the fluorescent complex, such as an ultraviolet or visible lamp, an arc lamp, a laser, or even sunlight. Preferably the fluorescent complex is excited at a wavelength equal to or greater than about 300 nm, more preferably equal to or greater than about 340 nm. The fluorescence of the complex is detected qualitatively or quantitatively by detection of the resultant light emission at a wavelength of greater than about 400 nm, more preferably greater than about 450 nm, most preferred greater than 480 nm. The emission is detected by means that include visible inspection, photographic film, or the use of current instrumentation such as fluorometers, quantum counters, plate readers, epifluorescence microscopes and flow cytometers or by means for amplifying the signal such as a photomultiplier.

In another embodiment is provided a method for detecting the presence or absence of target ions in a live cell comprises the following steps:
 a) combining a present metal ion reporter molecule with the sample to prepare a labeling mixture wherein the metal ion reporter molecule comprises at least one lipohilic group;
 b) incubating the labeling mixture for a sufficient amount of time for the metal ion reporter molecule to associate with the metal ion in the live cell to form an incubated mixture;
 c) illuminating the incubated sample with an appropriate wavelength to form an illuminated mixture; and,
 d) observing the illuminated mixture whereby the presence or absence of the metal ion in a live cell is detected Therefore, in an exemplary embodiment, compounds useful for detecting heavy metal ions in a live cell contain at least one —$(CH_2OC(O)(CH_2)_nCH_3)$ group or lipophilic group. Typically, $R_X$, $R_Y$, and $R_{X'}$ are —$CH_2CO_2R$, wherein R is $CH_2OC(O)(CH_2)_nCH_3$. In a further aspect, the compound typically comprises a reporter molecule that is a fluorophore wherein at least one of $R^1$-$R^8$ is a fluorophore. Preferably $R^3$ or $R^6$ is a xanthene fluorophore. Alternatively, the fluorophore may be substituted by a lipophilic group including, but not limited to, an AM ester.

In another embodiment is provided present heavy metal-binding compounds that are chemically reactive wherein the compound is covalently attached to a reactive group. In this way the chemically reactive heavy metal-binding compounds can be conjugated to a desired reporter molecule, carrier molecule or solid support, which may be selected from any of the above disclosed molecules and groups. The specific heavy metal-binding compound used in an assay or experiment is selected based on the desired affinity for the target heavy metal ion as determined by the expected concentration range in the sample, the desired end result, (e.g., binding, isolating or detecting), the desired live cell properties and the desired selectivity. These chemically reactive heavy metal-binding compounds allow for the end user to tailor the compound to their desired experiment.

In an exemplary embodiment, the present compounds comprise a carrier molecule or a solid support. In one aspect the carrier molecule or solid support facilitates the binding and sequestration of heavy metal ions from a solution. This has utility wherein it is desirable to deplete a solution of heavy metal ions, such as the commercially available Calcium Sponge (Molecular Probes, Inc.) for the removal of calcium ions from solution. The present compounds may be conjugated to any solid support such that when a solution containing heavy metal ions comes into contact with the present heavy metal-binding compounds the heavy metal ions are bound while the sample solution is allowed to pass freely by the immobilized heavy metal-binding compounds. Once the heavy metal-binding compounds have been saturated, the heavy metal ions can be released from the heavy metal-binding compounds by combining with an appropriate buffer to regenerate the heavy metal-binding conjugates. Appropriate buffers that are useful for releasing heavy metal ions from the present compounds include solutions of tetrakis-(2-pyridyl-methyl)ethylenediamine (TPEN). After the removal of the heavy metal ions, additional sample solution may be passed over the immobilized heavy metal-binding compounds to further remove heavy metal ions.

In one aspect, the heavy metal-binding compounds are conjugated to a polymer such as a microparticle, dextran, agarose, acrylamide, polystyrene, see Example 6 Compound 25. These conjugates are useful to pack into a column wherein a sample solution may be run through the column to remove undesirable heavy metal-ions. These conjugates are also useful for isolating and concentrating heavy metal ions. In this way the column may become saturated a number of times and heavy metal-ions repeatedly released to form a concentrated pool of heavy metal ions.

In another aspect, the present compounds are conjugated to a protein such as an antibody. In this way the heavy metal-binding compounds are selectively localized to a target wherein heavy metal ions are bound and optionally detected when the compound also comprises a reporter molecule.

In one embodiment, the compounds of the invention, in any of the embodiments described above, are associated, either covalently or noncovalently, with a solid support and a reporter molecule. The solid support includes, without limitation, a microfluidic chip, a silicon chip, a microscope slide, a microplate well, or another solid matrix, wherein the metal ion binding/solid support/reporter molecule compound is combined with the sample of interest as it flows over the surface. The detectable optical response is therefore detected on the matrix surface itself, typically by use of an instrument. This embodiment of the invention is particularly suited to high-throughput screening and/or high content screening using automated methods, as disclosed in U.S. Pat. No. 6,127,133.

Sample Preparation

The sample is generally a representative cell population, fluid or liquid suspension that is known or suspected to contain the target ion. Representative samples include intracellular fluids such as in blood cells, cultured cells, muscle tissue, neurons and the like; extracellular fluids in areas immediately outside of cells; in vesicles; in vascular tissue of plants and animals; in biological fluids such as blood, saliva, and urine; in biological fermentation media; in environmental samples such as water, soil, waste water and sea water; in industrial samples such as pharmaceuticals, foodstuffs and beverages; and in chemical reactors. Detection and quantitation of the target ion in a sample can help characterize the identity of an unknown sample, or facilitate quality control of a sample of known origin.

Thus, the sample can be a biological fluid such as whole blood, plasma, serum, nasal secretions, sputum, saliva, urine, sweat, transdermal exudates, cerebrospinal fluid, or the like. Biological fluids also include tissue and cell culture medium wherein an analyte of interest has been secreted into the medium. Alternatively, the sample may be whole organs, tissue or cells from the animal. Examples of sources of such samples include muscle, eye, skin, gonads, lymph nodes, heart, brain, lung, liver, kidney, spleen, thymus, pancreas, solid tumors, macrophages, mammary glands, mesothelium, and the like. Cells include without limitation prokaryotic cells such as bacteria, yeast, fungi, mycobacteria and mycoplasma, and eukaryotic cells such as nucleated plant and animal cells that include primary cultures and immortalized cell lines. Typically prokaryotic cells include $E.$ $coli$ and $S.$ $aureus$. Eukaryotic cells include without limitation ovary cells, epithelial cells, circulating immune cells, β cells, hepatocytes, and neurons.

In an exemplary embodiment, the sample comprises biological fluids, buffer solutions, live cells, fixed cells, eukaryotic cells, prokaryotic cells, nucleic acid polymers, nucleosides, nucleotides, a polymeric gel or tissue sections. In a further aspect, the sample comprises live cells in an aqueous buffer.

The sample may be incubated in the presence of the nucleic acid reporter molecules for a time sufficient to form a nucleic acid-reporter molecule complex. While permeation and complexation may be more or less rapid for the compounds disclosed herein, largely depending on the nature of the substituents present on the compound. It should be apparent to one skilled in the art that the time necessary for sufficient permeation of the dye, or sufficient formation of the resulting nucleic acid complex, is dependent upon the physical and chemical nature of the individual sample and the sample medium (see for example U.S. Pat. No. 5,658,751).

Quantification of target ion levels in samples is typically accomplished using the indicators of the present invention by methods known in the art. For example, the ratiometric measurement of ion concentration provides accurate measurement of ion concentrations by the treatment of the fluorescence data as the ratio of excitation or fluorescence intensities at two wavelengths, rather than the absolute intensity at a single wavelength. Using the ratio method, a number of variables that may perturb the ion concentration measurements are eliminated. In particular, ion-dependent factors that affect the signal intensity, such as nonuniform intracellular dye concentrations, probe leakage, dye bleaching and cell thickness, are canceled in the ratio measurements, since these parameters have a similar effect on intensities at both wavelengths. While the ratio method can be used to determine concentrations using observation of either the excitation spectra of the indicator, the emission spectra of the indicator, or both, in the case of the indicators of the present invention, the shift in excitation energy upon binding metal ions makes observation of the excitation spectrum a more useful technique. In either case, to achieve maximal utility, the indicator must be calibrated (to compensate for variance in the dissociation constant of the indicator due to ionic strength, viscosity, or other conditions within the sample). To calibrate the indicator, ionophores such as A-23187, gramicidin, valinomycin, or ionomycin are used. Non-ratiometric analysis can also be accomplished by calibration with a second fluorescent dye present in the sample.

Illumination

The sample containing a metal ion-reporter molecule complex may be illuminated with a wavelength of light selected to give a detectable optical response, and observed with a means for detecting the optical response. By optical response is meant any detectable colorimetric or luminescent property of the complex. Typically, the optical response is related to the excitation or emission properties of the complex.

For example, the sample may be excited by a light source capable of producing light at or near the wavelength of maximum absorption of the fluorescent complex, such as an ultraviolet or visible lamp, an arc lamp, a laser, or even sunlight. The optical response is optionally detected by visual inspection, or by use of any of the following devices: CCD camera, video camera, photographic film, laser-scanning devices, fluorometers, photodiodes, quantum counters, epifluorescence microscopes, scanning microscopes, flow cytometers, fluorescence microplate readers, or by means for amplifying the signal such as photomultiplier tubes. Where the sample is examined using a flow cytometer, examination of the sample optionally includes sorting portions of the sample according to their fluorescence response.

The wavelengths of the excitation and emission bands of the metal ion reporter molecules vary with reporter molecule composition to encompass a wide range of illumination and detection bands. This allows the selection of individual reporter molecules for use with a specific excitation source or detection filter. In particular, present reporter molecules can be selected that possess excellent correspondence of their excitation band with the 488 nm band of the commonly used argon laser or emission bands which are coincident with preexisting filters.

The presence, location, and distribution of metal ions, may be detected using the spectral properties of the compound-metal ion complex. Once the dye-metal ion complex is formed, its presence may be detected and used as an indicator of the presence, location, or type of metal ions in the sample, or as a basis for sorting cells, or as a key to characterizing the sample or cells in the sample. Such characterization may be enhanced by the use of additional reagents, including fluorescent reagents.

The foregoing methods having been described it is understood that the many and varied compounds of the present invention can be utilized with the many methods. The compounds not being limited to just those that are specifically disclosed.

Therefore, in an exemplary embodiment, the present methods utilize compounds having the formula:

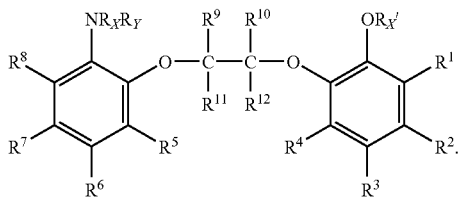

Wherein $R_X$, $R_Y$ and $R_{X'}$ are each independently hydrogen, alkyl, substituted alkyl or —$CR^{13}R^{14}CO_2R$, wherein R is H, a salt ion or —$CH_2OC(O)(CH_2)_nCH_3$ and n is 0 to 6. Each $R^{13}$ and $R^{14}$ is independently hydrogen, alkyl or substituted alkyl. In one aspect, $R_X$, $R_Y$, or $R_{X'}$ are each hydrogen. In another aspect, are each $R_X$, $R_Y$, and $R_{X'}$ are —$CH_2CO_2R$ wherein R is H, a salt ion or $CH_2OC(O)CH_3$. In a further aspect, R is hydrogen or a salt ion. In yet another aspect, R is $CH_2OC(O)CH_3$.

$R^1$-$R^8$ are independently hydrogen, halogen, alkyl, substituted alkyl, alkoxy, substituted alkoxy, hydroxyl, aryl, substituted aryl, heteroaryl, substituted heteroaryl, amino, substituted amino, alkylamino, substituted alkylamino, aldehyde, carboxyl, azido, nitro, nitroso, cyano, thioether, sulfoalkyl, carboxyalkyl, aminoalkyl, reporter molecule, reactive group, carrier molecule or solid support. Alternatively, any adjacent $R^1$-$R^8$ together with the atoms to which they are joined, form a ring which is a 5-, 6- or 7-membered heterocycloalkyl, a substituted 5-, 6- or 7-membered heterocycloalkyl, a 5-, 6- or 7-membered cycloalkyl, a substituted 5-, 6- or 7-membered cycloalkyl, a 5-, 6- or 7-membered heteroaryl, a substituted 5-, 6- or 7-membered heteroaryl, a 5-, 6- or 7-membered aryl, a substituted 5-, 6- or 7-membered aryl or reporter molecule.

The bridge substituents $R^9$-$R^{12}$ are independently hydrogen, alkyl, substituted alkyl, reactive group, carrier molecule, or solid support. Alternatively, $R^9$ in combination with $R^{10}$; or $R^{11}$ in combination with $R^{12}$ together with the atoms to which they are joined, form a ring which is a 5-, 6- or 7-membered heterocycloalkyl, a substituted 5-, 6- or 7-membered heterocycloalkyl, a 5-, 6- or 7-membered cycloalkyl, a substituted 5-, 6- or 7-membered cycloalkyl, a 5-, 6- or 7-membered heteroaryl, a substituted 5-, 6- or 7-membered heteroaryl, a 5-, 6- or 7-membered aryl, or a substituted 5-, 6- or 7-membered aryl.

In one embodiment, the present compound comprises a reporter molecule that is a chromophore, fluorophore, fluorescent protein, phosphorescent dye or a tandem dye. In one aspect, the reporter molecule is a xanthene, indole, cyanine, oxazole, dansyl, borapolyazaindacene, benzofuran, quinazolinone, benzazole, oxazine, pyrene, naphthalene, coumarin, biotin, enzyme substrate or fluorescent protein. In a further aspect, the xanthene is a fluorescein or derivative thereof, rhodamine or derivative thereof, rhodol or derivative thereof or rosamine or a derivative thereof. In another further aspect, the reporter molecule is optionally and independently substituted by hydrogen, halogen, amino, substituted amino, alkyl, substituted alkyl, aryl, substituted aryl, heteroaryl, substituted heteroaryl, alkoxy, sulfo, lipophilic group (AM ester or acetate ester) solid support, reactive group or carrier molecule. In one embodiment, at least one of $R^1$-$R^8$ is a reporter molecule. In one aspect, at least one of $R^3$ or $R^6$ is a reporter molecule.

In another exemplary embodiment, the compounds of the methods comprise a reactive group, solid support or carrier molecule either with or without the compound further comprising a reporter molecule. The reactive group, solid support, carrier molecule and optionally the reporter molecule comprise a linker that is a single covalent bond, or a covalent linkage that is linear or branched, cyclic or heterocyclic, saturated or unsaturated, having 1-20 nonhydrogen atoms selected from the group consisting of C, N, P, O and S; and are composed of any combination of ether, thioether, amine, ester, carboxamide, sulfonamide, hydrazide bonds and aromatic or heteroaromatic bonds. Alternatively, the reporter group, such as benzofuran, does not comprise a linker, but instead shares atoms with the ring A or ring B of the acetic acid analog of BAPTA.

Thus, in one embodiment of the methods the compounds comprise a reactive group that is useful for forming conjugates to reporter molecules, solid supports and/or carrier molecules. The reactive groups are selected from the group consisting of an acrylamide, an activated ester of a carboxylic acid, a carboxylic ester, an acyl azide, an acyl nitrile, an aldehyde, an alkyl halide, an anhydride, an aniline, an amine, an aryl halide, an azide, an aziridine, a boronate, a diazoalkane, a haloacetamide, a halotriazine, a hydrazine, an imido ester, an isocyanate, an isothiocyanate, a maleimide, a phosphoramidite, a reactive platinum complex, a silyl halide, a sulfonyl halide, a thiol and a photoactivatable group. In one aspect, the reactive group is selected from the group consisting of carboxylic acid, succinimidyl ester of a carboxylic acid, hydrazide, amine and a maleimide.

In another embodiment of the methods the compounds comprise a carrier molecule selected from the group consisting of an amino acid, a peptide, a protein, a polysaccharide, a nucleoside, a nucleotide, an oligonucleotide, a nucleic acid, a hapten, a psoralen, a drug, a hormone, a lipid, a lipid assembly, a synthetic polymer, a polymeric microparticle, a biological cell or a virus. In one aspect, the carrier molecule is selected from the group consisting of an antibody or fragment thereof, an avidin or streptavidin, a biotin, a dextran, an IgG binding protein, a fluorescent protein, agarose, and a non-biological microparticle.

In yet another embodiment of the methods, the compound comprise a solid support selected from the group consisting of a microfluidic chip, a silicon chip, a microscope slide, a microplate well, silica gels, polymeric membranes, particles, derivatized plastic films, glass beads, cotton, plastic beads, alumina gels, polysaccharides, polyvinylchloride, polypropylene, polyethylene, nylon, latex bead, magnetic bead, paramagnetic bead, and superparamagnetic bead. In one aspect, the solid support is selected from the group consisting of Sepharose, poly(acrylate), polystyrene, poly(acrylamide), polyol, agarose, agar, cellulose, dextran, starch, FICOLL, heparin, glycogen, amylopectin, mannan, inulin, nitrocellulose, diazocellulose and starch.

Kits

Suitable kits for forming a metal ion-reporter molecule complex and detecting the metal ions also form part of the present disclosure. Such kits can be prepared from readily available materials and reagents and can come in a variety of embodiments. The contents of the kit will depend on the design of the assay protocol or reagent for detection or measurement. All kits will contain instructions, appropriate reagents, and one or more of the presently disclosed nucleic acid reporter molecules. Typically, instructions include a tangible expression describing the reagent concentration or at least one assay method parameter such as the relative amounts of reagent and sample to be added together, maintenance time periods for reagent/sample admixtures, temperature, buffer conditions and the like to allow the user to carry out any one of the methods or preparations described above. In one aspect, the kit is formulated to facilitate the high-throughput screening of multiple samples, such as may be accomplished using automated methods.

Therefore, kits of the present invention comprise at least one heavy metal-binding compound of the present invention in an appropriate storage form, e.g. lyophilized or dissolved in an organic solvent, and instructions for preparing the heavy metal-binding compound to be used by the end user.

In addition, the kits may contain appropriate controls (including a positive control), metal ion calibration standards, ample preparation reagents, an aqueous metal ion reporter molecule dilution buffer, an organic solvent, and additional detection reagents such as calcium ion indicators, organelle stains, a metal ion indicator other than for heavy metal ions, an antibody or fragment thereof or a reference dye standard.

Therefore, in an exemplary embodiment, the kits contain compounds having the formula:

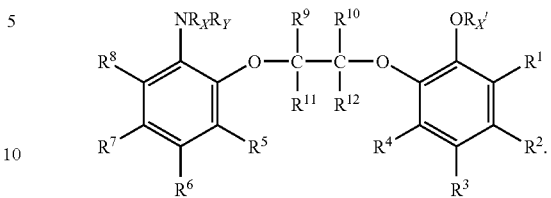

Wherein $R_X$, $R_Y$ and $R_x'$ are each independently hydrogen, alkyl, substituted alkyl or —$CR^{13}R^{14}CO_2R$, wherein R is H, a salt ion or —$CH_2OC(O)(CH_2)_nCH_3$ and n is 0 to 6. Each $R^{13}$ and $R^{14}$ is independently hydrogen, alkyl or substituted alkyl. In one aspect, $R_X$, $R_Y$, or $R_x'$ are each hydrogen. In another aspect, are each $R_X$, $R_Y$, and $R_x'$ are —$CH_2CO_2R$ wherein R is H, a salt ion or $CH_2OC(O)CH_3$. In a further aspect, R is hydrogen or a salt ion. In yet another aspect, R is $CH_2OC(O)CH_3$.

$R^1$-$R^8$ are independently hydrogen, halogen, alkyl, substituted alkyl, alkoxy, substituted alkoxy, hydroxyl, aryl, substituted aryl, heteroaryl, substituted heteroaryl, amino, substituted amino, alkylamino, substituted alkylamino, aldehyde, carboxyl, azido, nitro, nitroso, cyano, thioether, sulfoalkyl, carboxyalkyl, aminoalkyl, reporter molecule, reactive group, carrier molecule or solid support. Alternatively, any adjacent $R^1$-$R^8$ together with the atoms to which they are joined, form a ring which is a 5-, 6- or 7-membered heterocycloalkyl, a substituted 5-, 6- or 7-membered heterocycloalkyl, a 5-, 6- or 7-membered cycloalkyl, a substituted 5-, 6- or 7-membered cycloalkyl, a 5-, 6- or 7-membered heteroaryl, a substituted 5-, 6- or 7-membered heteroaryl, a 5-, 6- or 7-membered aryl, a substituted 5-, 6- or 7-membered aryl or reporter molecule.

The bridge substituents $R^9$-$R^{12}$ are independently hydrogen, alkyl, substituted alkyl, reactive group, carrier molecule, or solid support. Alternatively, $R^9$ in combination with $R^{10}$; or $R^{11}$ in combination with $R^{12}$ together with the atoms to which they are joined, form a ring which is a 5-, 6- or 7-membered heterocycloalkyl, a substituted 5-, 6- or 7-membered heterocycloalkyl, a 5-, 6- or 7-membered cycloalkyl, a substituted 5-, 6- or 7-membered cycloalkyl, a 5-, 6- or 7-membered heteroaryl, a substituted 5-, 6- or 7-membered heteroaryl, a 5-, 6- or 7-membered aryl, or a substituted 5-, 6- or 7-membered aryl.

In one embodiment, the present compound comprises a reporter molecule that is a chromophore, fluorophore, fluorescent protein, phosphorescent dye or a tandem dye. In one aspect, the reporter molecule is a xanthene, indole, cyanine, oxazole, dansyl, borapolyazaindacene, benzofuran, quinazolinone, benzazole, oxazine, pyrene, naphthalene, coumarin, biotin, enzyme substrate or fluorescent protein. In a further aspect, the xanthene is a fluorescein or derivative thereof, rhodamine or derivative thereof, rhodol or derivative thereof or rosamine or a derivative thereof. In another further aspect, the reporter molecule is optionally and independently substituted by hydrogen, halogen, amino, substituted amino, alkyl, substituted alkyl, aryl, substituted aryl, heteroaryl, substituted heteroaryl, alkoxy, sulfo, lipophilic group (AM ester or acetate ester) solid support, reactive group or carrier molecule. In one embodiment, at least one of $R^1$-$R^8$ is a reporter molecule. In one aspect, at least one of $R^3$ or $R^6$ is a reporter molecule.

In another exemplary embodiment, the compounds of the kits comprise a reactive group, solid support or carrier molecule either with or without the compound further comprising a reporter molecule. The reactive group, solid support, carrier molecule and optionally the reporter molecule comprise a linker that is a single covalent bond, or a covalent linkage that is linear or branched, cyclic or heterocyclic, saturated or unsaturated, having 1-20 nonhydrogen atoms selected from the group consisting of C, N, P, O and S; and are composed of any combination of ether, thioether, amine, ester, carboxamide, sulfonamide, hydrazide bonds and aromatic or heteroaromatic bonds. Alternatively, the reporter group, such as benzofuran, does not comprise a linker, but instead shares atoms with the ring A or ring B of the acetic acid analog of BAPTA.

Thus, in one embodiment of the kits the compounds comprise a reactive group that is useful for forming a conjugate with a reporter molecule, carrier molecule and/or solid support. The reactive group is selected from the group consisting of an acrylamide, an activated ester of a carboxylic acid, a carboxylic ester, an acyl azide, an acyl nitrile, an aldehyde, an alkyl halide, an anhydride, an aniline, an amine, an aryl halide, an azide, an aziridine, a boronate, a diazoalkane, a haloacetamide, a halotriazine, a hydrazine, an imido ester, an isocyanate, an isothiocyanate, a maleimide, a phosphoramidite, a reactive platinum complex, a silyl halide, a sulfonyl halide, a thiol and a photoactivatable group. In one aspect, the reactive group is selected from the group consisting of carboxylic acid, succinimidyl ester of a carboxylic acid, hydrazide, amine and a maleimide.

In another embodiment of the kits the compounds comprise a carrier molecule selected from the group consisting of an amino acid, a peptide, a protein, a polysaccharide, a nucleoside, a nucleotide, an oligonucleotide, a nucleic acid, a hapten, a psoralen, a drug, a hormone, a lipid, a lipid assembly, a synthetic polymer, a polymeric microparticle, a biological cell or a virus. In one aspect, the carrier molecule is selected from the group consisting of an antibody or fragment thereof, an avidin or streptavidin, a biotin, a dextran, an IgG binding protein, a fluorescent protein, agarose, and a non-biological microparticle.

In yet another embodiment of the kits, the compound comprise a solid support selected from the group consisting of a microfluidic chip, a silicon chip, a microscope slide, a microplate well, silica gels, polymeric membranes, particles, derivatized plastic films, glass beads, cotton, plastic beads, alumina gels, polysaccharides, polyvinylchloride, polypropylene, polyethylene, nylon, latex bead, magnetic bead, paramagnetic bead, and superparamagnetic bead. In one aspect, the solid support is selected from the group consisting of Sepharose, poly(acrylate), polystyrene, poly(acrylamide), polyol, agarose, agar, cellulose, dextran, starch, FICOLL, heparin, glycogen, amylopectin, mannan, inulin, nitrocellulose, diazocellulose and starch.

A detailed description of the invention having been provided above, the following examples are given for the purpose of illustrating the invention and shall not be construed as being a limitation on the scope of the invention or claims.

EXAMPLES

Example 1

Preparation of Compound 12

Compounds 1 (11.3 g, 36.8 mmol) and 2 (5.35 g, 38.5 mmol) were dissolved in DMF (~200 mL), then potassium carbonate (13.8 g, 100 mmol) was added. The reaction mixture was heated at 110-130° C. with stirring for 12-18 hours, until TLC ($R_f$=0.6, EtOAc/hexanes (30:70)) of a water-EtOAc aliquot shows that the starting material had been consumed. The reaction mixture was cooled to ambient temperature, then poured into ice water (~1.2 L) and stirred at ambient temperature. After stirring for ~15 minutes the oil coagulated into a crystalline solid. Stirring was continued until a filterable solid was obtained. The solids were collected on a glass frit funnel by suction-filtration, rinsed with water, and dried to yield 12.7 g of 3 as pale yellow crystalline solid.

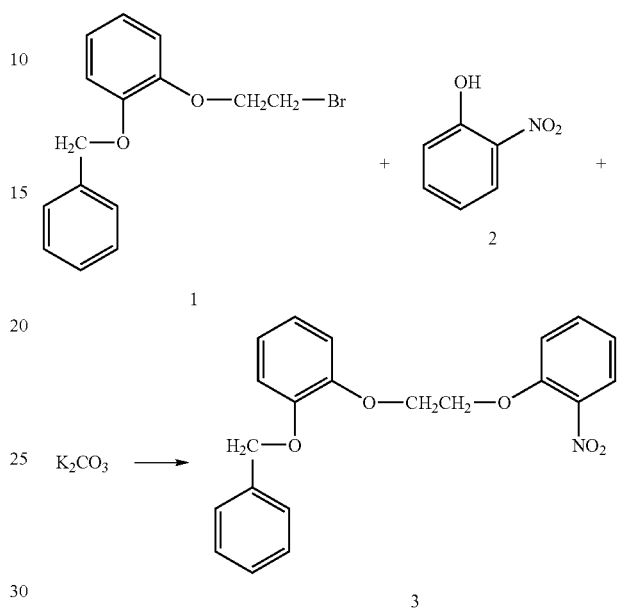

A solution of 3 (12.7 g, 34.76 mmol) in 1:1 chloroform/acetic acid (~100 mL) was treated with 10% palladium on carbon (1.0 g) and shaken with a Parr shaker under hydrogen at ~40 psi for 12-18 hours, until TLC ($R_f$=0.6, EtOAc/hexanes (30:70)) showed consumption of 3. The reaction mixture was suction filtered through Celite in a Buchner funnel, rinsing the solid with chloroform. The filtrate was concentrated with rotary evaporation to give an off-white solid. The solid was washed with hexanes and dried to yield 8.35 g of 4 as colorless solid.

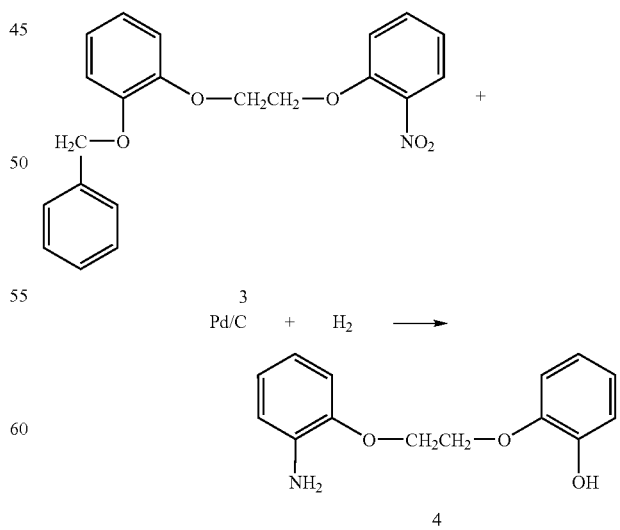

A solution of 4 (0.51 g, 2.1 mmol), methyl bromoacetate (3.0 mL, d 1.616, 32 mmol) and diisopropylethylamine (1.74 mL, d 0.742, 10 mmol) in acetonitrile (~25 mL) was heated at reflux under argon with a condenser and magnetic stirring for ~48 hours, until TLC (EtOAc/hexanes (3:2)) showed conversion of 4 ($R_f$=0.7) into 5 ($R_f$=0.6). The volatiles were removed with rotary evaporation. The residue was dissolved in EtOAc (~75 mL) then washed with 10% citric acid (2×25 mL) and brine (1×25 mL). The organic layer was dried over sodium sulfate, filtered and concentrated to a brown residue. This residue was purified by flash chromatography on silica gel (37×5 cm column) using increasing amounts of ethyl acetate in hexanes. Pure product fractions were pooled and dried by rotary evaporation to give 5 as 485 mg as pale brown foam.

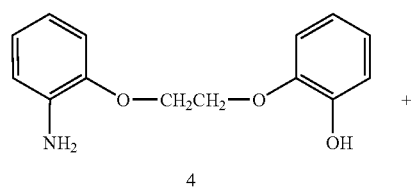

4

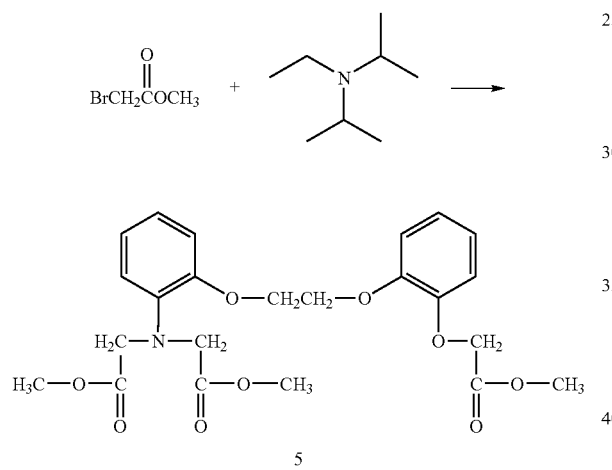

5

A solution of 5 (0.60 g, 1.3 mmol) in dry DMF (5 mL) under argon was treated with phosphorous oxychloride (0.49 mL, d 1.645, 5.2 mmol) at ambient temperature. The resulting clear solution was stirred for 12-18 hours in a 40° C. bath, until TLC (EtOAc/hexanes (3:2)) of a water-EtOAc aliquot showed consumption of 5 ($R_f$=0.6) and formation of 6 ($R_f$=0.45). The reaction solution was cooled to ambient temperature then poured into water (~150 mL). The pH was adjusted to 7 with aqueous sodium carbonate. The resulting precipitate was collected on a Buchner funnel, rinsed with water and dried under house vacuum to yield 0.61 g of 6 as light yellow powder.

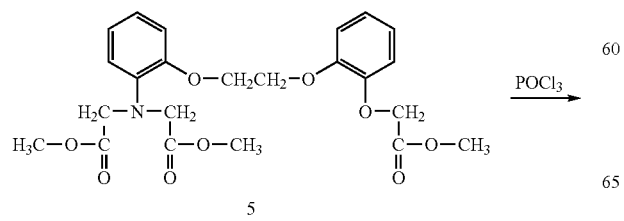

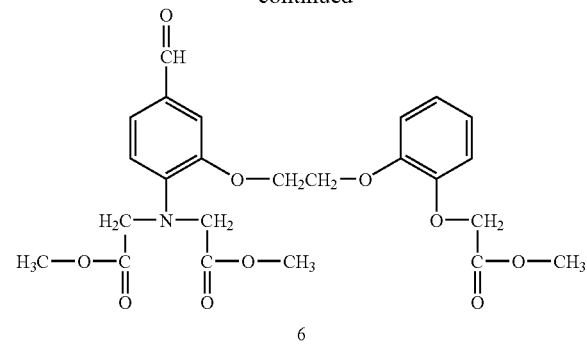

6

A solution of 6 (200 mg, 0.41 mmol) and 7 (105 mg, 0.82 mmol) in methanesulfonic acid (~4 mL) was stirred at ambient temperature with a magnetic stir bar for ~30 min., until TLC (CHCl$_3$/MeOH/AcOH (20:4:1)) of a water-EtOAc aliquot showed consumption of 6 ($R_f$=0.9) and 7 ($R_f$=0.45), and formation of 8 ($R_f$=0.2). The reaction solution was added dropwise into a stirring solution of 3M sodium acetate (~40 mL). The resulting precipitate was collected on a Buchner funnel, rinsed with water, and dried vacuum to yield 0.28 g of 8 as colorless powder.

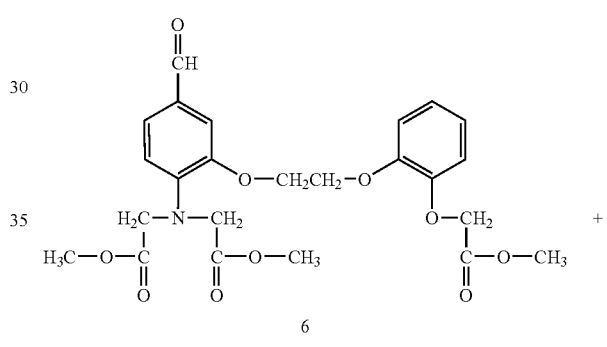

6

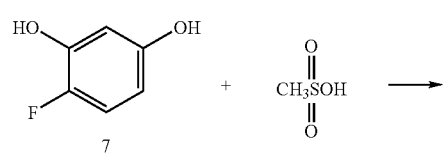

7

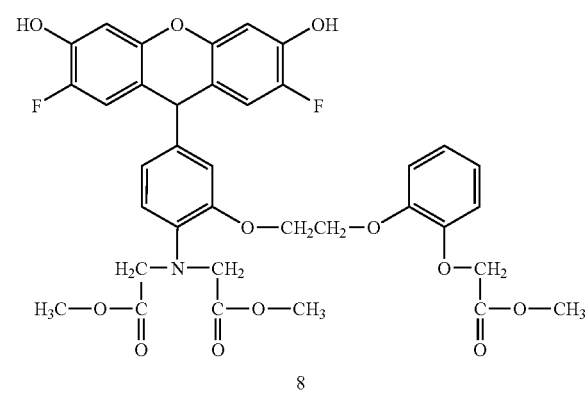

8 p-Chloranil (0.37 gm 1.52 mmol) was added to a solution of 8 (0.54 g, 0.76 mmol) in CHCl$_3$/MeOH (1:1, ~30 mL). The orange reaction mixture was stirred at reflux 12-18 hours, until TLC (CHCl$_3$/MeOH/AcOH (50:5:1)) showed formation of 9 (R$_f$=0.75, orange spot). The reaction mixture was cooled to ambient temperature, and the solvents removed with rotary evaporation. The residue was purified by flash chromatography on silica gel (4×28 cm column) using CHCl$_3$/MeOH/AcOH (50:5:1) as the elution solvent. Desired fractions were combined and concentrated in vacuo to give 9 as 0.30 g of a dark orange solid.

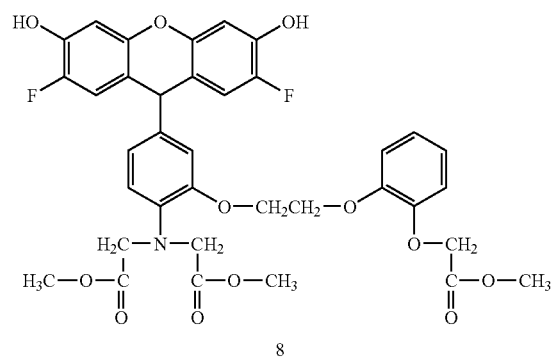

8

+

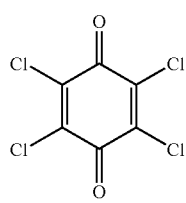

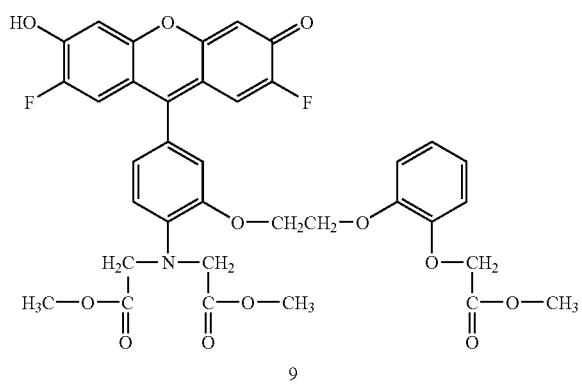

9

A solution of 9 (0.30 g, 0.42 mmol) in methanol/dioxane (1:1, 20 mL) was treated with 1M KOH (4.5 mL, 4.5 mmol). The reaction mixture was stirred for 12-18 hours, until TLC (dioxane/IPA/H$_2$O/NH$_4$OH (15:58:13:14)) showed consumption of 9 (R$_f$=0.95) and formation of 10 (R$_f$=0.4, orange spot). The pH was adjusted from 12.0, as measured by a pH meter, to 9.0 by dropwise addition of 1M HCl. The solvents were removed with a rotary evaporation to a dry residue. This residue was purified by chromatography on Sephadex LH-20 (4×37 cm column) using water as eluant. Desired product fractions were pooled and lyophilized to give 10 as (245 mg of an orange powder.

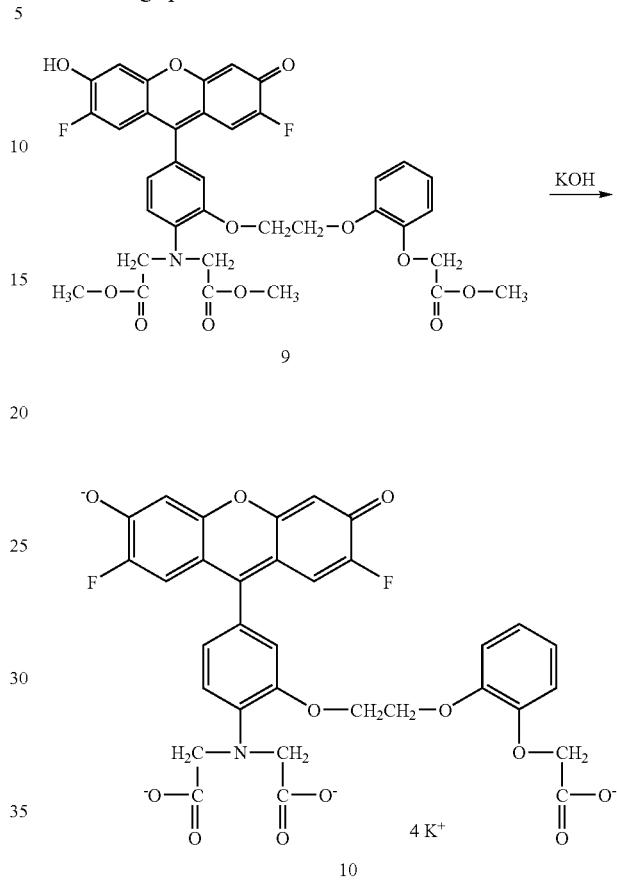

The pH of a solution of 10 (25 mg, 0.031 mmol) in H$_2$O (~3 mL) was adjusted from 7.5 to 2.0 by dropwise addition of 5% aqueous HCl with stirring. The resulting precipitate was collected on a Hirsch funnel, rinsed with water, and dried under vacuum to yield 21 mg of 11 as an amber powder. A solution of 11 (35 mg, 0.053 mmol) in dry DMF (~2 mL) was prepared under argon, then bromomethyl acetate (50 μL, d 1.560, 0.53 mmol) and diisopropylethylamine (92 ∞L, d 0.742, 0.53 mmol) were added. The orange reaction solution was stirred at ambient temperature for ~3 hours, until TLC (MeOH/CHCl$_3$ (10:90)) of a water-EtOAc aliquot showed the reaction to be complete (Rf=0.7, orange dim fluorescent spot). The reaction mixture was poured into 10% aqueous citric acid (~40 mL). The resulting mixture was extracted with 20% toluene/EtOAc (2×25 mL). The organic layer was washed with water (1×20 mL) and brine (1×20 mL), dried over sodium sulfate, filtered and concentrated with rotary evaporation to yield 52 mg of crude 12 as an orange residue. This residue was purified by flash chromatography on a silica gel column (2×26 cm) using 10% methanol/chloroform as eluant. Pure product fractions were pooled and concentrated to give 12 as 25 mg of an orange solid.

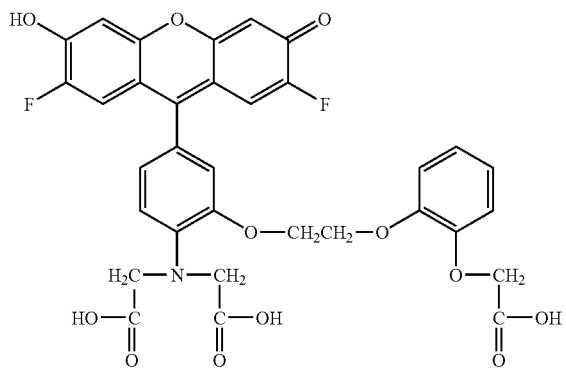

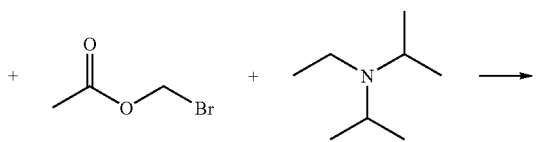

11

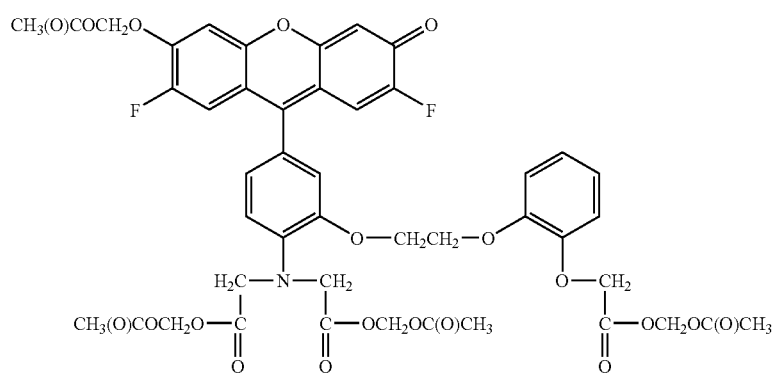

12

Example 2

Preparation of Compound 15

A pale brown mixture of compound 6 (0.20 g, 0.41 mmol) and crystallized 3-dimethylaminophenol (0.11 g, 0.82 mmol) in 6 mL propionic acid was heated overnight at 60° C. under argon. TLC (EtOAc/hexanes 3:2) of a water/EtOAc aliqhot showed consumption of 6 (Rf 0.55) and formation of compound 13 (Rf 0.20). After cooling, the reaction solution was added slowly to 50 mL 3M aqueous sodium acetate with stirring. The resulting precipitate was collected on a Buchner funnel, rinsed with water (3×10 mL), and dried in vacuo to give 13 as 0.26 g of a lavender powder.

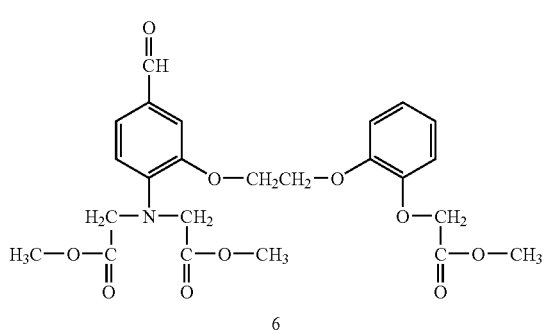

6

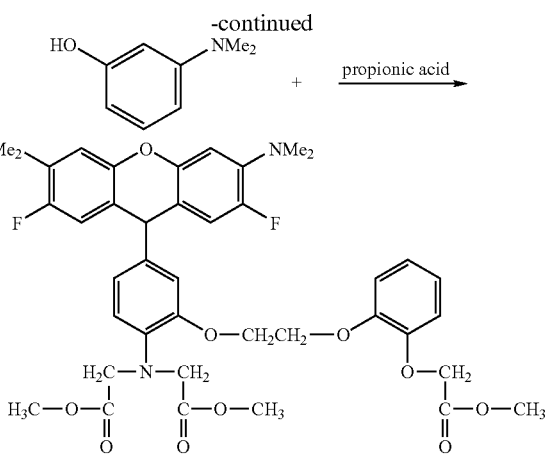

13

To a solution of compound 13 (0.26 g, 0.36 mmol) in 1:1 methanol/chloroform (15 mL) was added p-chloranil (0.13 g, 0.54 mmol) at rt. The resulting mixture was stirred for 4 h, whereupon TLC (chloroform/methanol/acetic acid, 50:5:1) showed consumption of 13 (Rf 0.25), and formation of compound 14 (Rf 0.05, red fluorescent spot). The volatiles were removed in vacuo, and the residue purified by flash chromatography on a silica gel column using chloroform/methanol/acetic acid (50:5:1) as eluant. Fractions containing pure 14 were pooled and concentrated in vacuo to give 0.13 g of a purple solid.

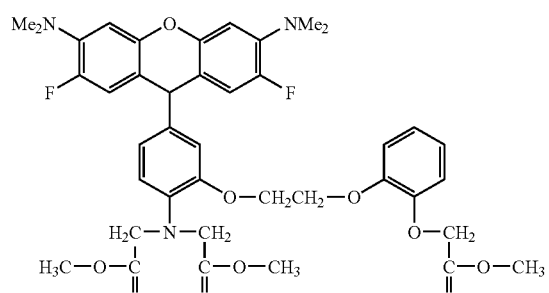

13

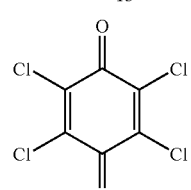

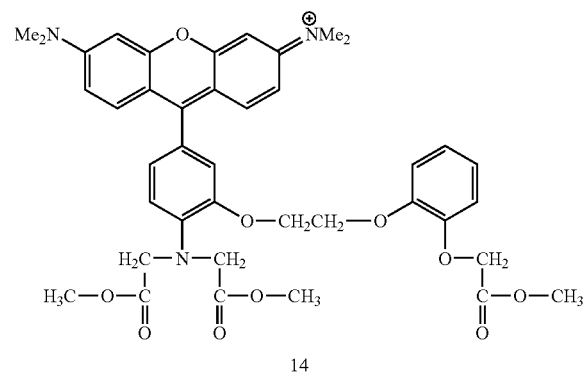

14

To a red solution of compound 14 (0.13 g, 0.18 mmol) in 1:1 methanol/dioxane (11 mL) was added a 1M solution of KOH (1.5 mL, 1.5 mmol). The resulting pale red-brown mixture was stirred at rt, whereupon after 3 h TLC (dioxane-isopropanol-water-ammonium hydroxide (15:58:13:14)) showed consumption of 14 (Rf 0.75) and formation of 15 (Rf 0.25). The reaction pH was lowered from 13 to 8 by dropwise addition of 10% aqueous citric acid, followed by concentration in vacuo. The residue was purified by gravity chromatography on Sephadex LH-20 using water as eluant. Pure product fractions were combined and lyophilized to give compound 15 as 79 mg of red powder.

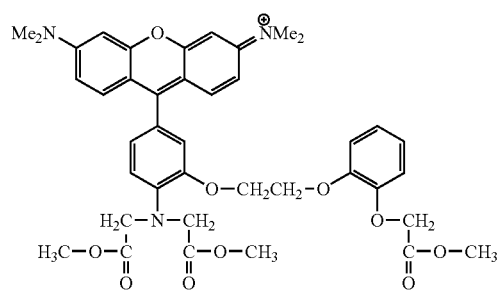

14

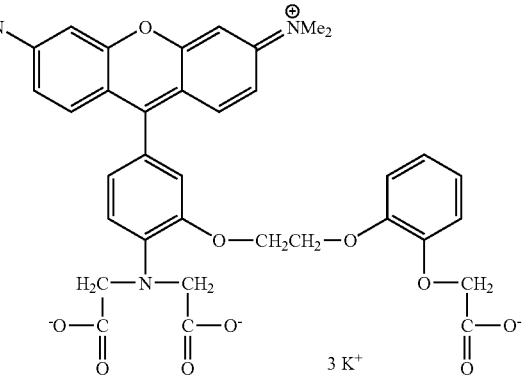

15

Example 3

Preparation of Compound 18

To a light yellow solution of compound 6 (0.18 g, 0.37 mmol) and phosphonium salt 7 (0.20 g, 0.37 mmol) in dry DMF (8 mL) under argon was added potassium carbonate (72 mg, 0.52 mmol). The resulting mixture was heated at 90° C. for 48 h, whereupon TLC (EtOAc/hexanes 3:2) showed consumption of 6 (Rf 0.50) and formation of stilbene 16 (Rf 0.60). After cooling, the reaction mixture was poured into 80 mL 10% citric acid, then extracted with 4:1 EtOAc/toluene (4×25 mL). The extract was washed with water (1×) and brine (1×), dried over sodium sulfate, and concentrated in vacuo to give crude compound 16 as 0.48 g of a red-yellow oil. Further purification was effected by flash chromatography on silica gel using 1:1 EtOAc/hexanes. Pure product fractions were combined and evaporated to give 16 as 0.19 g of a red-yellow oil.

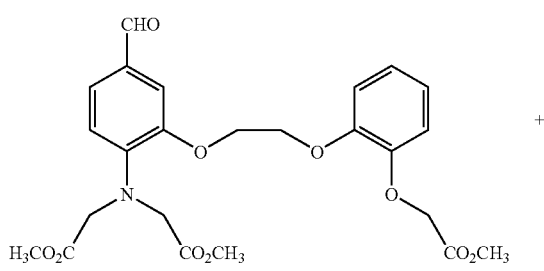

6

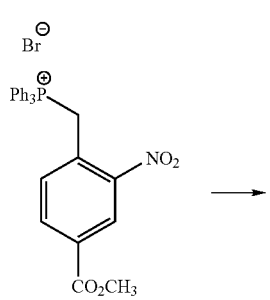

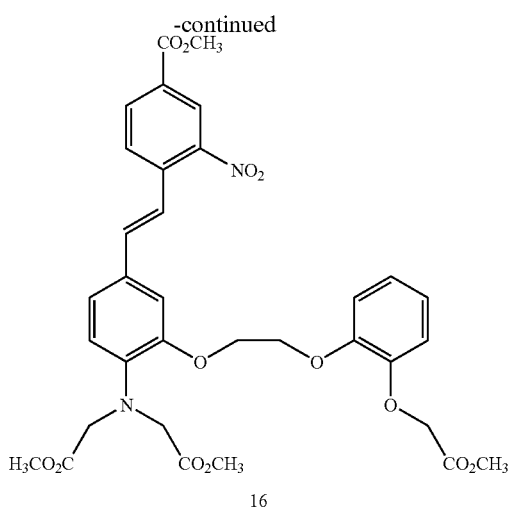

A solution of compound 16 (0.19 g, 0.29 mmol) in triethylphosphite (3 mL) was heated to 120° C. under argon for 16 h, whereupon TLC (EtOAc/hexanes 3:2) showed conversion of compound 16 (Rf 0.55) into compound 17 (Rf 0.45, blue fluorescent). The volatiles were removed in vacuo, and the residue purified by flash chromatography on silica gel using 1:1 EtOAc/hexanes as eluant. Pure product fractions were combined and evaporated to give compound 17 as 0.13 g of a pale yellow immobile glass.

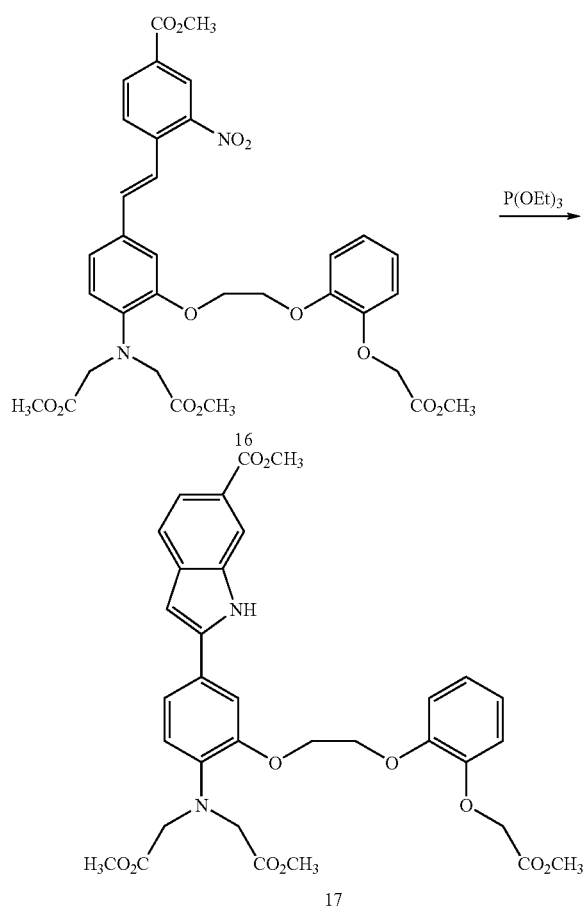

To a solution of compound 17 (0.13 g, 0.20 mmol) in 5 mL dioxane/methanol (1:1) was added a 1M KOH solution (1.4 mL, 1.4 mmol). The resulting solution was kept at rt for 2 h, whereupon TLC (dioxane-isopropanol-water-ammonium hydroxide (15:58:13:14)) showed conversion of 17 (Rf 0.9) to compound 18 (Rf 0.4). The volatiles were removed in vacuo, and the residue purified by chromatography on a Sephadex LH-20 column using water as eluant. Pure product fractions were combined and lyophilized to give compound 18 as 49 mg of a pale yellow powder.

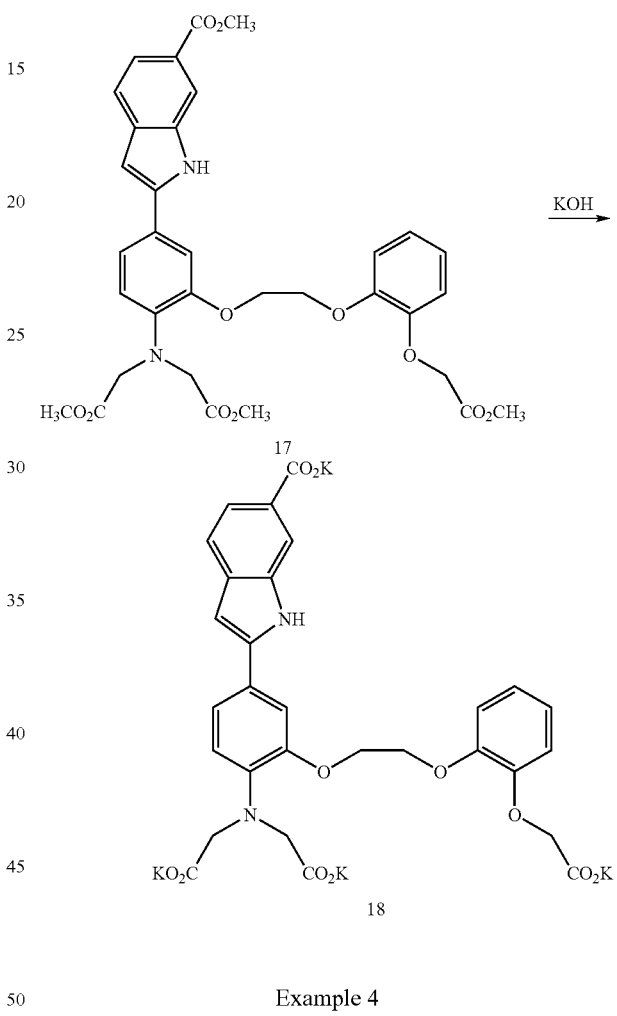

Example 4

Preparation of Compound 25

A 0.1 M solution of aldehyde 6 in acetic anhydride is cooled on ice, and treated dropwise with 1.05 eq 70% nitric acid with stirring. The ice bath is removed and the resulting dark yellow solution is stirred until TLC shows complete nitration (~30 minutes). The reaction solution is poured into excess water, followed by extraction with ethyl acetate. The extract is washed with aqueous sodium bicarbonate, water, and brine, dried over sodium sulfate, and concentrated in vacuo to a red-yellow oil which is purified by flash chromatography on silica gel using increasing ethyl acetate in hexanes to afford pure compound 19 as a yellow solid.

A 0.3 M solution of aldehyde 19 in methanesulfonic acid at rt is treated with 2 eq of 4-fluororesorcinol. The resulting mixture is stirred until homogeneity is achieved (~30 minutes), then the reaction solution is poured into excess water. The resulting precipitate is collected on a Buchner funnel, washed with copious amounts of water, and dried in vacuo to give compound 20 as an off-white powder.

A 0.2 M solution of nitro compound 20 in methanol is treated with 10 wt % of 10% palladium/carbon. The resulting mixture is shaken overnight in a Parr apparatus at 40 psi hydrogen gas. The resulting mixture is suction filtered through Celite, and concentrated in vacuo to give aniline 21 as a pale brown glass.

A 0.5 M solution of aniline 21 in dichloromethane is treated with 20 eq of trifluoroacetic anhydride. The resulting solution is stirred for 3 hours at rt, then poured into excess water. The organic phase is washed with aqueous sodium bicarbonate (3×), water, and brine, dried over sodium sulfate, and concentrated in vacuo to give trifluoroacetamide 22 as a pale brown glass.

A 0.2 M solution of trifluoroacetamide 22 in 1:1 chloroform/methanol is treated with 2 eq of p-chloranil. The resulting mixture is heated at reflux for 48 hours. After cooling, the reaction mixture is filtered and the trifluoroacetamide 23 is isolated by flash chromatography on silica gel using increasing amounts of methanol in chloroform. Compound 23 is obtained as an amber powder.

A 0.5 M solution of 23 in methanol is treated with aqueous potassium carbonate (5 eq) at rt. The resulting solution is stirred overnight, then concentrated in vacuo. The residue is taken up in 10% aqueous citric acid, then extracted 3× with chloroform. The extract is dried over sodium sulfate and concentrated in vacuo. The resulting aniline is immediately dissolved in chloroform at 0.5 M, then treated with 10 eq thiophosgene. The resulting solution is stirred for 3 hours, then concentrated in vacuo. Toluene (2×) is stripped from the residue, which is dried under high vacuum overnight to give compound 24.

A 0.5M solution of compound 24 in DMSO is added to a 0.2 M solution of 10000 MW aminodextran in aqueous sodium bicarbonate, in a ratio of 5 eq of Compound 24 per amino group per dextran. The reaction pH is 8-9. The resulting mixture is stirred for 48 hr at rt, then added dropwise to a 50× volume excess of methanol. The resulting precipitate is collected by centrifugation and washed with fresh methanol, then dried in vacuo to give an orange powder. This powder (the tetramethyl ester of compound 25) is dissolved in water to 0.5 M, then treated with aq KOH so that the reaction pH is 13. The resulting solution is kept overnight, then the pH is lowered to 9 and the volatiles removed in vacuo. The residue is applied to a Sephadex LH-20 column as a solution in minimal water, then eluted with water. Pure product fractions are combined and lyophilized to give compound 25 as a fluffy orange powder.

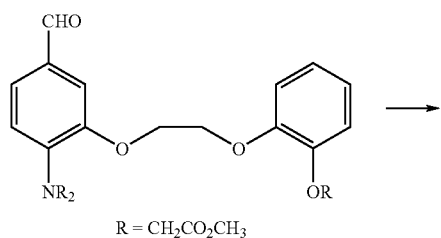

6

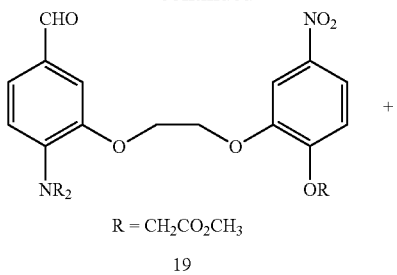

19

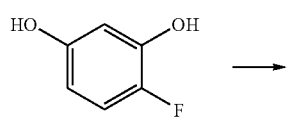

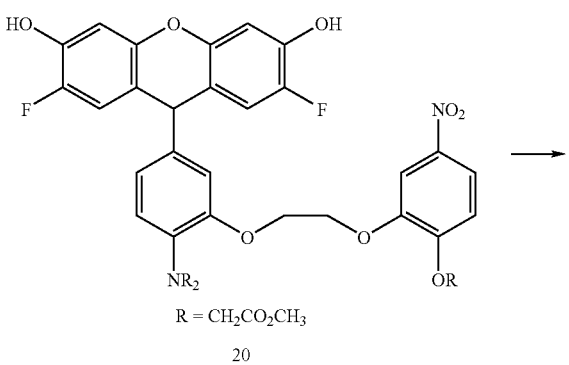

20

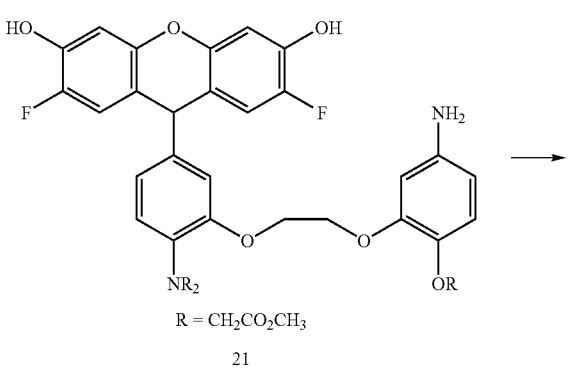

21

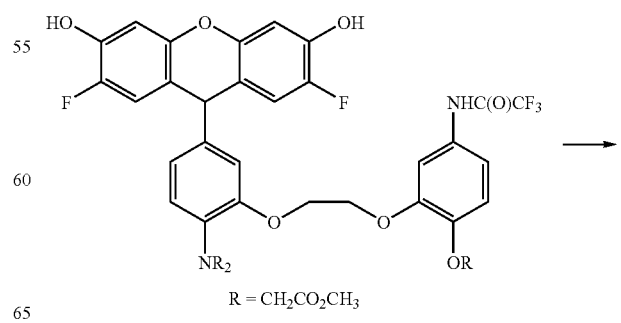

22

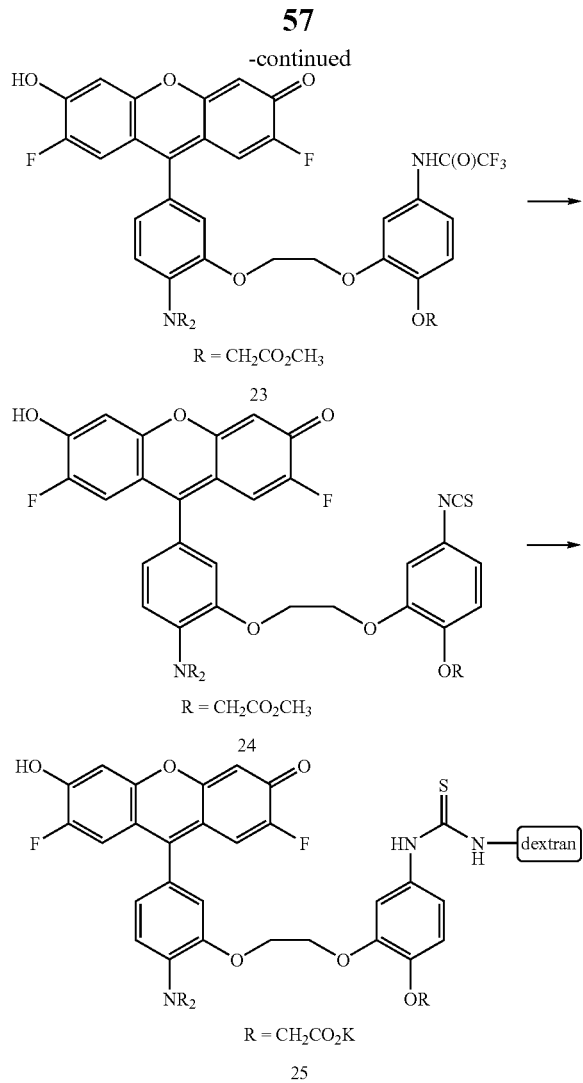

Example 5

Detection of Lead, Mercury and Cadmium Ions in Cuvettes Using Compound 10

Figure 2A:
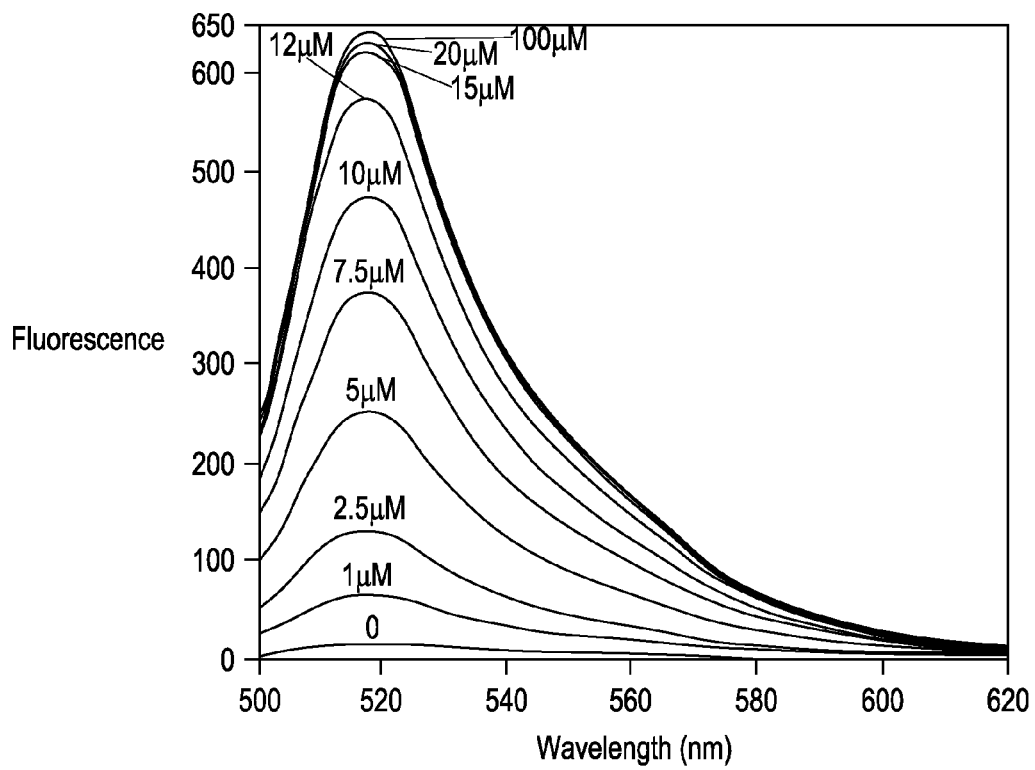
FIG. 2: Shows the detection and titration (0 to 100 μM) of A) lead ions (Kd=4.9 μM), B) cadmium ions (Kd=1.3 μM) and C) mercury ions (Kd=75 μM) in a solution containing 50 mM MOPS (pH 7.0) and 1 μM of Compound 10. Excitation 492 nm.
Figure 2B:
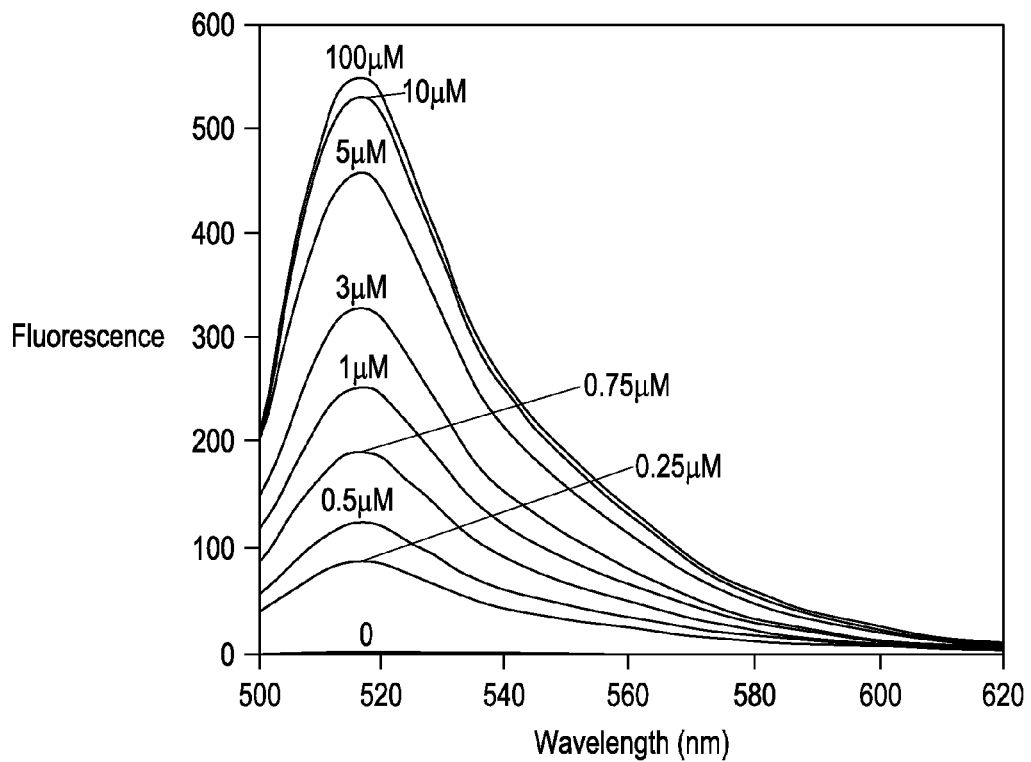
Figure 2C:
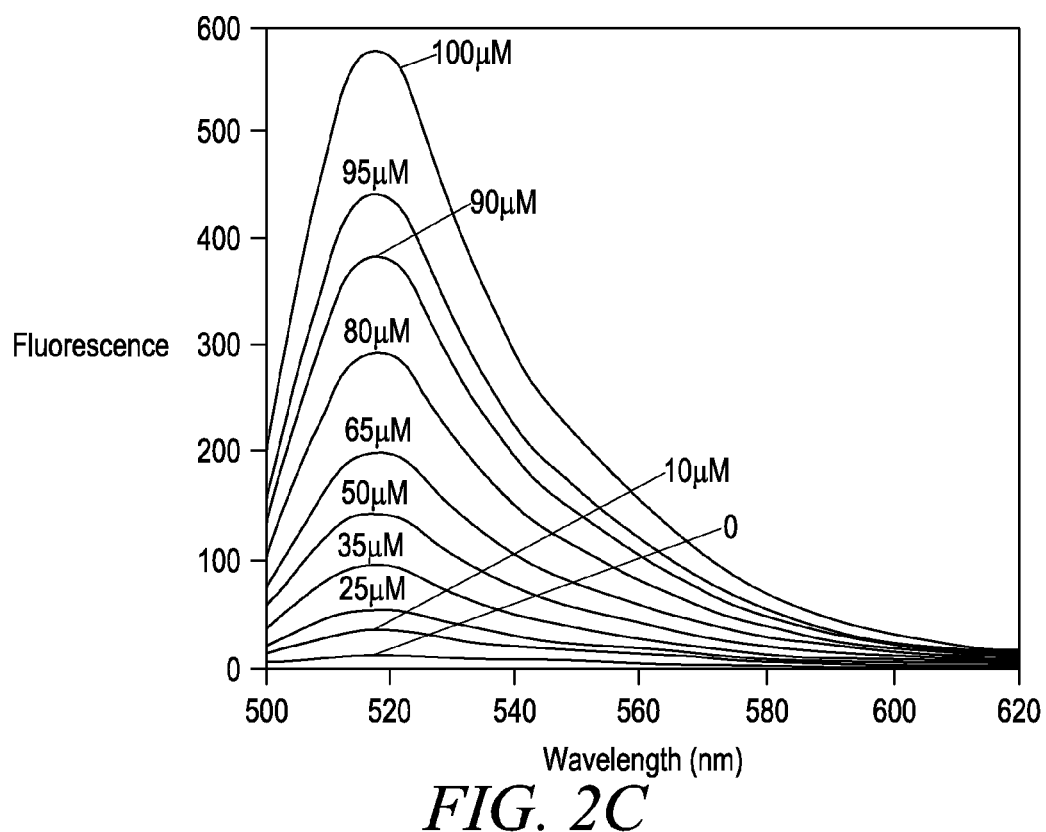
Figure 3:
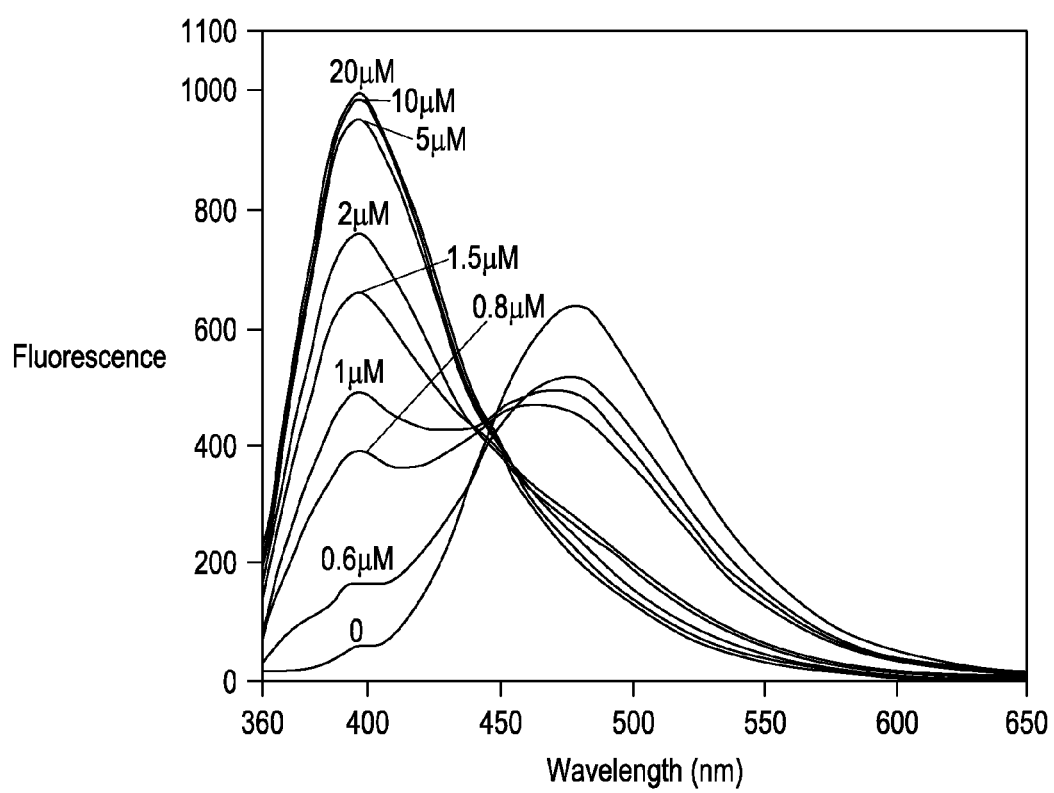
FIG. 3: Shows the detection and titration of cadmium ions (0 to 20 μM) (Kd=1.2 μM) in a solution containing 50 mM MOPS (pH 7.0) and 1 μM of Compound 18. Excitation 348 nm.

A dye stock (709 µM) solution of Compound 10 was prepared in DMSO. Lead, cadmium and mercury solutions from 0-100 µM were prepared in disposable cuvettes by diluting a 100 µM metal stock solutions to a final volume of 2 mL with 50 mM MOPS (pH7). The 100 µM metal stocks were also in 50 mM MOPS (pH7). For the cadmium titration, dye stock was added to give a final concentration of 0.35 µM. For the lead and mercury titrations, dye stock was added to give a final concentration of 1.42 µM. Samples were excited at 492 nm and fluorescence was recorded at 517 nm. The following Kd values were calculated: cadmium 1.3 µM, lead 4.9 µM, mercury 75 µM. See, FIG. 2.

Example 6

Detection of Lead, Cadmium and Mercury Ions in Cuvettes Using Compound 15

Figure 1B:
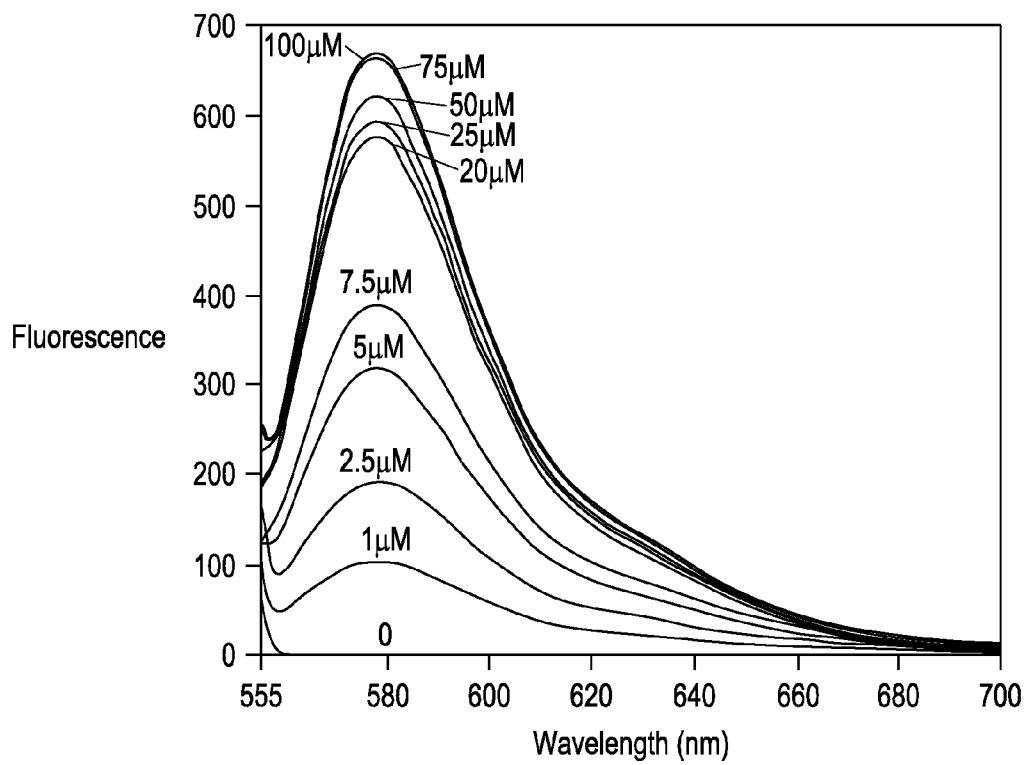
Figure 1C:
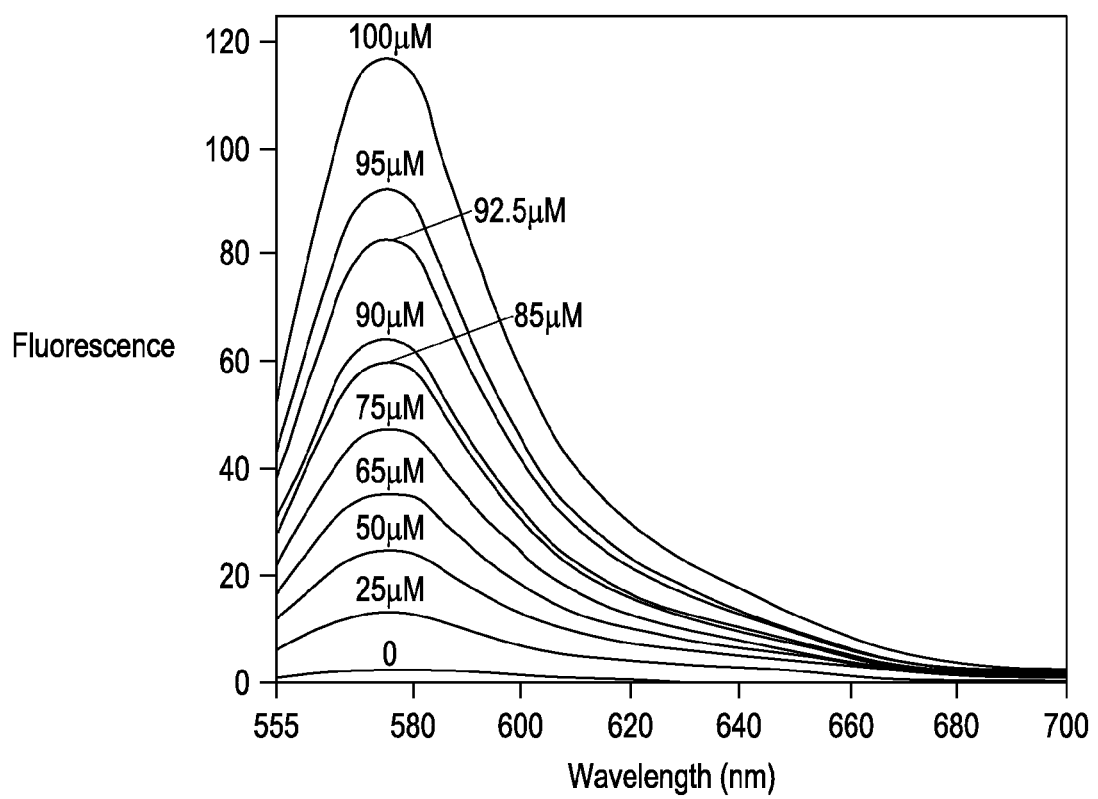

The experiment was performed as described above except that the exact dye concentrations were unknown. Sample was dissolved in DMSO and diluted 2× in nano-pure H2O before running. Ex./Em. 549/577 nm. Kd values: cadmium 4.6 uM, lead 2.1 µM, mercury 78 µM. See, FIG. 1.

Example 7

Detection of Cadmium Ions in Cuvettes Using Compound 18

The experiment was performed as described above for cadmium ion detection except that the exact dye concentrations were unknown. Ex./Em. 348/397/481 nm (ratiometric). Kd value: 1.2 µM.

Example 8

Detection of Intracellular Lead Ions

Jurkat cells were suspended at 1×10$^6$/ml in saline (0.85% sodium chloride), and 1 µM of Compound 12 was added to 1 ml of cells, incubated at 37° C. for 1 hr, washed once with saline, and resuspended in either saline or 1 µM PbCl$_2$. 1 µM Ionomycin was added to designated tubes, tubes were incubated for 30 minutes at 37° C., washed ×2 in saline.

The cell pellet was resuspended in saline, and tubes were run on a flow cytometer (Beckman Coulter Epics Elite ESP, Miami, Fla., USA). The 488 nm laser was used for excitation, and single color fluorescence was collected with 525/20BP emission filter. Tubes 1 thru 7 are all negative controls, with tube 8 the only one expected to have fluorescence. Tube 1: Cells in saline only; Tube 2: cells in saline+1 µM ionomycin; Tube 3: cells in 1 µM PbCl$_2$ in saline; Tube 5: cells in 1 µM PbCl$_2$ in saline+1 µM ionomycin; Tube 6: cells in saline+1 µM Compound 12+1 µM ionomycin; Tube 7: cells in 1 µM PbCl$_2$ in saline+1 µM Compound 12; Tube 8: cells in 1 µM PbCl$_2$ in saline+1 µM Compound 12+1 µM ionomycin.

Figure 4:
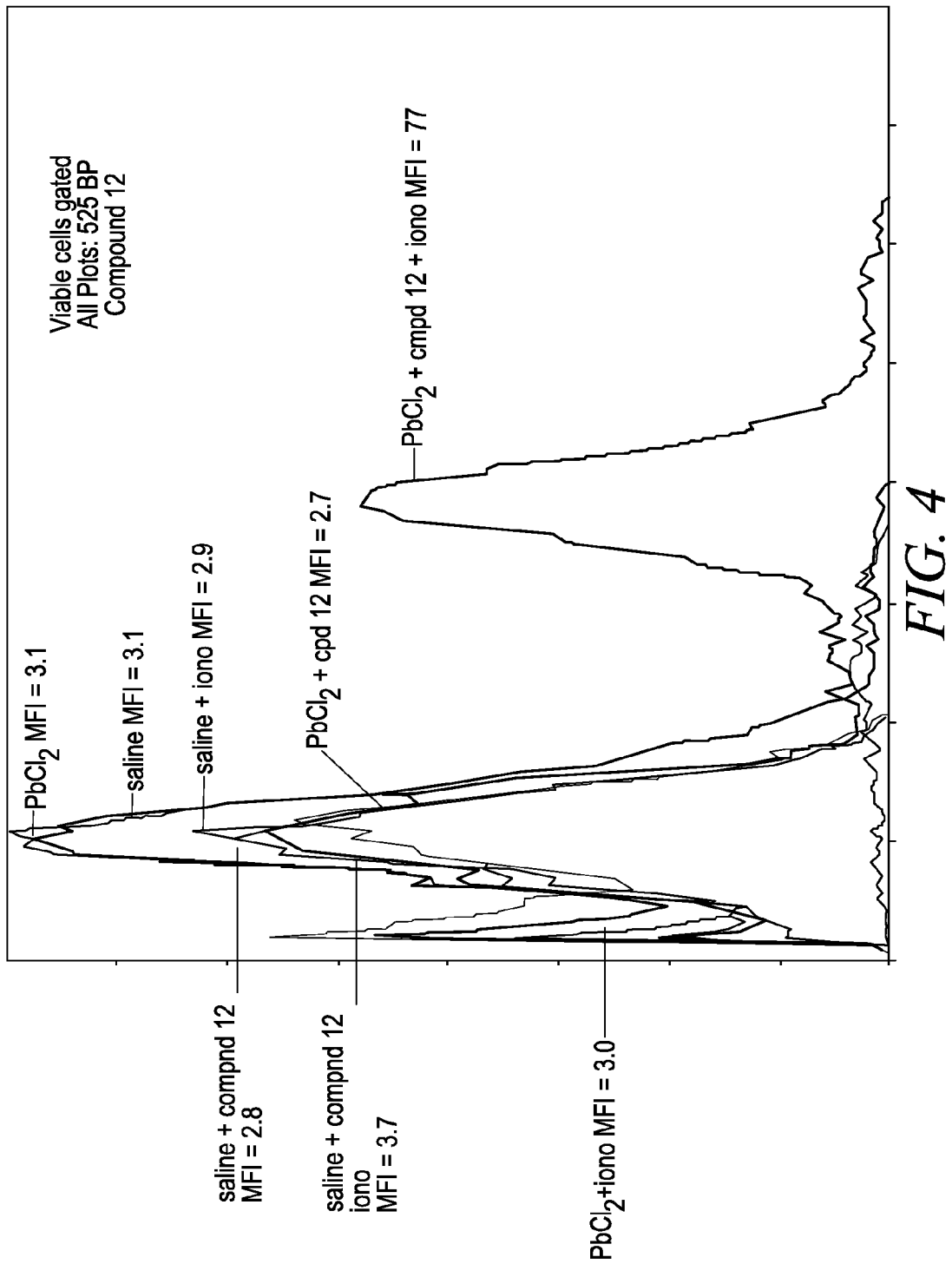
FIG. 4: Shows the detection of intracellular lead ions (I μM $PbCl_2$ added to Jurkat cells in the presence of an ionophore) with Compound 12.

The first seven tubes were negative controls and the resulting Mean Fluorescence Intensity (MFI) for all tubes was the same as unstained cells (MFI range 2.7-3.7), See FIG. 4. The last sample, tube 8, containing Compound 12+PbCl$_2$+ionomycin, produced a positive response (MFI=77) that was easily distinguished from negative peaks. These results demonstrate that the present Compound 12 was selectively binding intracellular lead ions.

Example 9

Compound 12 Tested with PbCl$_2$ (1 nM-1 µM)

Figure 5A:
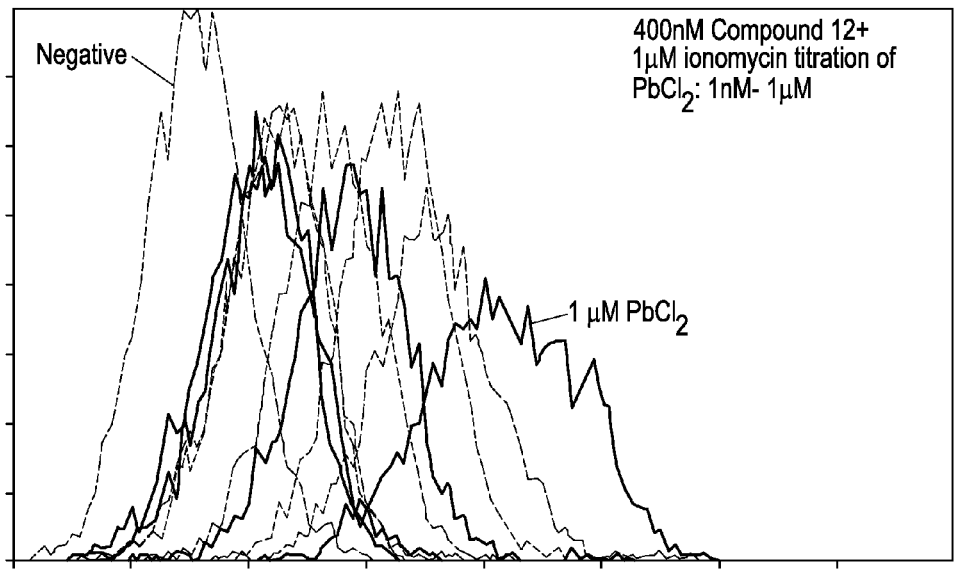
FIG. 5: Shows the change in fluorescence intensity based on concentration of $PbCl_2$ (1 nM to 1 μM) added to Jurkat cells, 5a) is an overlay of histograms showing how concentration of $PbCl_2$ affects the fluorescence and 5b) is a plot of Mean Fluorescence Intensity (MFI) versus $PbCl_2$ concentration that shows increasing fluorescence with increasing $PbCl_2$ concentration.
Figure 5B:
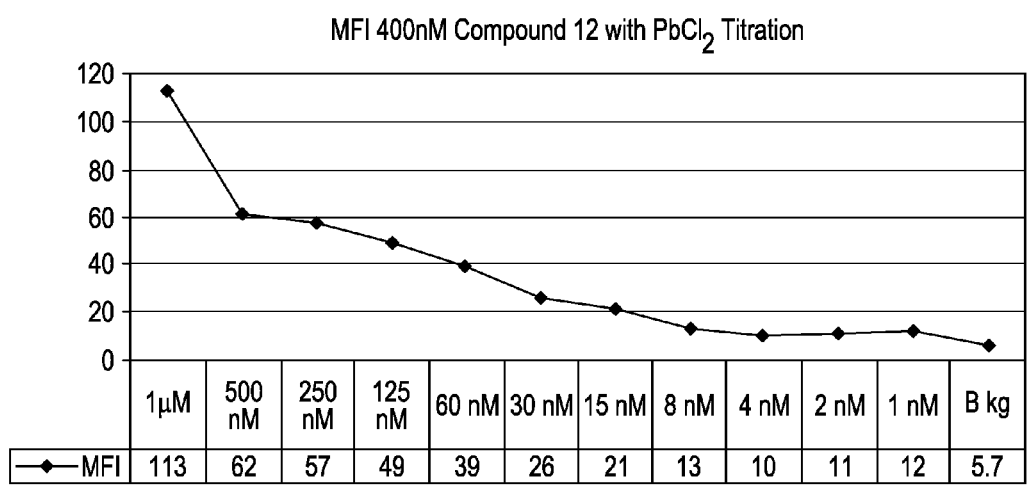
Figure 6A:
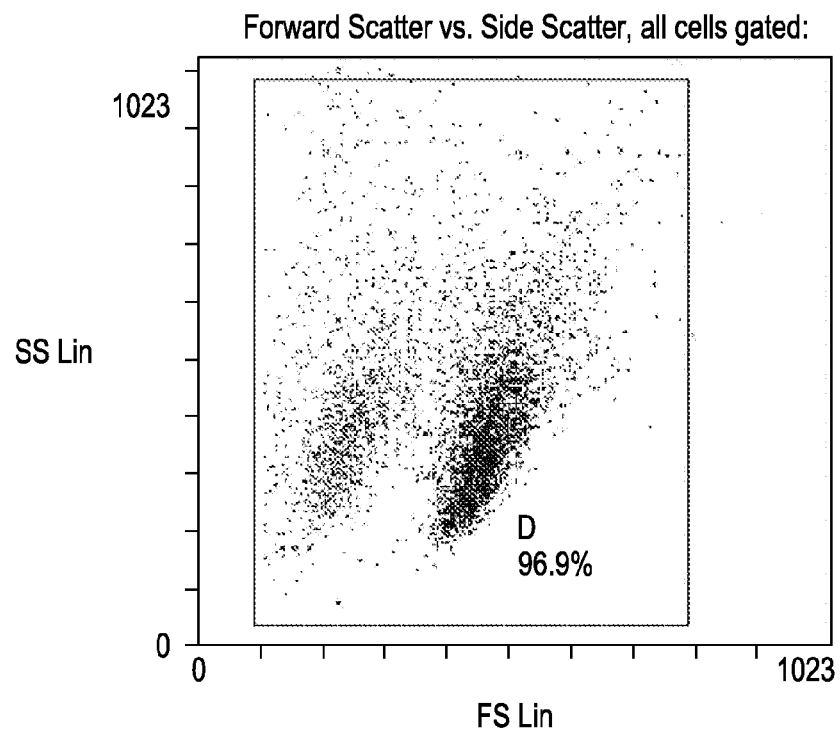
FIG. 6: Shows that Compound 12 stains only viable cells (when incubated with $PbCl_2$ in the presence of an ionophore) without causing cell death wherein 6a) is a dot plot of forward scatter vs side scatter with two populations of cells, wherein the group of cells on the left are dead (stained with Propidium Iodide (PI)) while the cells on the right are stained with Compound 12 (viable cells); 6b) is the fluorescence from Compound 12 (incubated with lead chloride solution), collected at 525/20BP; 6c) is the fluorescence from Propidium Iodide, collected at 610/20BP; and 6d) is a dual color fluorescence plot (525BP vs 610BP) wherein cells in the top left quadrant are positive for PI (dead cells) while the cells in the bottom right quadrant are positive for Compound 12 (live cells).
Figure 6B:
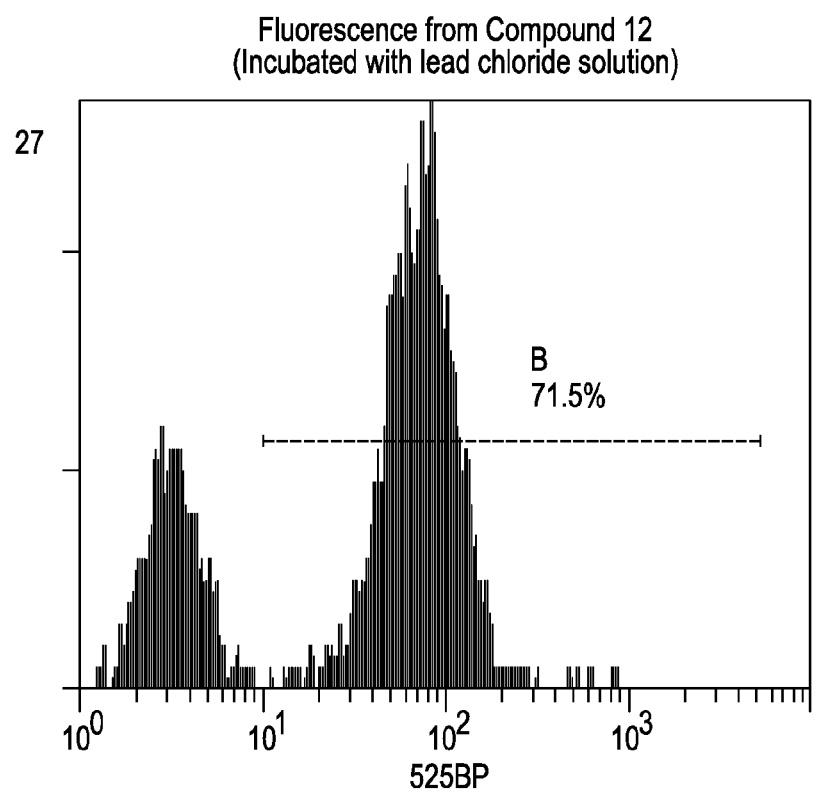
Figure 6C:
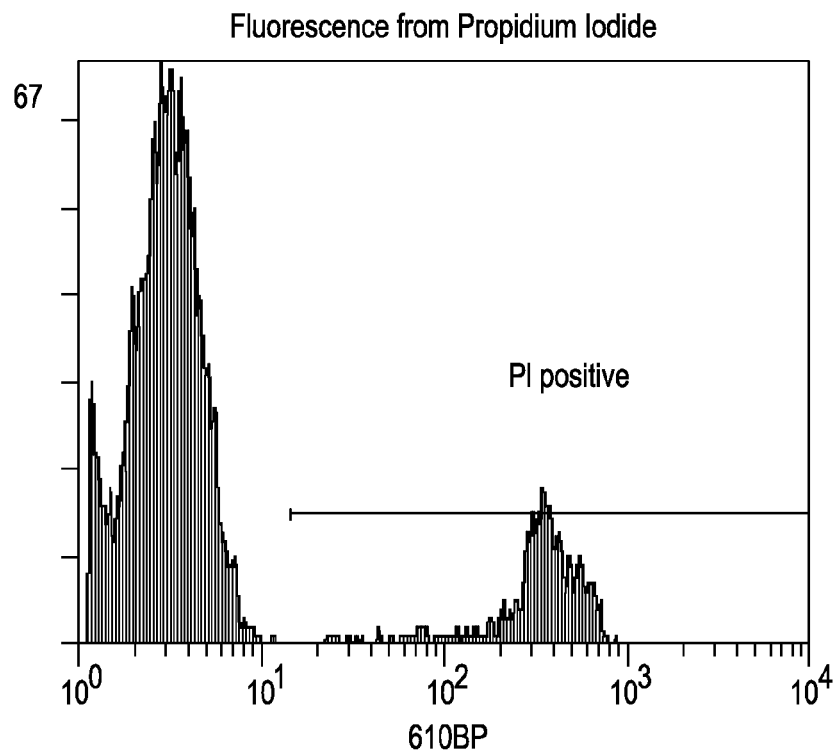
Figure 6D:
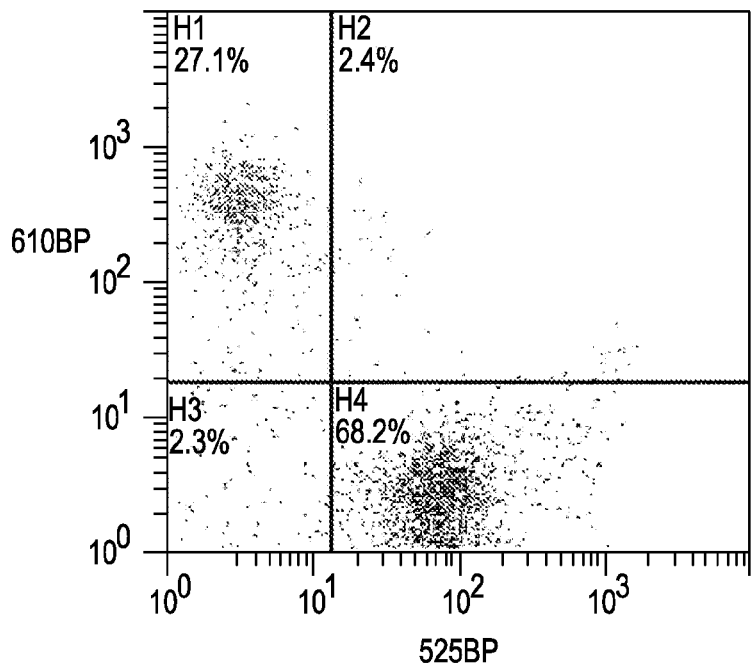

Jurkat cells were suspended at 1×10$^6$/ml in saline (0.85% sodium chloride), and 400 nM Compound 12 was added to 1 ml cells, incubated at 37° C. for 1 hr, washed once with saline, and resuspended in either saline or a range of PbCl$_2$ solutions of 1 nM-1 µM 1 µM Ionomycin was added to tubes, incubated 30 minutes at 37° C., and washed ×2 in saline. The cell pellet was resuspended in saline, and analyzed on a flow cytometer. The 488 nm laser was used for excitation, a gate was made on Forward Scatter vs Side Scatter, and single color fluorescence was collected with 525/20BP emission filter. The results demonstrate that fluorescence intensity can be correlated to concentration of lead ions and that 1 nm of PbCl$_2$ is distinguished from background fluorescence, See FIG. 5.

Example 10

Dual Staining with Propidium Iodide (to Distinguish Dead Cells) and Compound 12 (to Detect Lead Ions)

Jurkat cells were suspended at 1×10$^6$/ml in saline (0.85% sodium chloride), and 1 µM Compound 12 was added to 1 ml cells, incubated at 37° C. for 1 hr, washed once with saline, and resuspended in either saline or 1 µM PbCl$_2$. 1 µM ionomycin was added to tubes, incubated 30 minutes at 37° C., and washed ×2 in saline. The cell pellet was resuspended in saline. Propidium Iodide was added at 150 µM, incubated for 5 min at room temperature, and samples were run on a flow cytometer. The 488 nm laser was used for excitation, and dual color fluorescence was collected with 525/20BP emission filter for Compound 12 and 610/20BP emission filter for PI. The results demonstrate that the population of cells stained with propidium iodide (dead cells) are mutually exclusive from the population of cells stained with Compound 12 (live cells) demonstrating that Compound 12 is staining viable cells only, and does not cause cell death, See FIG. 6.

Example 11

Figure 7:
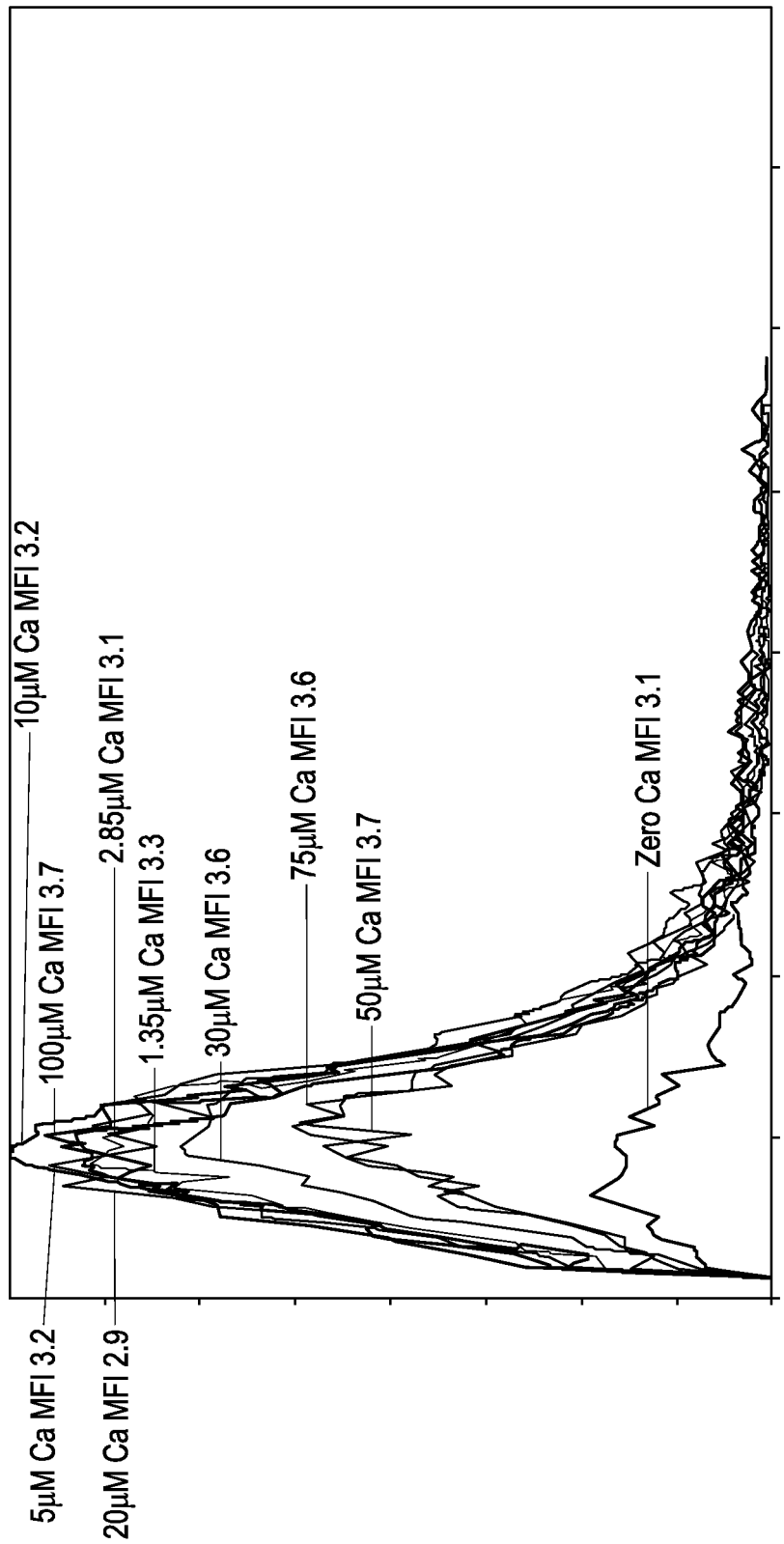
FIG. 7: Shows the histogram from cells incubated with Compound 12 and free calcium ions demonstrating that Compound 12 does not detect intracellular calcium ions.

Compound 12 Does Not Produce a Detectable Response in the Presence of Intracellular Calcium Ions Jurkat cells were suspended at 1×10$^6$/ml in saline (0.85% sodium chloride). 1 µM Compound 12 was added to 1 ml cells, incubated at 37° C. for 1 hr, washed once with saline, and resuspended in 10 different Free Calcium ion solutions (range 0-100 µM Calcium). 1 µM Ionomycin was added to tubes, incubated for 30 minutes at 37° C., and washed ×2 in saline. The cell pellet was resuspended in saline and analyzed on a flow cytometer. The 488 nm laser was used for excitation, with a live cell gate on Forward Scatter vs Side Scatter, and single color fluorescence was collected with 525/20BP emission filter. No fluorescence response was seen with cells incubated with any concentration of Calcium+ionomycin, See FIG. 7.

Example 12

Detection of Intracellular Cadmium Ions

Figure 8:
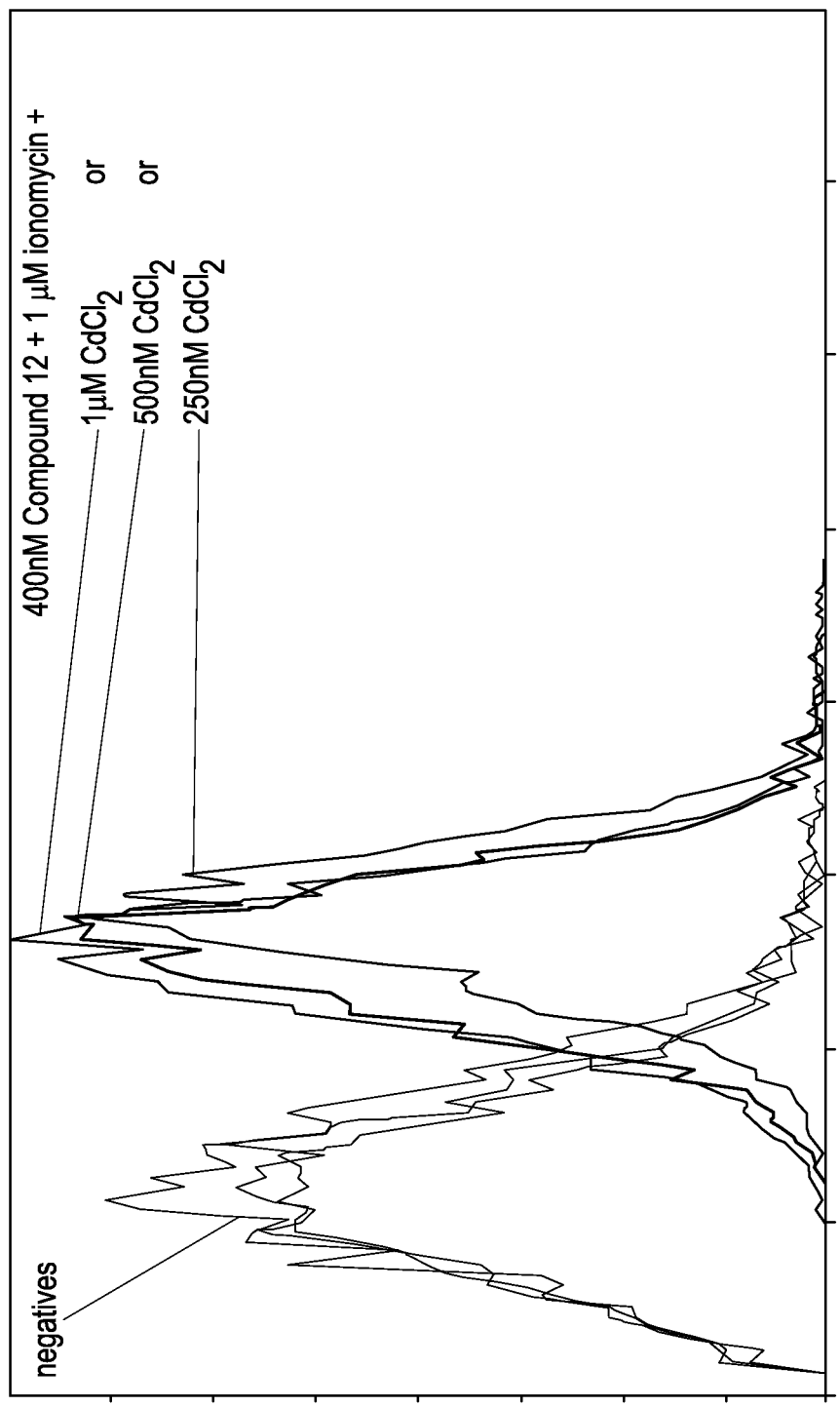
FIG. 8: Shows the detection of intracellular cadmium ions (250 nM to 1 μM added to Jurkat cells in the presence of an ionophore) with Compound 12.

Jurkat cells were suspended at 1×10$^6$/ml in saline (0.85% sodium chloride), and 400 nM Compound 12 was added to 1 ml cells, incubated at 37° C. for 1 hr, washed once with saline, and resuspended in either saline or 1 µM, 500 nM, or 250 nM CdCl$_2$ 1 µM ionomycin was added to the samples, incubated for 30 minutes at 37° C., and washed ×2 in saline. The cell pellet was resuspended in saline and analyzed on a flow cytometer. The 488 nm laser was used for excitation, a gate was made on Forward Scatter vs Side Scatter, and single color fluorescence was collected with 525/20BP emission filter. The results demonstrate that the present compound 12 binds and detects 1 µM, 500 nM, and 250 nM concentrations of cadmium ions, See FIG. 8.

Example 13

Dual Staining with Propidium Iodide (to Distinguish Dead Cells) and Compound 12 (to Detect Cadmium Ions)

Figure 9A:
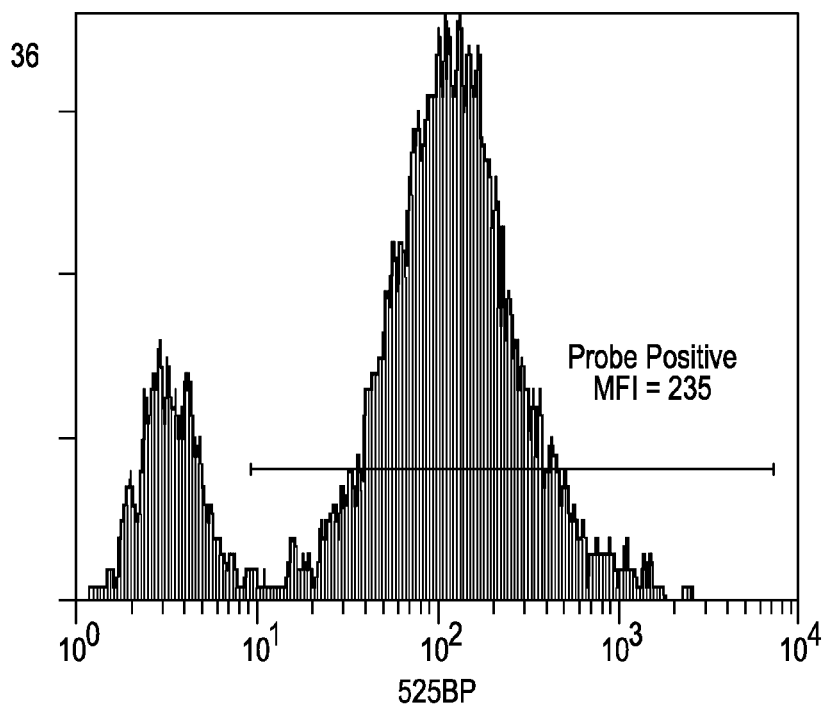
FIG. 9: Shows that Compound 12 stains only viable cells (when incubated with $CdCl_2$ in the presence of an ionophore) without causing cell death wherein 9a) is the fluorescence from Compound 12 (incubated with cadmium chloride solution), collected at 525/20BP; 9b) is the fluorescence from Propidium Iodide (PI), collected at 610/20BP; 9c) is a dual color fluorescence plot (525BP vs 610BP) wherein the cells on the bottom right quadrant are positive for Compound 12 (live cells incubated with $CdCl_2$ solution) while the cells in the top left quadrant are positive for PI (dead cells).
Figure 9B:
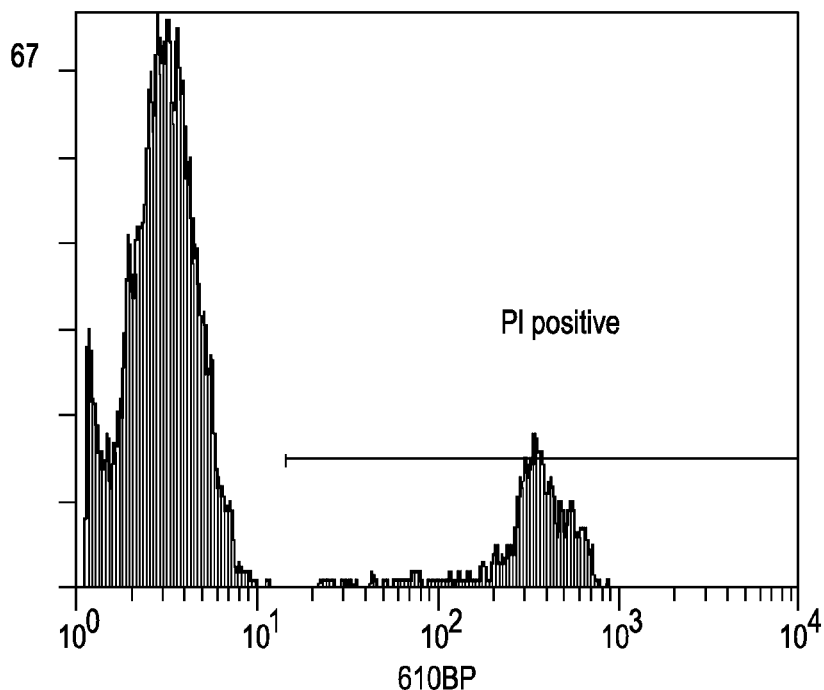
Figure 9C:
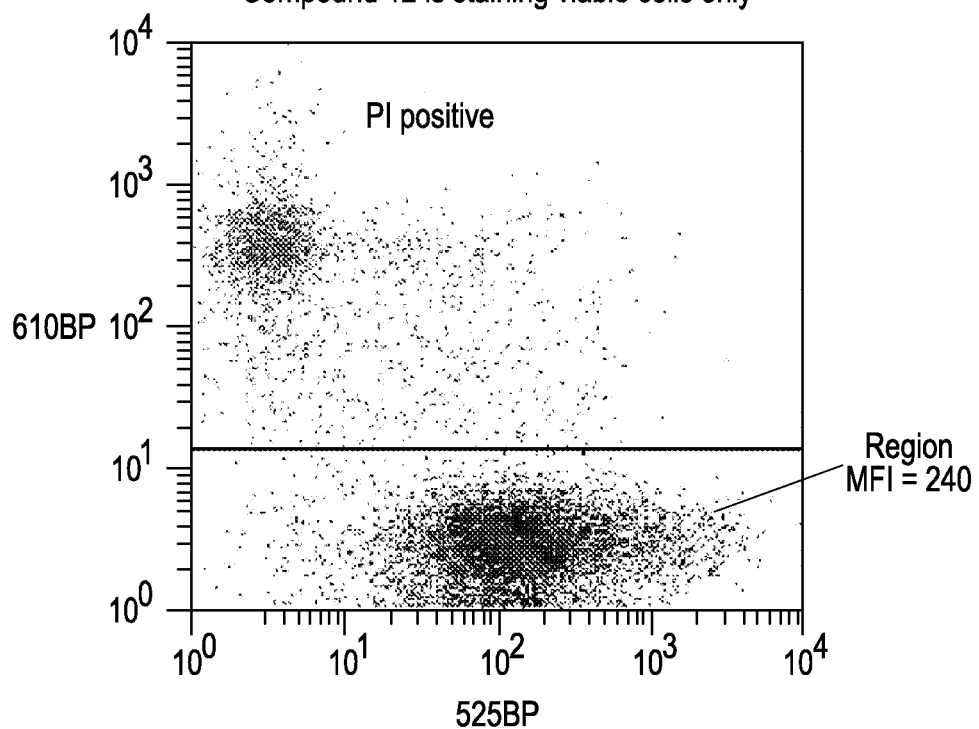

Jurkat cells were suspended at 1×10$^6$/ml in saline (0.85% sodium chloride), and 1 µM Compound 12 was added to 1 ml cells, incubated at 37° C. for 1 hr, washed once with saline, and resuspended in either saline or 100 µM CdCl$_2$ 1 µM Ionomycin was added to the samples, incubated for 30 minutes at 37° C., and washed ×2 in saline. The cell pellet was resuspended in saline, Propidium Iodide was added at 150 µM, incubated for 5 min at room temperature, and tubes were analyzed on the flow cytometer. The 488 nm laser was used for excitation, and dual color fluorescence was collected with 525/20BP emission filter for Compound 12 and 610/20BP emission filter for propidium iodide. The results demonstrate that Compound 12 is staining viable cells only and does not cause cell death, See FIG. 9.

Example 14

Compound 12 Tested with CdCl$_2$ (5-500 µM)

Figure 10:
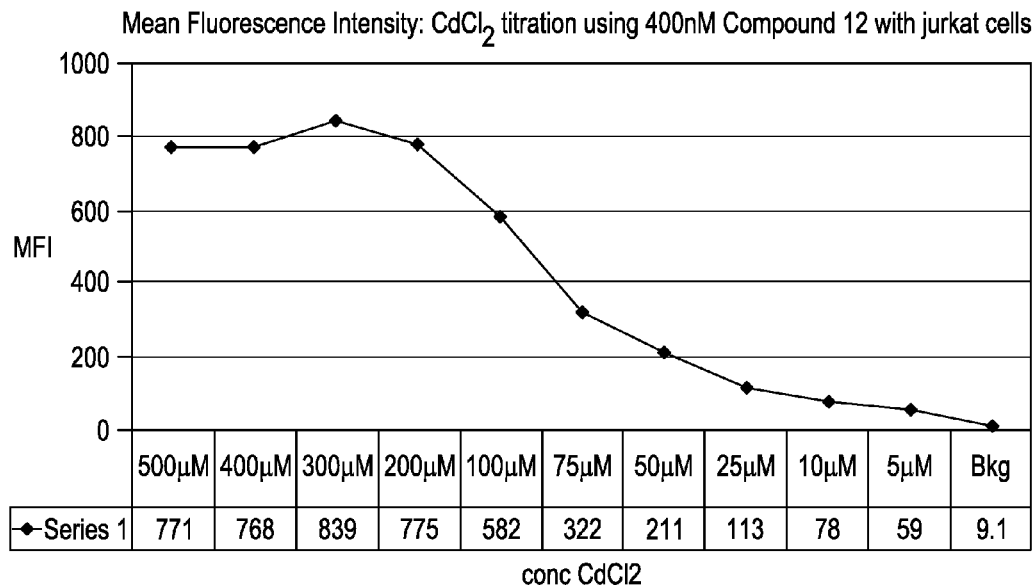
FIG. 10: Shows the change in fluorescence intensity of Compound 12 based on concentration of $CdCl_2$ (5 μM to 500 μM) added to cells as a plot of Mean Fluorescence Intensity (MFI) versus $CdCl_2$ concentration wherein the MFI increases with increasing $PbCl_2$ concentration.

Jurkat cells were suspended at 1×10$^6$/ml in saline (0.85% sodium chloride), and 400 nM Compound 12 was added to 1 ml cells, incubated at 37° C. for 1 hr, washed once with saline, and resuspended in either saline or a range of CdCl$_2$ solutions of 5-500 nM. 1 µM Ionomycin was added to the samples, incubated 30 minutes at 37° C., and washed ×2 in saline. The cell pellet was resuspended in saline and analyzed on a flow cytometer. The 488 nm laser was used for excitation, a gate was made on Forward Scatter vs Side Scatter, and single color fluorescence was collected with 525/20BP emission filter. The results demonstrate increasing fluorescence with increasing CdCl$_2$ concentration and that 5 µM CdCl$_2$ is distinguished from the background fluorescence, See FIG. 10.

Example 15

Detection of Intracellular Lead Ions in Human Red Blood Cells with Compound 12

Figure 11:
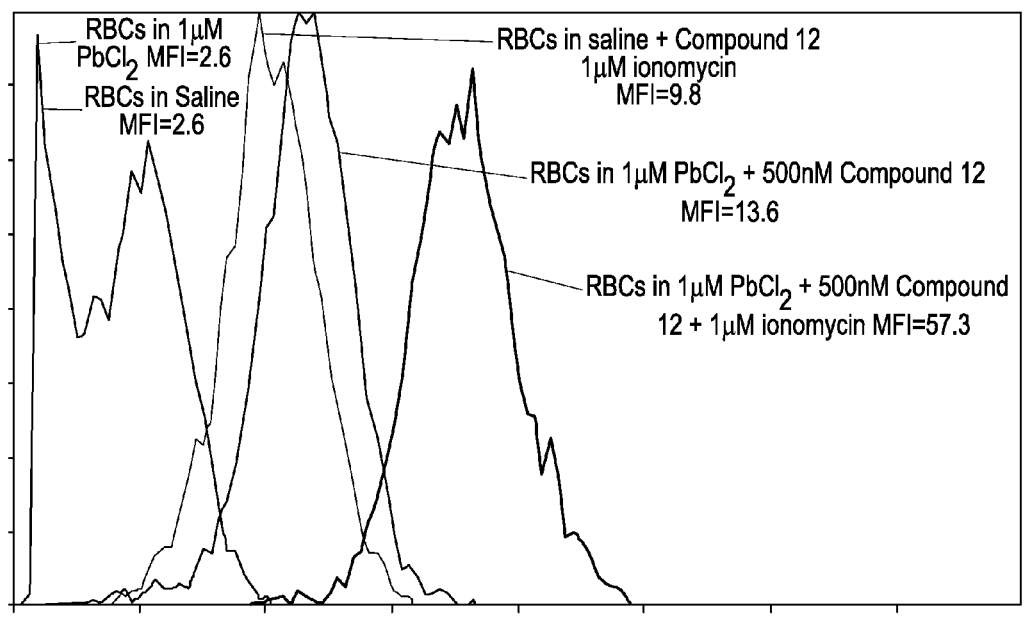
FIG. 11: Shows the detection (MFI=57.3) of intracellular lead ions (1 μM PbCl2 and 1 μM ionomycin) in human red blood cells with Compound 12 (500 nM) compared to negative controls (MFI=2.6-13.6).
Figure 12A:
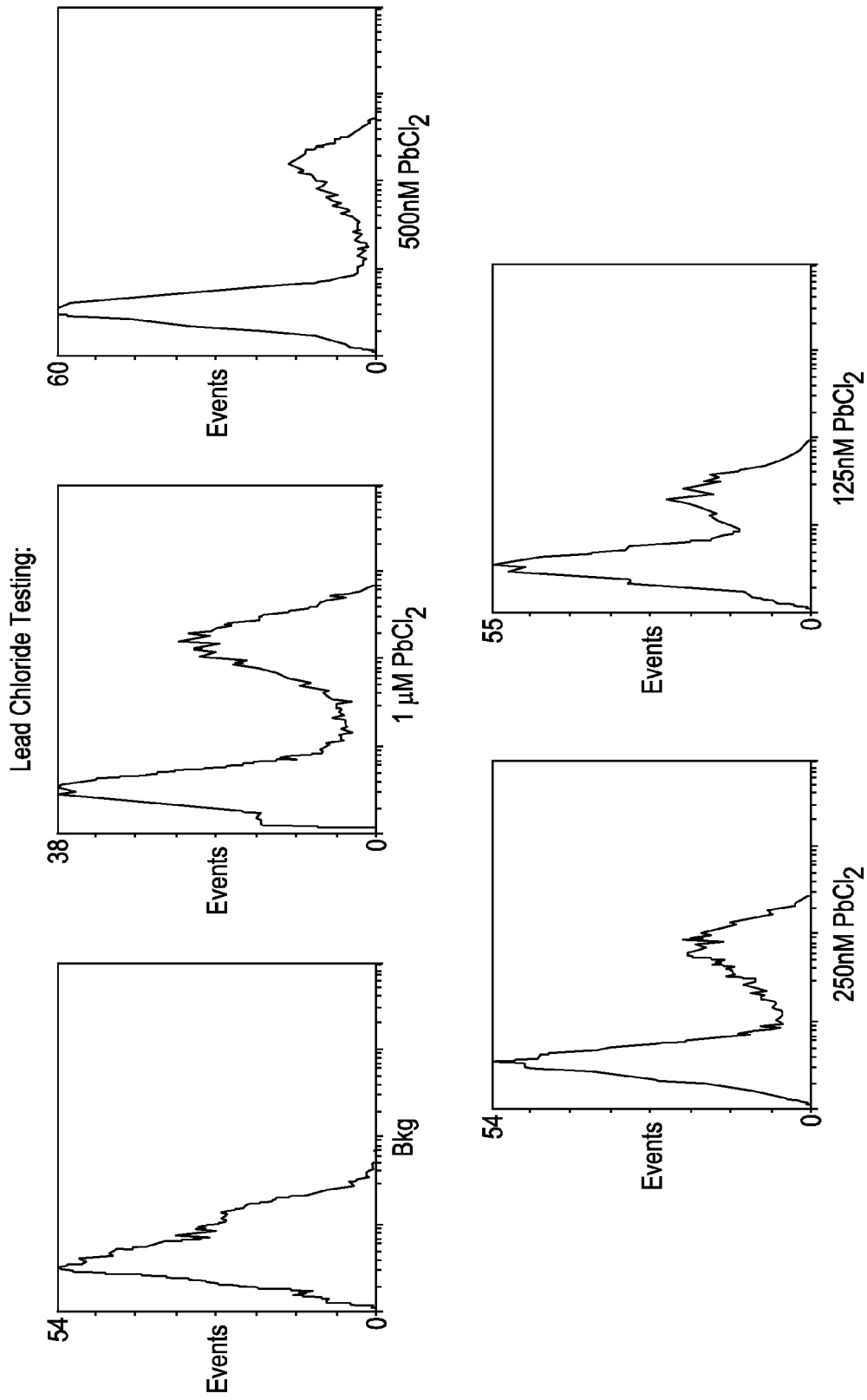
FIG. 12a) shows five histograms (0, 125 nM, 250 nM, 500 nM and 1 μM of $PbCl_2$) of the detection of intracellular lead ions wherein the cells in the top section are the dead cells (Propidium Iodide) and the cells on the bottom section are the live cells stained with Compound 12 (400 nM); 12b) is three dual color labeled plots, wherein panel A is background fluorescence from live and dead cells, Panel B is cells incubated with Compound 12 (400 nM), ionomycin (1 μM) and $PbCl_2$ (500 nM) vs PI and Panel C is Panel B cells incubated with the intracellular metal chelator TPEN, the drop in fluorescence from the viable cells (cells on the bottom section) demonstrates that the fluorescence is due to the lead chloride in the cells; 12c) shows four histograms (0, 25 uM, 50 μM and 100 μM of $CdCl_2$); 12d) is three dual color labeled plots are shown, wherein Panel A is background fluorescence from live and dead cells, Panel B is cells incubated with 400 nM Compound 12, 100 μM $CdCl_2$ and 1 μM ionomycin vs PI and Panel C is Panel B cells incubated with the intracellular metal chelator TPEN, the drop in fluorescence from the viable cells (cells on the bottom section) demonstrates that the fluorescence is due to the cadmium chloride in the cells.
Figure 12B:
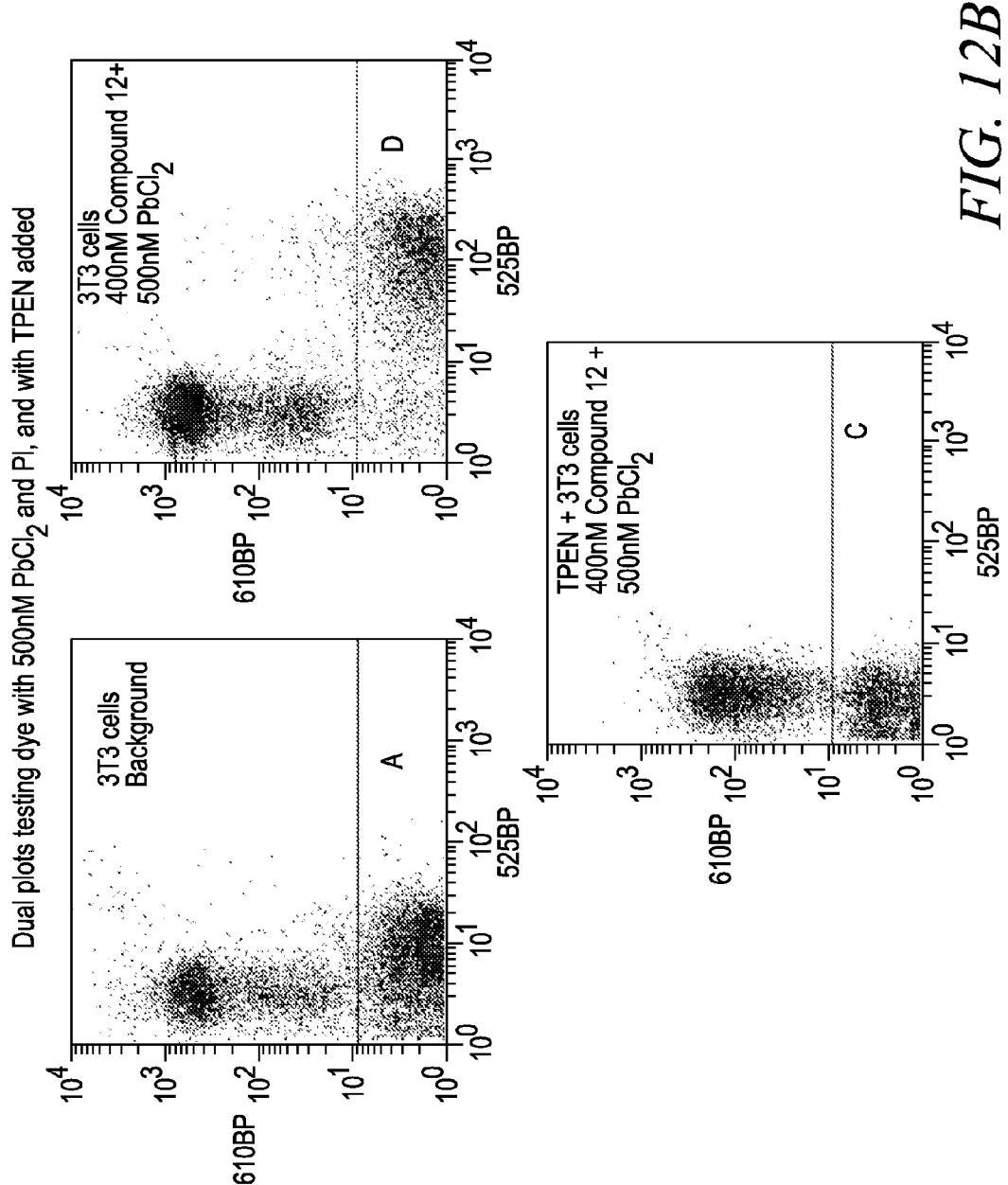
FIG. 12: Shows that the fluorescent signal is due to intracellular Pb or Cd ions respectively.
Figure 12C:
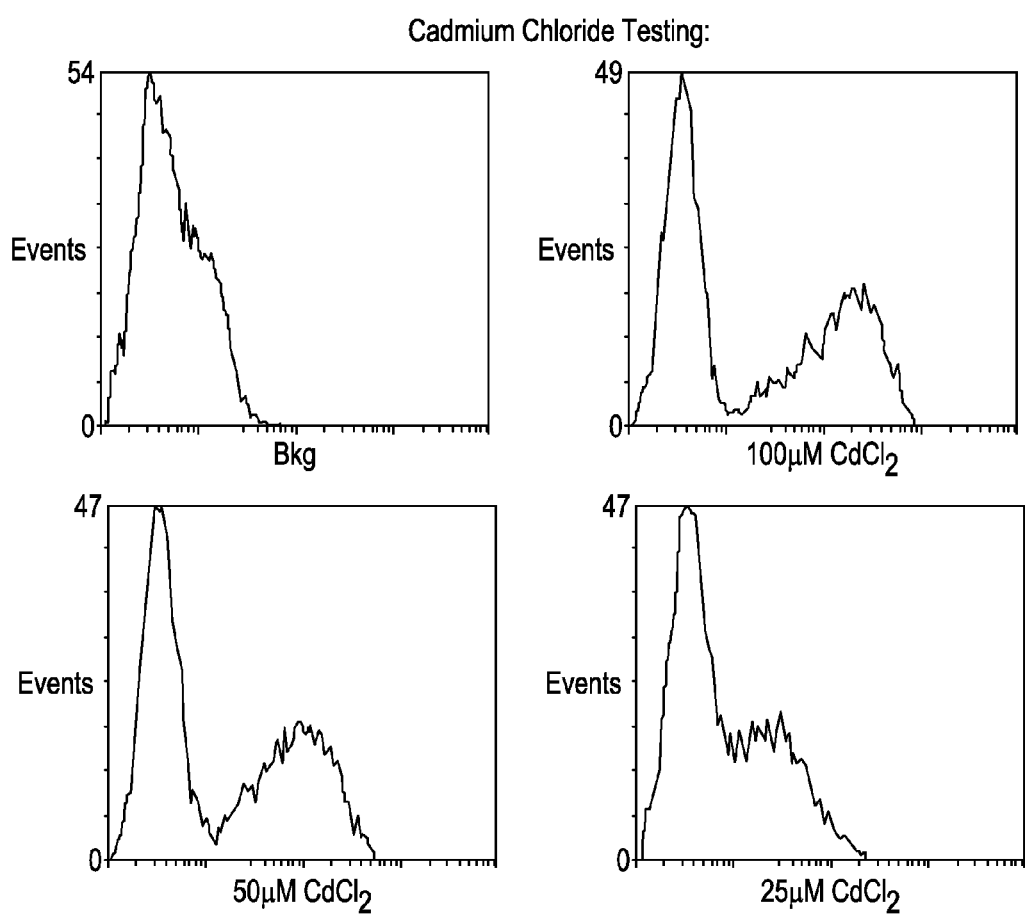
Figure 12D:
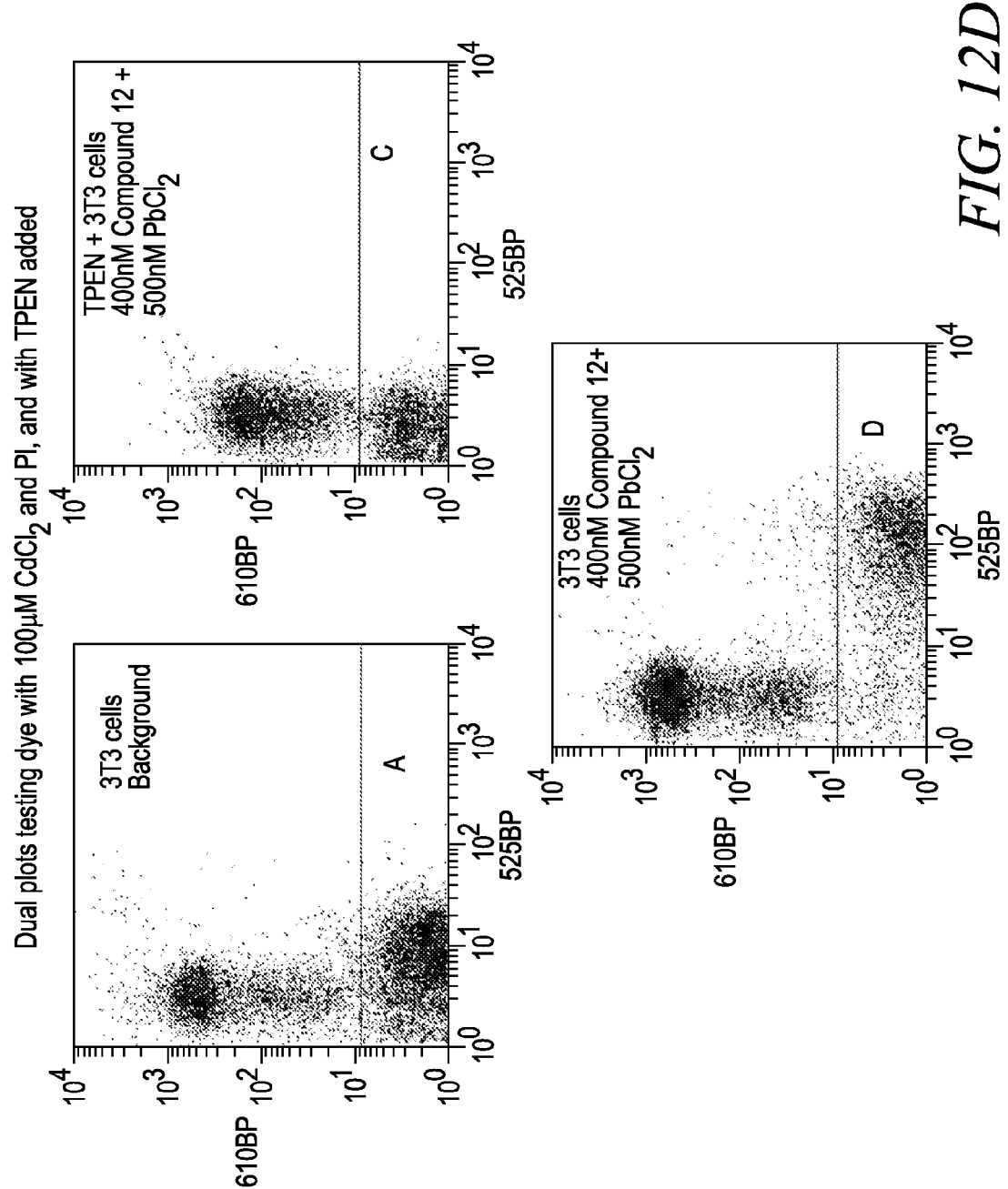

Sodium Heparin anticoagulated whole blood was washed twice in warmed saline, 1 ml RBCs in saline at 1×10$^6$ cells/ml was added to tubes, 500 nM Compound 12 was added, cells were incubated at 37° C. for 60 minutes, protected from light, and washed with saline. The cell pellet was resuspended in either saline or 1 µM PbCl$_2$+/−ionomycin. Cells incubated with Compound 12 in the presence of 1 µM PbCl$_2$ and 1 µM ionomycin gave fluorescence (MFI=57.3) distinguished from the negative controls (MFI range 2.6-13.6), See FIG. 11.

Example 16

Testing of Compound 12 on 3T3 Cells with Both Cadmium Chloride Solution and Lead Chloride Solution Testing was performed using adherent cells 3T3 with Compound 12 at concentration range 1 µM. 500 nM, 250 nM and 125 nM of PbCl$_2$ and at concentration range 100 uM, 50 µM and 25 µM of CdCl$_2$. The 3T3 cells were suspended at 5×10$^6$/ml in saline (0.85% sodium chloride), and 400 nM Compound 12 was added to 1 ml cells, incubated at 37° C. for 1 hr, washed once with saline, and resuspended in either saline or a range of CdCl$_2$ and PbCl$_2$ solutions. 1 µM Ionomycin was added to tubes, incubated for 30 minutes at 37° C., and washed ×2 in saline. The cell pellet was resuspended in saline, Propidium Iodide was added at 150 µM, incubated for 5 min at room temperature, and the samples were analyzed on a flow cytometer. The 488 nm laser was used for excitation, and dual color fluorescence was collected with 525/20BP emission filter for Compound 12 and 610/20BP emission filter for Propidium Iodide.

After fluorescence acquisition, TPEN, a cell-permeant heavy metal chelator, was added to the samples. TPEN was used to chelate the heavy metal, demonstrated by drop of fluorescence after TPEN addition.

The preceding examples can be repeated with similar success by substituting the specifically described heavy metal-binding compounds and heavy metal binding conditions of the preceding examples with those generically and specifically described in the forgoing description. One skilled in the art can easily ascertain the essential characteristics of the present invention, and without departing from the spirit and scope thereof, can make various changes and modifications of the invention to adapt to various usages and conditions.

All patents and patent applications mentioned in this specification are herein incorporated by reference to the same extent as if each individual patent or patent application was specifically and individually indicated to be incorporated by reference.

What is claimed is:

1. A kit for detecting metal ions in a sample, wherein the kit comprises a compound having the formula:

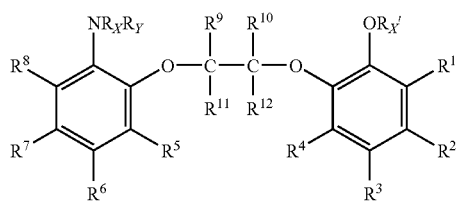

wherein
$R_X$ is —$CH_2CO_2R$; $R_Y$ is —$CH_2CO_2R$; $R_X{}'$ is —$CH_2CO_2R$;
wherein R is H, a salt ion or —$CH_2OC(O)(CH_2)_nCH_3$ and n is 0 to 6;
$R^1$ is hydrogen; $R^2$ is hydrogen;
$R^3$ is hydrogen, halogen, alkyl, substituted alkyl, alkoxy, substituted alkoxy, hydroxyl, aryl, substituted aryl, heteroaryl, substituted heteroaryl, amino, substituted amino, alkylamino, substituted alkylamino, aldehyde, carboxyl, azido, nitro, nitroso, cyano, thioether, sulfoalkyl, carboxyalkyl, aminoalkyl, reporter molecule, reactive group, carrier molecule or solid support;
$R^4$ is hydrogen; $R^5$ is hydrogen;
$R^6$ is hydrogen, halogen, alkyl, substituted alkyl, alkoxy, substituted alkoxy, hydroxyl, aryl, substituted aryl, heteroaryl, substituted heteroaryl, amino, substituted amino, alkylamino, substituted alkylamino, aldehyde, carboxyl, azido, nitro, nitroso, cyano, thioether, sulfoalkyl, carboxyalkyl, aminoalkyl, reporter molecule, reactive group, carrier molecule or solid support;
$R^7$ is hydrogen, halogen, alkyl, substituted alkyl, alkoxy, substituted alkoxy, hydroxyl, aryl, substituted aryl, heteroaryl, substituted heteroaryl, amino, substituted amino, alkylamino, substituted alkylamino, aldehyde, carboxyl, azido, nitro, nitroso, cyano, thioether, sulfoalkyl, carboxyalkyl, aminoalkyl, reporter molecule, reactive group, carrier molecule or solid support;
$R^8$ is hydrogen; $R^9$ is hydrogen; $R^{10}$ is hydrogen; $R^{11}$ is hydrogen; and $R^{12}$ is hydrogen.

2. The kit according to claim 1, further comprising instructions for detecting the presence or absence of lead, mercury, nickel, lanthanum or cadmium ions in a sample.

3. The kit according to claim 1, further comprising instructions for detecting the presence or absence of lead, mercury, nickel, lanthanum or cadmium ions in a sample using flow cytometry.

4. The kit according to claim 1, further comprising one or more of a sample preparation reagent, a buffering agent, aqueous metal ion reporter molecule dilution buffer, an additional detection reagent, a metal ion calibration reagent, a positive control, a metal ion indicator other than for lead, mercury, nickel, lanthanum or cadmium ions, an antibody or fragment thereof or a reference dye standard.

5. The kit according to claim 1, wherein R is H, a salt ion or $CH_2OC(O)CH_3$.

6. The kit according to claim 1, wherein said R is hydrogen or a salt ion.

7. The kit according to claim 1, wherein said R is $CH_2OC(O)CH_3$.

8. The kit according to claim 1, wherein at least one of $R^3$, $R^6$ and $R^7$ is a reporter molecule.

9. The kit according to claim 1, wherein $R^3$ or $R^6$ is a reporter molecule.

10. The kit according to claim 1, wherein the reporter molecule is a chromophore, fluorophore, fluorescent protein, phosphorescent dye or a tandem dye.

11. The kit according to claim 1, wherein the reporter molecule is a xanthene, indole, cyanine, oxazole, dansyl, borapolyazaindacene, benzofuran, quinazolinone, benzazole, oxazine, pyrene, naphthalene, coumarin, biotin, enzyme substrate or fluorescent protein.

12. The kit according to claim 11, wherein the xanthene is a substituted or unsubstituted fluorescein, substituted or unsubstituted rhodamine, substituted or unsubstituted rhodol, or substituted or unsubstituted rosamine.

13. The kit according to claim 11, wherein the reporter molecule is independently substituted by hydrogen, halogen, amino, substituted amino, alkyl, substituted alkyl, aryl, substituted aryl, heteroaryl, substituted heteroaryl, alkoxy, sulfo, solid support, reactive group or carrier molecule.

14. The kit according to claim 11, wherein the reporter molecule is independently substituted by a lipophilic group.

15. The kit according to claim 14, wherein the lipophilic group is an AM or acetate ester.

16. The kit according to claim 1, wherein the reporter group, reactive group, solid support and carrier molecule comprise a linker that is a single covalent bond, or a covalent linkage that is linear or branched, cyclic or heterocyclic, saturated or unsaturated, having 1-20 nonhydrogen atoms selected from the group consisting of C, N, P, O and S; and are composed of any combination of ether, thioether, amine, ester, carboxamide, sulfonamide, hydrazide bonds and aromatic or heteroaromatic bonds.

17. The kit according to claim 1, wherein the reactive group is an acrylamide, an activated ester of a carboxylic acid, a carboxylic ester, an acyl azide, an acyl nitrile, an aldehyde, an alkyl halide, an anhydride, an aniline, an amine, an aryl halide, an azide, an aziridine, a boronate, a diazoalkane, a haloacetamide, a haloalkyl, a halotriazine, a hydrazine, an imido ester, an isocyanate, an isothiocyanate, a maleimide, a phosphoramidite, a reactive platinum complex, a silyl halide, a sulfonyl halide, a thiol or a photoactivatable group.

18. The kit according to claim 1, wherein the reactive group is carboxylic acid, succinimidyl ester of a carboxylic acid, hydrazide, amine or a maleimide.

19. The kit according to claim 1, wherein the carrier molecule is an amino acid, a peptide, a protein, a polysaccharide, a nucleoside, a nucleotide, an oligonucleotide, a nucleic acid polymer, a hapten, a psoralen, a drug, a hormone, a lipid, a lipid assembly, a synthetic polymer, a polymeric microparticle, a biological cell or a virus.

20. The kit according to claim 1, wherein the carrier molecule is an antibody or fragment thereof, an avidin or streptavidin, a biotin, a blood component protein, a dextran, an enzyme, an enzyme inhibitor, a hormone, an IgG binding protein, a fluorescent protein, a growth factor, a lectin, a lipopolysaccharide, a microorganism, a metal binding protein, a metal chelating moiety, a non-biological microparticle, a peptide toxin, a phosphotidylserine-binding protein, a structural protein, a small-molecule drug, or a tyramide.

21. The kit according to claim 1, wherein the solid support is a microfluidic chip, a silicon chip, a microscope slide, a microplate well, silica gels, polymeric membranes, particles, derivatized plastic films, glass beads, cotton, plastic beads, alumina gels, polysaccharides, polyvinylchloride, polypropylene, polyethylene, nylon, latex bead, magnetic bead, paramagnetic bead, or superparamagnetic bead.

22. The kit according to claim 1, wherein the solid support is sepharose, poly(acrylate), polystyrene, poly(acrylamide), polyol, agarose, agar, cellulose, dextran, starch, FICOLL, heparin, glycogen, amylopectin, mannan, inulin, nitrocellulose, diazocellulose or starch.

23. A kit for detecting metal ions in a sample, wherein the kit comprises a compound having the formula:

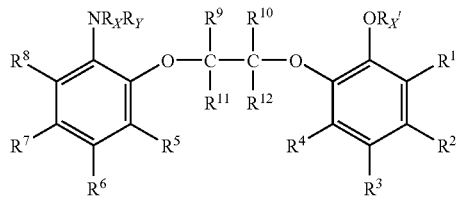

wherein
$R_X$ is —$CH_2CO_2R$; $R_Y$ is —$CH_2CO_2R$; $R_{X'}$ is —$CH_2CO_2R$;
wherein R is H, a salt ion or —$CH_2OC(O)(CH_2)_nCH_3$ and n is 0 to 6;
$R^1$ is hydrogen; $R^2$ is hydrogen;
$R^3$ is hydrogen, halogen, alkyl, substituted alkyl, alkoxy, substituted alkoxy, hydroxyl, aryl, substituted aryl, heteroaryl, substituted heteroaryl, amino, substituted amino, alkylamino, substituted alkylamino, aldehyde, carboxyl, azido, nitro, nitroso, cyano, thioether, sulfoalkyl, carboxyalkyl, aminoalkyl, reporter molecule, reactive group, carrier molecule or solid support;
$R^4$ is hydrogen; $R^5$ is hydrogen;
$R^6$ is hydrogen, halogen, alkyl, substituted alkyl, alkoxy, substituted alkoxy, hydroxyl, aryl, substituted aryl, heteroaryl, substituted heteroaryl, amino, substituted amino, alkylamino, substituted alkylamino, aldehyde, carboxyl, azido, nitro, nitroso, cyano, thioether, sulfoalkyl, carboxyalkyl, aminoalkyl, reporter molecule, reactive group, carrier molecule or solid support;
$R^7$ is hydrogen, halogen, alkyl, substituted alkyl, alkoxy, substituted alkoxy, hydroxyl, aryl, substituted aryl, heteroaryl, substituted heteroaryl, amino, substituted amino, alkylamino, substituted alkylamino, aldehyde, carboxyl, azido, nitro, nitroso, cyano, thioether, sulfoalkyl, carboxyalkyl, aminoalkyl, reporter molecule, reactive group, carrier molecule or solid support;
$R^8$ is hydrogen; $R^9$ is hydrogen; $R^{10}$ is hydrogen; $R^{11}$ is hydrogen; and $R^{12}$ is hydrogen, or
any adjacent $R^1$-$R^8$ together with the atoms to which they are joined, form a ring which is a 5-, 6- or 7-membered heterocycloalkyl, a substituted 5-, 6- or 7-membered heterocycloalkyl, a 5-, 6- or 7-membered cycloalkyl, a substituted 5-, 6- or 7-membered cycloalkyl, a 5-, 6- or 7-membered heteroaryl, a substituted 5-, 6- or 7-membered heteroaryl, a 5-, 6- or 7-membered aryl, a substituted 5-, 6- or 7-membered aryl or reporter molecule.

24. The kit-according to claim 23, wherein the compound is

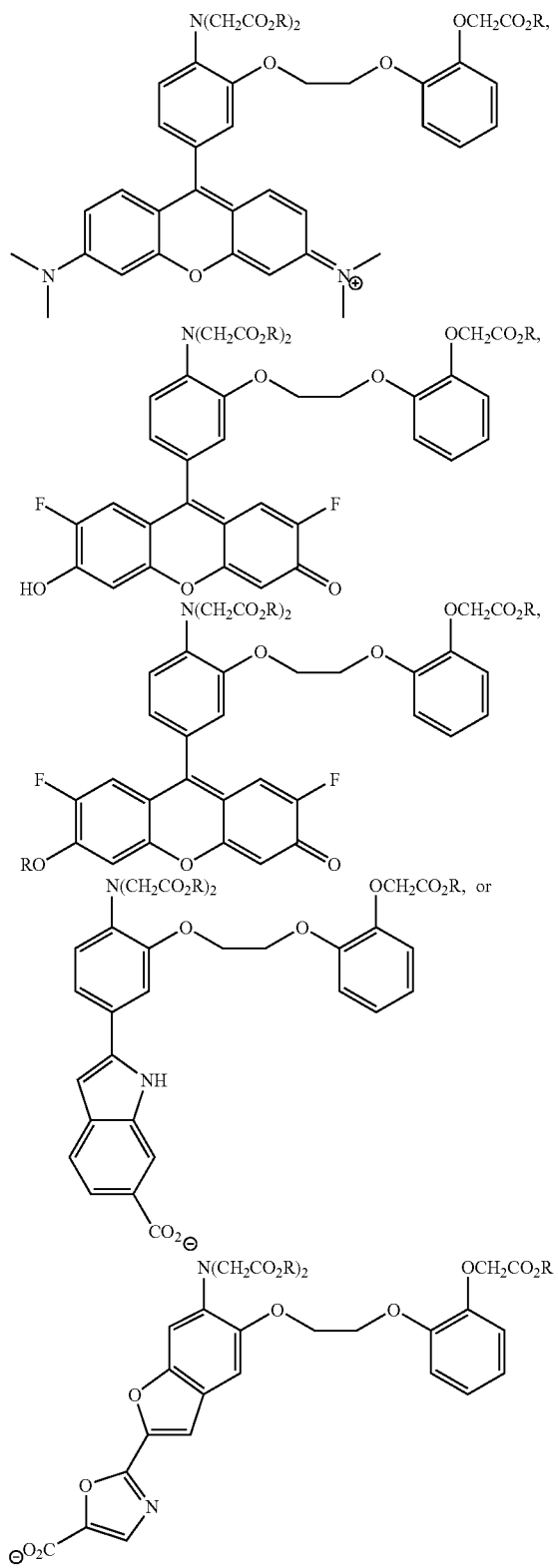

and a biologically compatible counterion.

* * * * *